US012790327B2

(12) United States Patent
Peng et al.

(10) Patent No.: US 12,790,327 B2

(45) Date of Patent: Nov. 10, 2026

(54) ATX INHIBITOR, AND PREPARATION METHOD THEREFOR AND USE THEREOF

(71) Applicant: SUZHOU ARK BIOPHARMACEUTICAL CO., LTD., Sizhou (CN)

(72) Inventors: Cheng Peng, Suzhou (CN); Mengfei Qian, Suzhou (CN); Xiashi Lv, Suzhou (CN); Jin Wu, Suzhou (CN); Wei Yin, Suzhou (CN); Fengyou Liu, Suzhou (CN); Yi Jin, Suzhou (CN); Gang Zou, Suzhou (CN); Haiqing Yuan, Suzhou (CN); Zhen Jim Wu, Suzhou (CN)

(73) Assignee: SUZHOU ARK BIOPHARMACEUTICAL CO., LTD., Suzhou (CN)

( * ) Notice: Subject to any disclaimer, the term of this patent is extended or adjusted under 35 U.S.C. 154(b) by 855 days.

(21) Appl. No.: 18/015,261

(22) PCT Filed: Jul. 8, 2021

(86) PCT No.: PCT/CN2021/105180

§ 371 (c)(1),
(2) Date: Jan. 9, 2023

(87) PCT Pub. No.: WO2022/007882

PCT Pub. Date: Jan. 13, 2022

(65) Prior Publication Data

US 2023/0295159 A1 Sep. 21, 2023

(30) Foreign Application Priority Data

Jul. 9, 2020 (CN) ......................... 202010658085.8
Mar. 23, 2021 (CN) ......................... 202110308656.X

(51) Int. Cl.
*C07D 471/04* (2006.01)

(52) U.S. Cl.
CPC ........ *C07D 471/04* (2013.01); *C07B 2200/05* (2013.01)

(58) Field of Classification Search
CPC .. C07D 471/04; C07D 471/00; C07D 463/00; C07D 451/00; C07D 471/02; C07D 487/04; C07B 2200/05; A61P 11/00; A61P 25/28; A61P 35/00; A61P 37/00; A61P 9/00
USPC ................................................. 514/210, 180
See application file for complete search history.

(56) References Cited

FOREIGN PATENT DOCUMENTS

| | | | | |
|---|---|---|---|---|
| CN | 105143221 A | | 12/2015 | |
| CN | 105339370 A | | 2/2016 | |
| CN | 109384803 A | | 2/2019 | |
| WO | 2014202763 A1 | | 12/2014 | |
| WO | 2019158107 A1 | | 8/2019 | |
| WO | WO-2019228403 A1 | * | 12/2019 | A61K 45/06 |
| WO | 2020177729 A1 | | 9/2020 | |

OTHER PUBLICATIONS

Joncour et al., J. Med. Chem., vol. 60, Jul. 21, 2017, pp. 7371-7392 (Year: 2017).*
Agnées Joncour et al., "Discovery, Structure-Activity Relationship, and Binding Mode of an Imidazo[1,2-a]pyridine Series of Autotaxin Inhibitors" J. Med. Chem. 2017, 60, 7371-7392 (Jul. 17, 2017).

* cited by examiner

*Primary Examiner* — Scarlett Y Goon
*Assistant Examiner* — Grace Ching Hsu
(74) *Attorney, Agent, or Firm* — SZDC Law PC

(57) ABSTRACT

Disclosed are an ATX inhibitor, a preparation method therefor, and the use thereof, which belong to the technical field of pharmaceutical chemistry. In particular, the ATX inhibitor is a compound having the structure of formula I', or a pharmaceutically acceptable salt, an ester, an isomer, a solvate, a prodrug or an isotope marker thereof. Compared with the existing ATX inhibitor GLPG-1690, the ATX inhibitor has higher inhibitory activity, also has excellent efficacy, in vitro/in vivo pharmacokinetic properties and safety, and has broad clinical application prospects.

I'

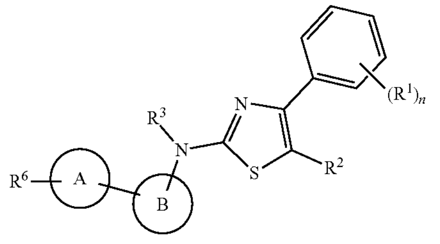

23 Claims, No Drawings

ATX INHIBITOR, AND PREPARATION METHOD THEREFOR AND USE THEREOF

CROSS-REFERENCES TO RELATED APPLICATIONS

The present application is the National Stage Application of PCT/CN2021/105180, filed on Jul. 8, 2021, which claims priority to Chinese patent application No. 202010658085.8, filed on Jul. 9, 2020, and entitled "ATX INHIBITOR, PREPARATION METHOD AND USE THEREOF", and Chinese patent application No. 202110308656.X, filed on Mar. 23, 2021, and entitled "ATX INHIBITOR, PREPARATION METHOD AND USE THEREOF", each of which is incorporated by reference herein in its entirety.

TECHNICAL FIELD

The present disclosure pertains to the field of medicinal chemistry, in particular relating to an ATX inhibitor and a preparation method thereof.

BACKGROUND

Autotaxin (ATX, also known as ENPP2 [ectonucleotide pyrophosphatase/phosphodiesterase 2] or lysophospholipase D) is a member of ectonucleotide pyrophosphatase/phosphodiesterase (ENPP) family. ATX can convert lysophosphatidylcholine (LPC) to bioactive lysophosphatidic acid (LPA). LPA consists of a glycerol chain, a phosphate group and an aliphatic acyl chain that varies in length and saturation degree. Once being produced, LPA can be mediated by six specific cell surface receptor proteins (LPA1-6), namely G protein-coupled receptors, to exert its biological activities. Many evidences suggest that ATX contributes substantially to the generation of LPA in blood. An ATX-LPA signaling pathway involves in cell survival, migration and proliferation, and thus critically linked to a great diversity of serious diseases, such as fibrotic diseases (mainly idiopathic pulmonary fibrosis, IPF), cancer, proliferative diseases, inflammatory diseases, autoimmune diseases, cardiovascular diseases, and neurodegenerative diseases. In fact, overexpression of ATX often occurs in cancer tissues, such as breast cancer, colorectal cancer and glioblastoma.

At present, GLPG-1690 serves to inhibit ATX, and has been subjected to a phase III clinical trial, which is used to treat idiopathic pulmonary fibrosis (IPF). Some evidences have indicated that ATX/LPA signaling plays a role in a great diversity of lung diseases by regulating the biological properties of lung epithelial cells, fibroblasts and smooth muscle cells.

However, although GLPG-1690 has ATX inhibitory activity, its inhibitory activity is not significant, and therefore, it is still necessary to develop more ATX inhibitors with higher inhibitory activity.

SUMMARY

The Problem to be Solved by the Disclosure

In order to solve the above technical problems, the present disclosure provides a novel class of heteroaromatic ring compounds, which have high inhibitory activity against ATX, while exhibiting excellent efficacy, in vitro/in vivo pharmacokinetic properties and safety, and thus having promising prospects in clinical application.

Solutions to the Problem

To solve the above problems, the present disclosure provides the following technical solution:

A compound having a structure of Formula I' or a pharmaceutically acceptable salt, ester, isomer, solvate, prodrug or isotopically labelled compound thereof,

I'

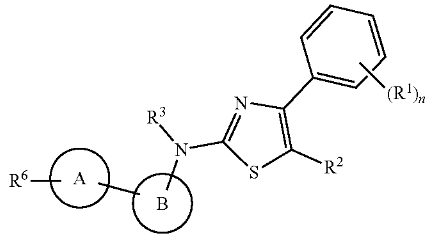

wherein n is any integer from 0 to 5;

if present, each $R^1$ is independently selected from the group consisting of hydrogen, deuterium, cyano, halogen, amino, hydroxyl, —COOH, —CHO, —$NO_2$, $C_{1-6}$ alkylamino, $C_{1-6}$ alkoxy, and $C_{1-6}$ alkyl, $C_{3-7}$ cycloalkyl and 3- to 7-membered heterocycloalkyl that are unsubstituted or substituted with substituents selected from the group consisting of cyano, amino, hydroxyl, halogen, $C_{1-6}$ alkyl, and $C_{1-6}$ alkoxy;

$R^2$ is selected from the group consisting of hydrogen, deuterium, halogen, cyano, amino, hydroxyl, —COOH, —CHO, —$NO_2$, $C_{1-6}$ alkyl, $C_{1-6}$ alkoxy, $C_{1-6}$ alkylamino, —C(═O)$NH_2$, —NH(C═O)$CH_3$, and 3- to 7-membered heterocycloalkyl;

$R^3$ is selected from the group consisting of hydrogen, deuterium, $C_{1-6}$ alkyl, $C_{3-7}$ cycloalkyl, and $C_{1-6}$ alkyl, $C_{3-7}$ cycloalkyl and 3- to 7-membered heterocycloalkyl that are substituted with substituents selected from the group consisting of cyano, amino, hydroxyl, halogen, $C_{1-6}$ alkyl, and $C_{1-6}$ alkoxy;

ring B is any one of the following structures:

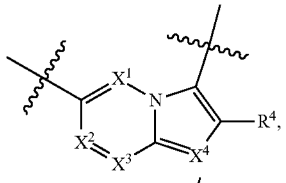

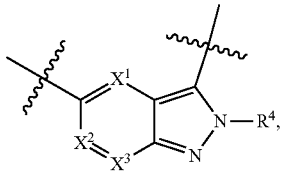

and

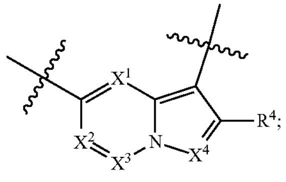

$R^4$ is selected from the group consisting of hydrogen, deuterium, halogen, cyano, hydroxyl, amino, $C_{1-6}$ alkyl, $C_{1-6}$ alkoxy, $C_{1-6}$ alkylamino, $C_{3-7}$ cycloalkyl, and 3- to 7-membered heterocycloalkyl;

$X^1$, $X^2$, $X^3$ and $X^4$ are each independently N or $CR^5$;

$R^5$ is selected from the group consisting of hydrogen, deuterium, halogen, $C_{1-6}$ alkyl, and $C_{1-6}$ alkyl, $C_{3-7}$ cycloalkyl and 3- to 7-membered heterocycloalkyl that are substituted with substituents selected from the group consisting of cyano, amino, hydroxyl, halogen, $C_{1-6}$ alkyl, and $C_{1-6}$ alkoxy;

ring A is selected from the group consisting of $C_{6-10}$ aryl and 5- to 10-membered heteroaryl that are substituted or unsubstituted, and the substitution is a substitution with 1 to 3 substituents selected from the group consisting of hydroxyl, amino, halogen, cyano, $C_{1-6}$ alkyl, $C_{1-6}$ haloalkyl, $C_{3-7}$ cycloalkyl, 3- to 7-membered heterocycloalkyl, $C_{1-6}$ alkylamino, and $C_{1-6}$ alkoxy;

$R^6$ is $-L^1-L^2-W^1$;

$L^1$ is selected from the group consisting of a chemical bond, $C_{1-3}$ alkylene, —O—, —C(═O)—, —C(═O)C$(R^8)_2$—, —C(═O)O—, —C(═O)NH—, —OC(═O)—, —NH—, —$SO_2$—, —$NHSO_2$—, and —$SO_2NH$—; wherein $R^8$ is hydrogen or $C_{1-6}$ alkyl;

$L^2$ is selected from the group consisting of a chemical bond, —O—, —C(═O)—, —C(═O)$CH_2$—, —C(═O)O—, —OC(═O)—, —C(═O)NH—, —$NR^7$—, —$NHCH_2$—, —$SO_2$—, —$NR^7SO_2$—, —$SO_2NR^7$—, —C(═O)$NR^7$—, and —$NR^7$C(═O)—; wherein $R^7$ is hydrogen or $C_{1-6}$ alkyl;

$W^1$ is a substituted or unsubstituted group as follows: hydrogen, deuterium, amino, cyano, $C_{1-6}$ alkyl, halogen, hydroxyl, $C_{1-6}$ alkoxy, $C_{1-6}$ alkylamino, carboxyl, $C_{6-10}$ aryl, 5- to 10-membered heteroaryl, $C_{3-7}$ cycloalkyl or 3- to 7-membered heterocycloalkyl; the substitution is a substitution with 1 or 2 substituents selected from the group consisting of oxo, hydroxy, amino, hydroxymethyl, aminomethyl, cyano, $C_{1-6}$ alkyl, $C_{1-6}$ alkyl-C(═O)O— and halogen.

Further, the above compound of Formula I' is a compound having a structure of Formula I,

I

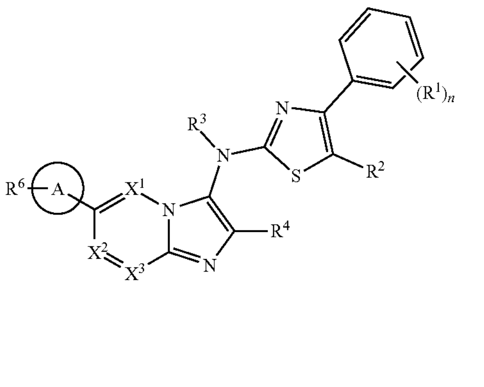

wherein n, $R^1$, $R^2$, $R^3$, $R^4$, $R^6$, $X^1$, $X^2$, $X^3$, and ring A are as defined in Formula I'.

Still further, the above compound of Formula I' is a compound having a structure of Formula I-1,

I-1

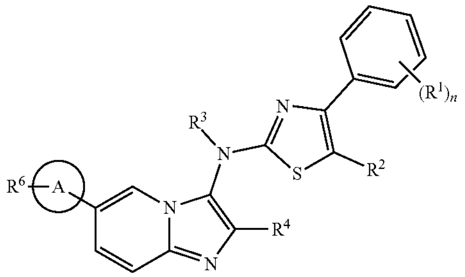

wherein n, $R^1$, $R^2$, $R^3$, $R^4$, $R^6$, and ring A are as defined in Formula I'.

Further, the above compound of Formula I' is a compound having a structure of Formula II,

II

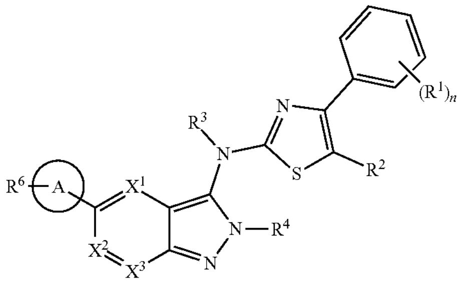

wherein n, $R^1$, $R^2$, $R^3$, $R^4$, $R^6$, $X^1$, $X^2$, $X^3$, and ring A are as defined in Formula I'.

Still further, the above compound of Formula I' is a compound having a structure of Formula II-1,

II-1

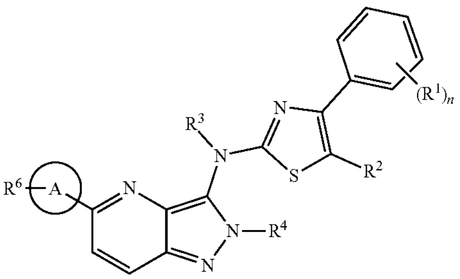

wherein n, $R^1$, $R^2$, $R^3$, $R^4$, $R^6$, and ring Aare as defined in Formula I'.

Further, the above compound of Formula I' is a compound having a structure of Formula III,

III

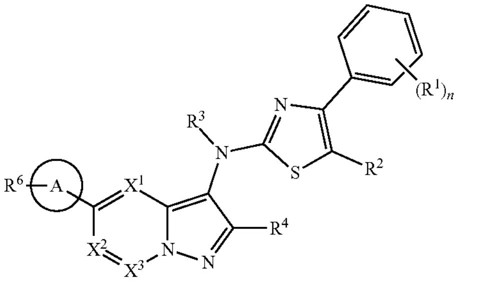

wherein n, $R^1$, $R^2$, $R^3$, $R^4$, $R^6$, $X^1$, $X^2$, $X^3$, and ring A are as defined in Formula I'.

Still further, the above compound of Formula I' is a compound having a structure of Formula III-1,

III-1

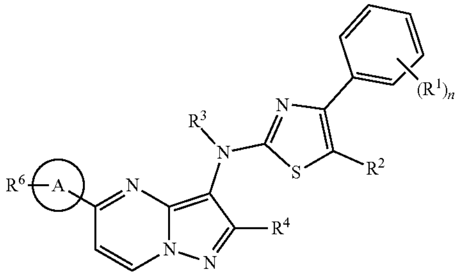

wherein n, $R^1$, $R^2$, $R^3$, $R^4$, $R^6$, and ring Aare as defined in Formula I'.

The present disclosure also provides the following compounds:

(1) 2-((2-ethyl-6-(4-(2-(3-hydroxyazetidin-1-yl)-2-oxoethyl)phenyl)imidazo[1,2-a]pyridin-3-yl)(methyl)amino)-4-(4-fluorophenyl)thiazole-5-carbonitrile;

(2) 2-((2-ethyl-6-(6-(2-(3-hydroxyazetidin-1-yl)-2-oxoethyl)pyridin-3-yl)imidazo[1,2-a]pyridin-3-yl)(methyl)amino)-4-(4-fluorophenyl)thiazole-5-carbonitrile;

(3) 2-((2-ethyl-6-(5-fluoro-6-(2-(3-hydroxyazetidin-1-yl)-2-oxoethyl)pyridin-3-yl)imidazo[1,2-a]pyridin-3-yl)(methyl)amino)-4-(4-fluorophenyl)thiazole-5-carbonitrile;

(4) 2-((2-ethyl-6-(5-(2-(3-hydroxyazetidin-1-yl)-2-oxoethyl)pyrazin-2-yl)imidazo[1,2-a]pyridin-3-yl)(methyl)amino)-4-(4-fluorophenyl)thiazole-5-carbonitrile;

(5) 2-((2-ethyl-6-(6-(2-(3-hydroxyazetidin-1-yl)-2-oxoethyl)pyridazin-3-yl)imidazo[1,2-a]pyridin-3-yl)(methyl)amino)-4-(4-fluorophenyl)thiazole-5-carbonitrile;

(6) 2-((2-ethyl-6-(6-(2-(3-hydroxyazetidin-1-yl)-2-oxoethyl)-2-methylpyridin-3-yl)imidazo[1,2-a]pyridin-3-yl)(methyl)amino)-4-(4-fluorophenyl)thiazole-5-carbonitrile;

(7) 2-((2-ethyl-6-(5-(2-(3-hydroxyazetidin-1-yl)-2-oxoethyl)pyridin-2-yl)imidazo[1,2-a]pyridin-3-yl)(methyl)amino)-4-(4-fluorophenyl)thiazole-5-carbonitrile;

(8) 2-((2-ethyl-6-(5-(3-hydroxyazetidin-1-carbonyl)pyrazin-2-yl)imidazo[1,2-a]pyridin-3-yl)(methyl)amino)-4-(4-fluorophenyl)thiazole-5-carbonitrile;

(9) 2-((2-ethyl-6-(5-(1-(3-hydroxyazetidin-1-yl)-2-methyl-1-oxopropan-2-yl)pyrazin-2-yl)imidazo[1,2-a]pyridin-3-yl)(methyl)amino)-4-(4-fluorophenyl)thiazole-5-carbonitrile;

(10) 2-((2-ethyl-6-(3-fluoro-5-(2-(3-hydroxyazetidin-1-yl)-2-oxoethyl)pyridin-2-yl)imidazo[1,2-a]pyridin-3-yl)(methyl)amino)-4-(4-fluorophenyl)thiazole-5-carbonitrile;

(11) (S)-2-((2-ethyl-6-(5-(2-(3-hydroxypyrrolidin-1-yl)-2-oxoethyl)pyrazin-2-yl)imidazo[1,2-a]pyridin-3-yl)(methyl)amino)-4-(4-fluorophenyl)thiazole-5-carbonitrile;

(12) 2-((2-ethyl-6-(5-(2-(3-(hydroxymethyl)azetidin-1-yl)-2-oxoethyl)pyrazin-2-yl)imidazo[1,2-a]pyridin-3-yl)(methyl)amino)-4-(4-fluorophenyl)thiazole-5-carbonitrile;

(13) (R)-2-((2-ethyl-6-(5-(2-(3-hydroxypyrrolidin-1-yl)-2-oxoethyl)pyrazin-2-yl)imidazo[1,2-a]pyridin-3-yl)(methyl)amino)-4-(4-fluorophenyl)thiazole-5-carbonitrile;

(14) 2-(5-(3-((5-cyano-4-(4-fluorophenyl)thiazol-2-yl)(methyl)amino)-2-ethylimidazo[1,2-a]pyridin-6-yl)pyrazin-2-yl)-N-((5-oxopyrrolidin-2-yl)methyl)acetamide;

(15) 5-(3-((5-cyano-4-(4-fluorophenyl)thiazol-2-yl)(methyl)amino)-2-ethylimidazo[1,2-a]pyridin-6-yl)-N-(2-azaspiro[3.3]heptan-6-yl)pyrazin-2-carboxamide;

(16) 2-((2-ethyl-6-(5-fluoro-6-(3-hydroxyazetidin-1-carbonyl)pyridin-3-yl)imidazo[1,2-a]pyridin-3-yl)(methyl)amino)-4-(4-fluorophenyl)thiazole-5-carbonitrile;

(17) 2-((5-(2-(1,1-dioxidoisothiazolidin-2-yl)pyrimidin-5-yl)-2-ethyl-2H-pyrazolo[4,3-b]pyridin-3-yl)(ethyl)amino)-4-(4-fluorophenyl)thiazole-5-carbonitrile;

(18) 2-((5-(2-(1,1-dioxidoisothiazolidin-2-yl)pyrimidin-5-yl)-2-ethylpyrazolo[1,5-a]pyrimidin-3-yl)(ethyl)amino)-4-(4-fluorophenyl)thiazole-5-carbonitrile;

(19) 2-((6-(5-(1,1-dioxidoisothiazolidin-2-yl)pyrazin-2-yl)-2-ethylimidazo[1,2-a]pyridin-3-yl)(ethyl)amino)-4-(4-fluorophenyl)thiazole-5-carbonitrile;

(20) N-(5-(3-((5-cyano-4-(4-fluorophenyl)thiazol-2-yl)(ethyl)amino)-2-ethylimidazo[1,2-a]pyridin-6-yl)pyrimidin-2-yl)-N-methylmethanesulfonamide;

(21) 2-((5-(2-(1,1-dioxido-1,2-thiazinan-2-yl)pyrimidin-5-yl)-2-ethyl-2H-pyrazolo[4,3-b]pyridin-3-yl)(ethyl)amino)-4-(4-fluorophenyl)thiazole-5-carbonitrile;

(22) N-(5-(3-((5-cyano-4-(4-fluorophenyl)thiazol-2-yl)(ethyl)amino)-2-ethylimidazo[1,2-a]pyridin-6-yl)pyrimidin-2-yl)-2-hydroxyethane-1-sulfonamide;

(23) 2-(ethyl(2-ethyl-5-(2-(3-hydroxyazetidin-1-yl)pyrimidin-5-yl)-2H-pyrazolo[4,3-b]pyridin-3-yl)amino)-4-(4-fluorophenyl)thiazole-5-carbonitrile;

(24) 2-(ethyl(2-ethyl-5-(2-(3-(hydroxymethyl)azetidin-1-yl)pyrimidin-5-yl)-2H-pyrazolo[4,3-b]pyridin-3-yl)amino)-4-(4-fluorophenyl)thiazole-5-carbonitrile;

(25) 1-(5-(3-((5-cyano-4-(4-fluorophenyl)thiazol-2-yl)(ethyl)amino)-2-ethyl-2H-pyrazolo[4,3-b]pyridin-5-yl)pyrimidin-2-yl)azetidin-3-yl acetate;

(26) 2-(ethyl(2-ethyl-5-(2-(4-hydroxypiperidin-1-yl)pyrimidin-5-yl)-2H-pyrazolo[4,3-b]pyridin-3-yl)amino)-4-(4-fluorophenyl)thiazole-5-carbonitrile;

(27) (S)-2-(ethyl(2-ethyl-5-(2-(3-hydroxypyrrolidin-1-yl)pyrimidin-5-yl)-2H-pyrazolo[4,3-b]pyridin-3-yl)amino)-4-(4-fluorophenyl)thiazole-5-carbonitrile;

(28) (R)-2-(ethyl(2-ethyl-5-(2-(3-hydroxypyrrolidin-1-yl)pyrimidin-5-yl)-2H-pyrazolo[4,3-b]pyridin-3-yl)amino)-4-(4-fluorophenyl)thiazole-5-carbonitrile; and

(29) 2-(ethyl(2-ethyl-5-(2-morpholinopyrimidin-5-yl)-2H-pyrazolo[4,3-b]pyridin-3-yl)amino)-4-(4-fluorophenyl)thiazole-5-carbonitrile.

The present disclosure also provides a pharmaceutical composition, comprising the above compounds having the structure of Formula I', Formula I, Formula I-1, Formula II, Formula II-1, Formula III or Formula III-1 or the pharmaceutically acceptable salt, ester, isomer, solvate, prodrug or isotopically labelled compound thereof.

The present disclosure also provides a pharmaceutical formulation, comprising the above compound having the structure of Formula I', Formula I, Formula I-1, Formula II, Formula II-1, Formula III or Formula III-1 or the pharmaceutically acceptable salt, ester, isomer, solvate, prodrug or isotopically labelled compound thereof or the above pharmaceutical composition, and the formulation is any one of a tablet, a capsule, an injection, a granule, a powder, a suppository, a pill, a cream, a paste, a gel, a pulvis, an oral solution, an inhalant, a suspension, a dry suspension, a patch, and a lotion.

The present disclosure also provides the above compound having the structure of Formula I', Formula I, Formula I-1, Formula II, Formula II-1, Formula III or Formula III-1 or the pharmaceutically acceptable salt, ester, isomer, solvate, prodrug or isotopically labelled compound thereof, or the above pharmaceutical composition or pharmaceutical formulation, for using in the prevention and/or treatment of a related disease with a pathologic feature of increased ATX expression; preferably, the related disease with the pathologic feature of increased ATX expression includes cancer, fibrotic diseases, metabolic diseases, myelodysplastic syndrome, respiratory diseases, cardiovascular diseases, autoimmune diseases, inflammation, dermatological diseases, nervous system diseases or pain; more preferably, the related disease with the pathologic feature of increased ATX expression is pulmonary fibrosis, renal fibrosis, or liver fibrosis.

The present disclosure also provides use of the above compound having the structure of Formula I', Formula I, Formula I-1, Formula II, Formula II-1, Formula III or Formula III-1 or the pharmaceutically acceptable salt, ester, isomer, solvate, prodrug or isotopically labelled compound thereof, or the above pharmaceutical composition or pharmaceutical formulation, in preparation of a drug for preventing and/or treating a related disease with a pathologic feature of increased ATX expression; preferably, the related disease with the pathologic feature of increased ATX expression includes cancer, fibrotic diseases, metabolic diseases, myelodysplastic syndrome, respiratory diseases, cardiovascular diseases, autoimmune diseases, inflammation, dermatological diseases, nervous system diseases or pain; more preferably, the related disease with the pathological feature of increased ATX expression is pulmonary fibrosis, renal fibrosis, or liver fibrosis.

The present disclosure also provides a method for preventing and/or treating a related disease with a pathologic feature of increased ATX expression, comprising the step of administering a therapeutically effective amount of the above compound having the structure of Formula I', Formula I, Formula I-1, Formula II, Formula II-1, Formula III or Formula III-1 or the pharmaceutically acceptable salt, ester, isomer, solvate, prodrug or isotopically labelled compound thereof, or the above pharmaceutical composition or pharmaceutical formulation, to a subject in need thereof.

Advantageous Effects of the Disclosure

Compared with the existing ATX inhibitor GLPG-1690, the compound of the present disclosure has higher inhibitory activity while exhibiting excellent efficacy, in vitro/in vivo pharmacokinetic properties and safety, thus having promising prospects in clinical application.

DETAILED DESCRIPTION

Before the present disclosure is further described, it should be understood that the present disclosure is not limited to particular embodiments described herein; and it should also be understood that the terms used herein are only for description but not limiting the particular embodiments.

Definition of Terms

Unless otherwise stated, the following terms have the following meanings.

The term "$C_{1-6}$ alkyl" alone or in combination represents a saturated linear or branched alkyl group having 1 to 6 carbon atoms, in particular 1 to 4 carbon atoms, including methyl, ethyl, propyl, isopropyl, butyl, sec-butyl, isobutyl, tert-butyl, n-amyl, 2-amyl, 3-amyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, etc. Preferably, "$C_{1-6}$ alkyl" is any one of methyl, ethyl, isopropyl and tert-butyl.

The term "$C_{1-3}$ alkylene" alone or in combination represents a saturated linear or branched alkylene group having 1 to 3 carbon atoms, including methylene ($-CH_2-$), ethylene ($-CH_2CH_2-$), n-propylene ($-CH_2CH_2CH_2-$), isopropylene ($-(CH_3)_2C-$), etc.

The term "$C_{3-7}$ cycloalkyl" alone or in combination represents a saturated cycloalkyl group having 3 to 7 carbon atoms, especially 3 to 6 carbon atoms, including cyclopropyl, cyclobutyl, cyclopentyl, cyclohexyl, cycloheptyl, etc. Particularly, "$C_{3-7}$ cycloalkyl" is cyclopropyl, cyclopentyl, cyclohexyl, etc.

The term "$C_{1-6}$ alkoxy" alone or in combination represents the group $C_{1-6}$ alkyl-O—, wherein "$C_{1-6}$ alkyl" is as defined above.

The term "halogen" alone or in combination represents fluorine, chlorine, bromine or iodine, in particular fluorine, chlorine or bromine.

The term "amino" alone or in combination represents a primary amino group ($-NH_2$), a secondary amino group (—NH—) or a tertiary amino group (  ).

The term "$C_{1-6}$ alkylamino", also known as "$C_{1-6}$ alkyl amino", alone or in combination represents an "amino" as defined above, wherein the hydrogen atom in the amino is substituted with at least one $C_{1-6}$ alkyl, wherein "$C_{1-6}$ alkyl" is as defined above. Accordingly, "$C_{1-6}$ alkylamino" includes methylamino, ethylamino, propylamino, isopropylamino, n-butylamino, isobutylamino, 2-butylamino, tert-butylamino, n-pentylamino, 2-pentylamino, 3-pentylamino, 2-methyl-2-butylamino, 3-methyl-2-butylamino, 3-methyl-1-butylamino, 2-methyl-1-butylamino, n-hexylamino, 2-hexylamino, 3-hexylamino, 2-methyl-2-pentylamino, 3-methyl-2-pentylamino, 4-methyl-2-pentylamino, 3-methyl-3-pentylamino, 2-methyl-3-pentylamino, 2,3-dimethyl-2-butylamino, 3,3-dimethyl-2-butylamino, and the like. Particularly, "$C_{1-6}$ alkylamino" is methylamino, ethylamino, isopropylamino, tert-butylamino, etc. In the present disclosure, the $C_{1-6}$ alkylamino can be further optionally substituted with a common substituent in the art.

The term "carbonyl", also known as "—C(═O)—", refers to a divalent group, which is composed only of one carbon atom and one oxygen atom which are connected by a double bond, and the carbon atom in its own structure is also connected to other two fragments by single bonds.

The term "heterocycloalkyl", also known as "heterocyclic group", refers to a saturated or partially unsaturated (containing 1 or 2 double bonds) non-aromatic cyclic group consisting of carbon atom and heteroatom such as nitrogen, oxygen or sulfur, the cyclic group can be a monocyclic or bicyclic group, and the heterocycloalkyl group herein has 2-11 carbon atoms, and preferably has 1, 2, 3 or 4 heteroatoms, and the nitrogen, carbon or sulfur atom in the heterocycloalkyl group can be optionally oxidized. A hydrogen atom in the "heterocycloalkyl" group is independently and optionally substituted with one or more substituents as described herein. "Heterocycloalkyl" can be linked to a parent molecule by any ring atom of the ring. The terms "3- to 6-membered heterocycloalkyl" and "3- to 7-membered heterocycloalkyl" refer to saturated or partially unsaturated monocyclic or polycyclic heterocycloalkyl groups, which contain 3 to 6 and 3 to 7 carbon atom(s) and heteroatom(s) or heteroatomic group(s), respectively, the heteroatom or heteroatomic group being selected from the group consisting of N, O, and $S(O)_m$ (where m is any integer from 0 to 2); for example aziridinyl, azetidinyl, oxetanyl, pyrrolidinyl, oxopyrrolidinyl, tetrahydrofuranyl, tetrahydrothienyl, piperidinyl, morpholinyl, piperazinyl, thiomorpholinyl, tetrahydropyranyl, 1,1-dioxidothiomorpholinyl, and

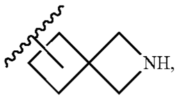

etc.

The term "aryl" represents any stable 6- to 10-membered monocyclic or bicyclic aromatic group, including phenyl, naphthyl, tetrahydronaphthyl, 2,3-dihydroindenyl or biphenyl. A hydrogen atom in the "aryl" group is independently and optionally substituted with one or more substituents as described herein.

The term "heteroaryl" represents an aromatic ring group formed by replacing a carbon atom of a ring with at least one heteroatom selected from the group consisting of sulfur, oxygen, and nitrogen, the aromatic ring group can be a 5- to 7-membered monocyclic group or a 7- to 12-membered bicyclic group. Preferably, the heteroaryl group herein has 1, 2, 3 or 4 heteroatoms, such as thienyl, pyridinyl, pyrimidinyl, pyrazinyl, pyridazinyl, 2-oxopyridin-1(2H)-yl, 4-oxopyridin-1(4H)-yl, pyrrolyl, pyrazolyl, thiazolyl, 1,2,3-triazolyl, 1,2,4-triazolyl, imidazolyl, tetrazolyl, isothiazolyl, oxazolyl, isoxazolyl, thiadiazolyl, oxadiazolyl, naphthyl, benzothiophenyl, indolyl, benzimidazolyl, benzothiazolyl, benzofuranyl, quinolinyl, isoquinolinyl, or quinazolinyl. A hydrogen atom in the "heteroaryl" group is independently and optionally substituted with one or more substituents as described herein.

The term "$C_{6-10}$ aryl" represents an aryl group having 6 to 10 carbon atoms, wherein "aryl" is as defined above.

The term "5- to 10-membered heteroaryl" represents a heteroaryl group having 5 to 10 atoms, wherein "heteroaryl" is as defined above.

The term "cyano" alone or in combination represents the group —CN.

The term "carboxyl" alone or in combination represents the group —COOH.

The term "hydroxyl" alone or in combination represents the group —OH.

The term "stereoisomer" encompasses all forms of isomerism, including an enantiomer, a diastereomer and a geometric isomer (cis-trans isomer). Thus, individual stereochemical isomers of the compound designed in the present disclosure or a mixture of its enantiomer(s), diastereomer(s), or geometric isomer(s) (or cis-trans isomer(s)) will fall within the scope of the present disclosure.

The term "pharmaceutically acceptable salt" means that the compound of the present disclosure is present in the form of its pharmaceutically useful salts, including an acid addition salt and a base addition salt. A pharmaceutically acceptable non-toxic acid addition salt herein means a salt formed by the compound of the present disclosure and an organic or inorganic acid. The organic or inorganic acid includes, but is not limited to, hydrochloric acid, sulfuric acid, hydrobromic acid, hydroionic acid, phosphoric acid, nitric acid, perchloric acid, acetic acid, oxalic acid, maleic acid, fumaric acid, tartaric acid, benzenesulfonic acid, mesylic acid, salicylic acid, succinic acid, citric acid, lactic acid, propionic acid, benzoic acid, p-toluenesulfonic acid, malic acid, etc. A pharmaceutically acceptable non-toxic base addition salt means a salt formed by the compound of the present disclosure and an organic or inorganic base, which includes, but is not limited to, an alkali metal salt, such as a lithium, sodium or potassium salt; a alkaline earth metal salt, such as a calcium or magnesium salt; an organic base salt, such as an ammonium salt or $N^+(C_{1-6}\ alkyl)_4$ salt formed by reacting with an N group-containing organic base.

The term "solvate" means an association complex formed by one or more solvent molecules and the compound of the present disclosure. A solvent forming the solvate includes, but is not limited to, water, methanol, ethanol, isopropanol, ethyl acetate, tetrahydrofuran, N,N-dimethylformamide, dimethyl sulfoxide, etc.

The term "hydrate" refers to an association complex formed by water and the compound of the present disclosure.

The term "prodrug" means a chemical derivative of the compound of the present disclosure, which is converted into the compound shown in Formula I by a chemical reaction in vivo.

The term "isotope derivative" means an isotope derivative obtained by replacing the hydrogen atom in Formula I with 1 to 6 deuterium atoms, or an isotope derivative obtained by replacing the carbon atom in Formula I with 1 to 3 $^{14}C$ atoms.

The terms related to the present disclosure are as defined above, which can also be understood by those skilled in the art in combination with the prior art, and the present disclosure is further described below based on the contents herein and the definition of terms.

[Compound of General Formula]

A compound having a structure of Formula I' or a pharmaceutically acceptable salt, ester, isomer, solvate, prodrug or isotopically labelled compound thereof,

I'

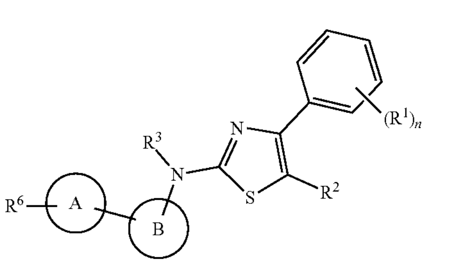

n is any integer from 0 to 5;

if present, each $R^1$ is independently selected from the group consisting of hydrogen, deuterium, cyano, halogen, amino, hydroxyl, —COOH, —CHO, —$NO_2$, $C_{1-6}$ alkylamino, $C_{1-6}$ alkoxy, and $C_{1-6}$ alkyl, $C_{3-7}$ cycloalkyl and 3- to 7-membered heterocycloalkyl that are unsubstituted or substituted with substituents selected from the group consisting of cyano, amino, hydroxyl, halogen, $C_{1-6}$ alkyl, and $C_{1-6}$ alkoxy;

$R^2$ is selected from the group consisting of hydrogen, deuterium, halogen, cyano, amino, hydroxyl, —COOH, —CHO, —$NO_2$, $C_{1-6}$ alkyl, $C_{1-6}$ alkoxy, $C_{1-6}$ alkylamino, —C(═O)$NH_2$, —NH(C═O)$CH_3$, and 3- to 7-membered heterocycloalkyl;

$R^3$ is selected from the group consisting of hydrogen, deuterium, $C_{1-6}$ alkyl, $C_{3-7}$ cycloalkyl, and $C_{1-6}$ alkyl, $C_{3-7}$ cycloalkyl and 3- to 7-membered heterocycloalkyl that are substituted with substituents selected from the group consisting of cyano, amino, hydroxyl, halogen, $C_{1-6}$ alkyl, and $C_{1-6}$ alkoxy;

ring B is any one of the following structures:

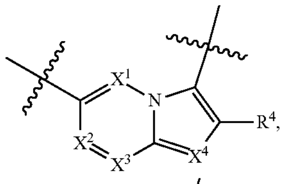

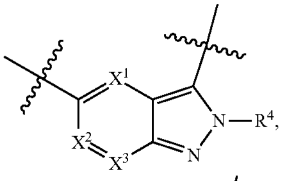

and

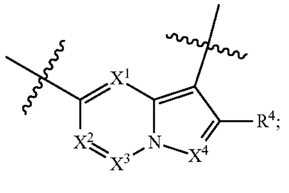

$R^4$ is selected from the group consisting of hydrogen, deuterium, halogen, cyano, hydroxyl, amino, $C_{1-6}$ alkyl, $C_{1-6}$ alkoxy, $C_{1-6}$ alkylamino, $C_{3-7}$ cycloalkyl, and 3- to 7-membered heterocycloalkyl;

$X^1$, $X^2$, $X^3$ and $X^4$ are each independently N or $CR^5$;

$R^5$ is selected from the group consisting of hydrogen, deuterium, halogen, $C_{1-6}$ alkyl, and $C_{1-6}$ alkyl, $C_{3-7}$ cycloalkyl and 3- to 7-membered heterocycloalkyl that are substituted with substituents selected from the group consisting of cyano, amino, hydroxyl, halogen, $C_{1-6}$ alkyl, and $C_{1-6}$ alkoxy;

ring A is selected from the group consisting of $C_{6-10}$ aryl and 5- to 10-membered heteroaryl that are substituted or unsubstituted, and the substitution is a substitution with 1 to 3 substituents selected from the group consisting of hydroxyl, amino, halogen, cyano, $C_{1-6}$ alkyl, $C_{1-6}$ haloalkyl, $C_{3-7}$ cycloalkyl, 3- to 7-membered heterocycloalkyl, $C_{1-6}$ alkylamino, and $C_{1-6}$ alkoxy;

$R^6$ is -$L^1$-$L^2$-$W^1$;

$L^1$ is selected from the group consisting of a chemical bond, $C_{1-3}$ alkylene, —O—, —C(═O)—, —C(═O)C(R')$_2$—, —C(═O)O—, —C(═O)NH—, —OC(═O)—, —NH—, —$SO_2$—, —NHSO$_2$—, and —$SO_2$NH—; wherein $R^8$ is hydrogen or $C_{1-6}$ alkyl;

$L^2$ is selected from the group consisting of a chemical bond, —O—, —C(═O)—, —C(═O)$CH_2$—, —C(═O)O—, —OC(═O)—, —C(═O)NH—, —$NR^7$—, —NH$CH_2$—, —$SO_2$—, —$NR^7SO_2$—, —$SO_2NR^7$—, —C(═O)$NR^7$—, and —$NR^7$C(═O)—; wherein $R^7$ is hydrogen or $C_{1-6}$ alkyl;

$W^1$ is a substituted or unsubstituted group as follows: hydrogen, deuterium, amino, cyano, $C_{1-6}$ alkyl, halogen, hydroxyl, $C_{1-6}$ alkoxy, $C_{1-6}$ alkylamino, carboxyl, $C_{6-10}$ aryl, 5- to 10-membered heteroaryl, $C_{3-7}$ cycloalkyl or 3- to 7-membered heterocycloalkyl; the substitution is a substitution with 1 or 2 substituents selected from the group consisting of oxo, hydroxy, amino, hydroxymethyl, aminomethyl, cyano, $C_{1-6}$ alkyl, $C_{1-6}$ alkyl-C(═O)O—, and halogen.

In some preferred embodiments of the present disclosure, n is any integer from 0 to 2, preferably n is 1; if present, each $R^1$ is independently selected from the group consisting of hydrogen, cyano and halogen, preferably halogen, more preferably fluorine.

In some preferred embodiments of the present disclosure, $R^2$ is cyano.

In some preferred embodiments of the present disclosure, $R^3$ is $C_{1-6}$ alkyl, preferably methyl or ethyl.

In some preferred embodiments of the present disclosure, $R^4$ is selected from the group consisting of hydrogen, deuterium, methyl, ethyl, isopropyl and cyclopropyl, preferably ethyl.

In some preferred embodiments of the present disclosure, $X^1$, $X^2$, $X^3$ and $X^4$ are each independently N or $CR^5$, and $R^5$ is selected from the group consisting of hydrogen, deuterium, halogen, methyl and halomethyl, preferably hydrogen.

In some preferred embodiments of the present disclosure, ring A is selected from the group consisting of phenylene, pyridinylene, pyrazinylene, pyridazinylene, pyrimidinylene, pyrazolylene, imidazolylene, oxazolylene, isoxazolylene, thiazolylene, thiadiazolylene, and oxadiazolylene.

In some more preferred embodiments of the present disclosure, ring A is any one selected from the following structures:

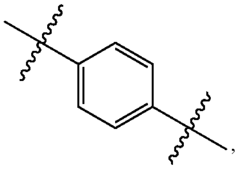,

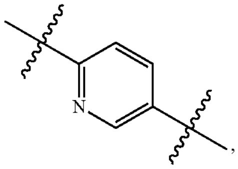,

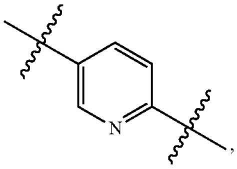,

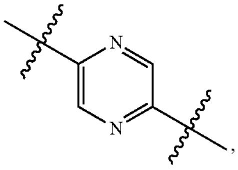,

-continued

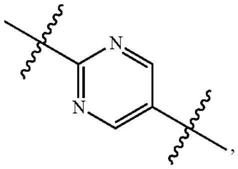, 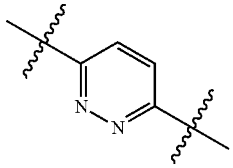,

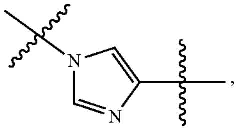, 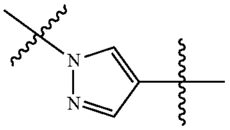,

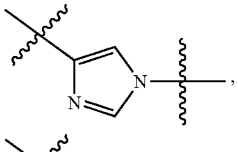, 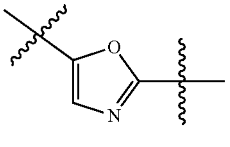,

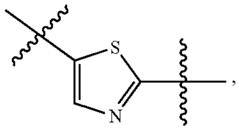, 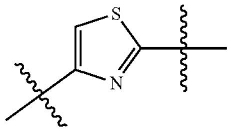,

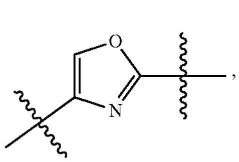, 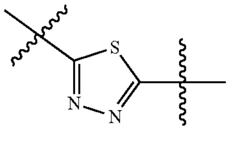,

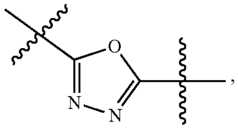, 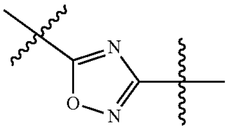,

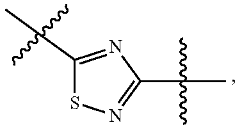, 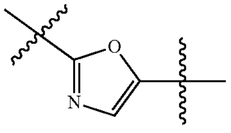,

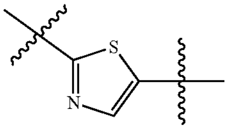, 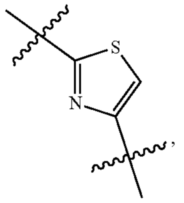, and

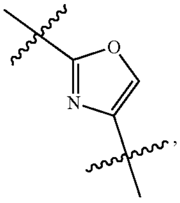, preferably, any one selected from the following structures:

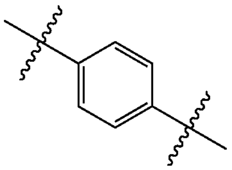, 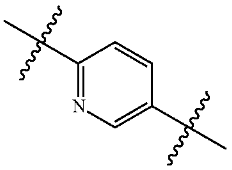,

-continued

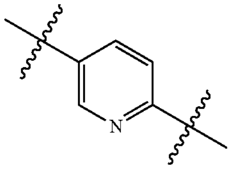, 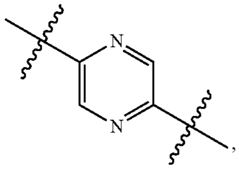,

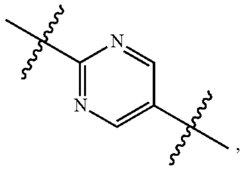, and 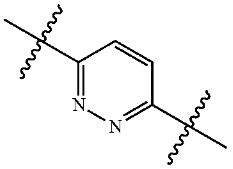.

In some preferred embodiments of the present disclosure, ring A is substituted with 1 to 3 substituents, preferably 1 substituent, the substituents are each independently selected from the group consisting of hydroxyl, amino, halogen, cyano and $C_{1-6}$ alkyl, preferably halogen and $C_{1-6}$ alkyl, more preferably fluorine and methyl.

In some preferred embodiments of the present disclosure, $L^1$ is selected from the group consisting of a chemical bond, $—CH_2—$, $—CH(CH_3)—$, $—C(CH_3)_2—$, $—C(=O)—$, $—SO_2—$, $—C(=O)CH_2—$ and $—C(=O)NH—$, preferably the chemical bond, $—CH_2—$, $—C(CH_3)_2—$, and $—C(=O)CH_2—$.

In some preferred embodiments of the present disclosure, $L^2$ is selected from the group consisting of a chemical bond, $—NH—$, $—C(=O)—$, $—SO_2—$, $—NHCH_2—$, $—C(=O)CH_2—$, $—C(=O)NH—$, $—NHSO_2—$ and $—N(CH_3)SO_2—$, preferably the chemical bond, $—C(=O)—$, $—NHCH_2—$, $—C(=O)NH—$, $—NHSO_2—$, and $—N(CH_3)SO_2—$.

In some preferred embodiments of the present disclosure, $W^1$ is a substituted or unsubstituted group as follows: $C_{1-6}$ alkyl, $C_{6-10}$ aryl, 5- to 10-membered heteroaryl, $C_{3-7}$ cycloalkyl or 3- to 7-membered heterocycloalkyl, and the substitution is a substitution with 1 or 2 substituents selected from the group consisting of oxo, hydroxy, amino, hydroxymethyl, aminomethyl, halogen, cyano, $C_{1-6}$ alkyl-C(=O)O—, and $C_{1-6}$ alkyl.

In some more preferred embodiments of the present disclosure, $W^1$ is $C_{1-6}$ alkyl, $C_{3-7}$ cycloalkyl or 3- to 7-membered heterocycloalkyl which is unsubstituted or substituted with 1 or 2 substituents selected from the group consisting of hydroxy, amino, hydroxymethyl, aminomethyl and $C_{1-6}$ alkyl-C(=O)O—.

In some more preferred embodiments of the present disclosure, $W^1$ is a group as follows: methyl, ethyl, n-propyl, isopropyl, cyclopropyl, cyclobutyl, cyclopentyl, cyclohexyl, aziridinyl, azetidinyl, pyrrolidinyl, oxopyrrolidinyl, piperidinyl, piperazinyl, morpholinyl, thiomorpholinyl, oxetanyl, tetrahydrofuranyl, tetrahydrothienyl, tetrahydropyranyl, 1,1-dioxidothiomorpholinyl, 2-azaspiro[3.3]heptyl, 1,1-dioxidoisothiazolidinyl, or 1,1-dioxido-1,2-thiazinanyl which is unsubstituted or substituted with 1 or 2 substituents selected from the group consisting of hydroxy, amino, hydroxymethyl, aminomethyl, and acetoxy, preferably methyl, oxopyrrolidinyl, 2-azaspiro[3.3]heptyl, 1,1-dioxido-isothiazolidinyl, or 1,1-dioxido-1,2-thiazinanyl, or preferably ethyl, azetidinyl, cyclobutyl, pyrrolidinyl, or piperidinyl which is substituted by a substituent selected from the group consisting of hydroxyl, hydroxymethyl, and acetoxy.

In some preferred embodiments of the present disclosure, in the compound of Formula I', n is 1;

$R^1$ is fluorine;

$R^2$ is cyano;

$R^3$ is methyl or ethyl;

ring B is any one of the following structures:

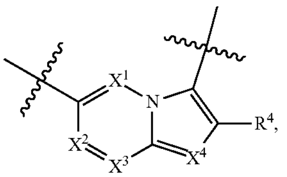

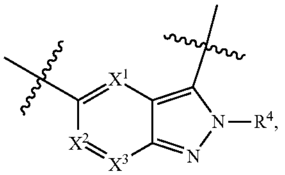

and

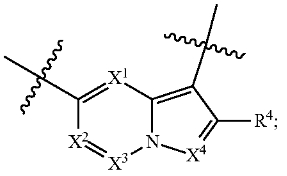

$R^4$ is ethyl;

$X^1$, $X^2$, $X^3$ and $X^4$ are each independently N or CH;

ring A is any one selected from the following structures;

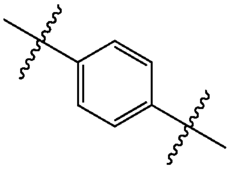

,

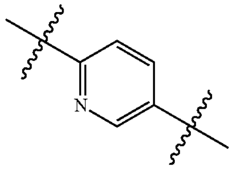

,

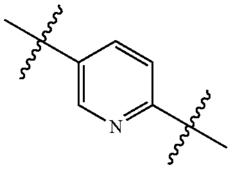

,

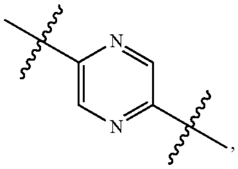

,

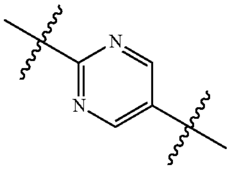

, and

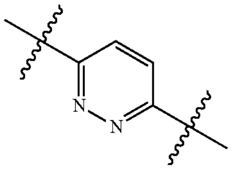

, ring A is unsubstituted or substituted with one fluorine or methyl;

$R^6$ is $-L^1-L^2-W^1$;

$L^1$ is selected from the group consisting of a chemical bond, $-CH_2-$, $-C(CH_3)_2-$, and $-C(=O)CH_2-$;

$L^2$ is selected from the group consisting of a chemical bond, $-C(=O)-$, $-NHCH_2-$, $-C(=O)NH-$, $-NHSO_2-$, and $-N(CH_3)SO_2-$;

$W^1$ is any one of the following groups:

$CH_3$-,

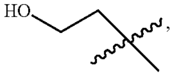

,

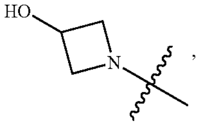

,

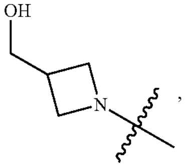

,

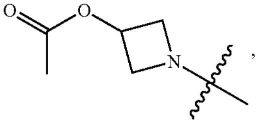

,

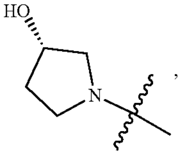

,

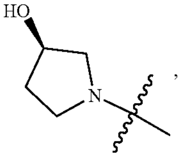

,

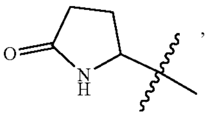

,

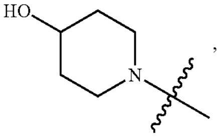

,

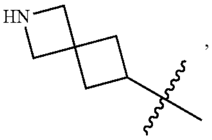

,

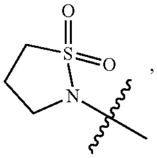

, and

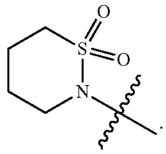

.

In some preferred embodiments of the present disclosure, the above compound of Formula I' is a compound having the structure of Formula I,

I

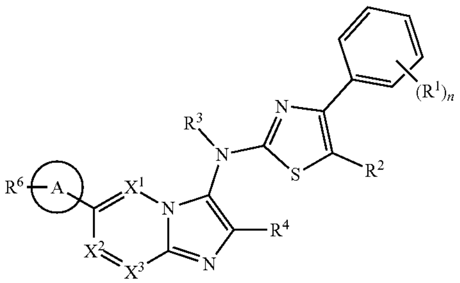

wherein n, $R^1$, $R^2$, $R^3$, $R^4$, $R^6$, $X^1$, $X^2$, $X^3$ and ring A are as defined in Formula I'.

In some more preferred embodiments of the present disclosure, the above compound of Formula I' is a compound having the structure of Formula I-1,

I-1

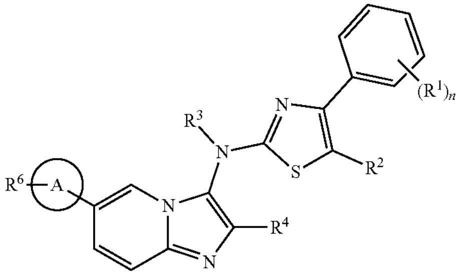

wherein n, $R^1$, $R^2$, $R^3$, $R^4$, $R^6$ and ring A are as defined in Formula I'.

In some preferred embodiments of the present disclosure, the above compound of Formula I' is a compound having the structure of Formula II,

II

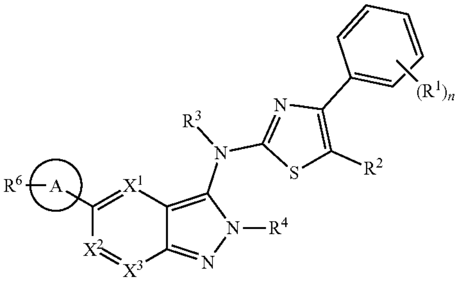

wherein n, $R^1$, $R^2$, $R^3$, $R^4$, $R^6$, $X^1$, $X^2$, $X^3$ and ring A are as defined in Formula I'.

In some more preferred embodiments of the present disclosure, the above compound of Formula I' is a compound having the structure of Formula II-1,

II-1

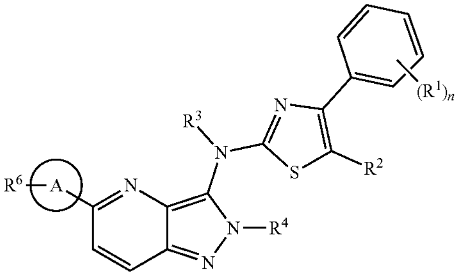

wherein n, $R^1$, $R^2$, $R^3$, $R^4$, $R^6$ and ring A are as defined in Formula I'.

In some preferred embodiments of the present disclosure, the above compound of Formula I' is a compound having the structure of Formula III,

III

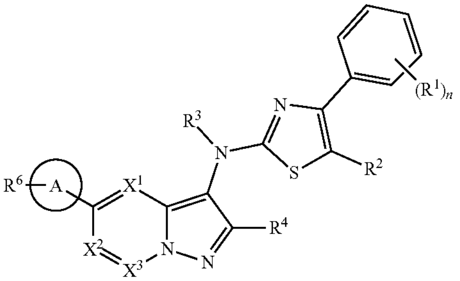

wherein n, $R^1$, $R^2$, $R^3$, $R^4$, $R^6$, $X^1$, $X^2$, $X^3$ and ring A are as defined in Formula I'.

In some more preferred embodiments of the present disclosure, the above compound of Formula I' is a compound having the structure of Formula III-1,

III-1

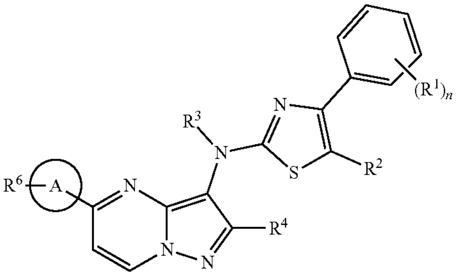

wherein n, $R^1$, $R^2$, $R^3$, $R^4$, $R^6$ and ring A are as defined in Formula I'.

In addition, the following compounds are also provided herein:

1

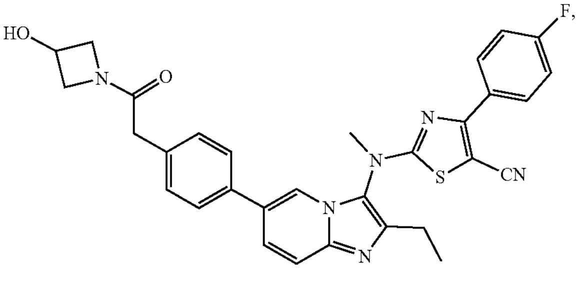

2

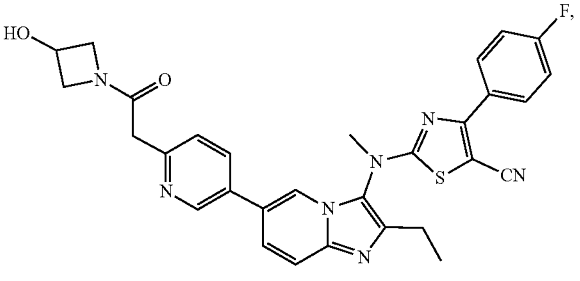

-continued
3
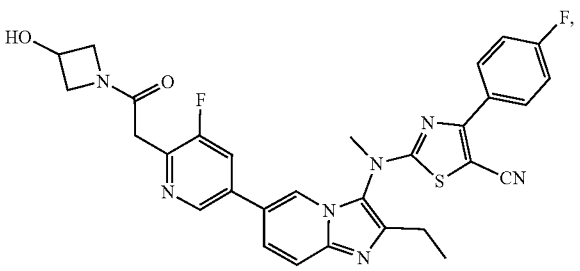
4
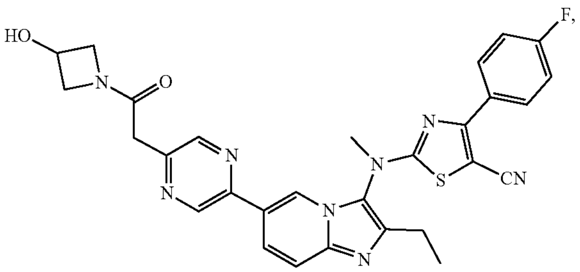
5
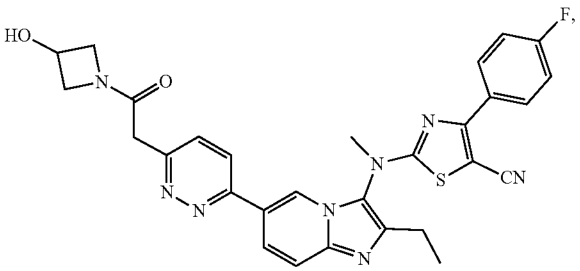
6
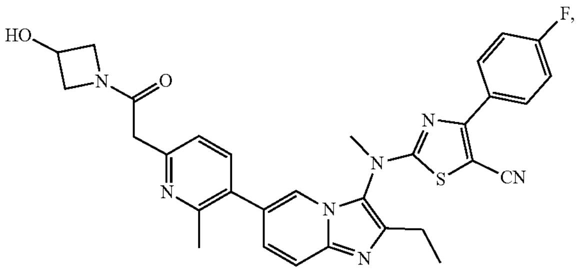
7
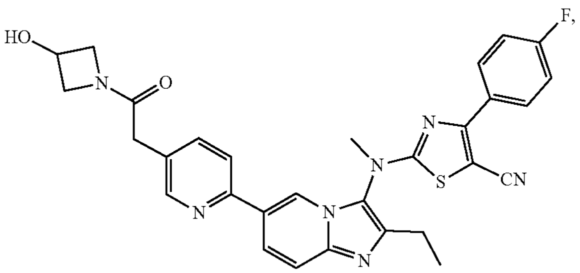
-continued
8
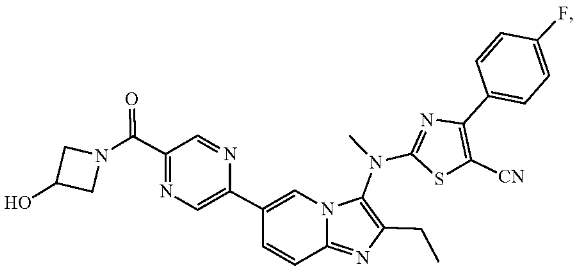
9
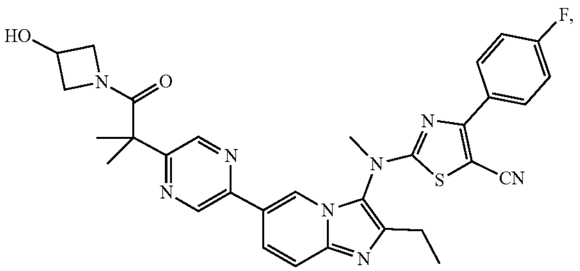
10
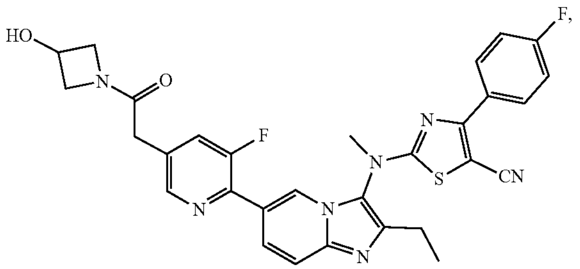
11
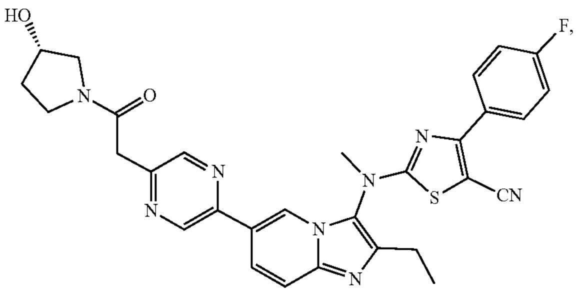
12
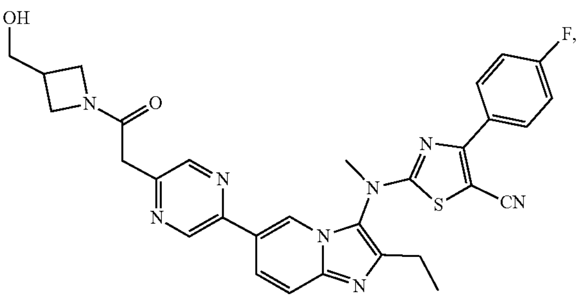

-continued
13
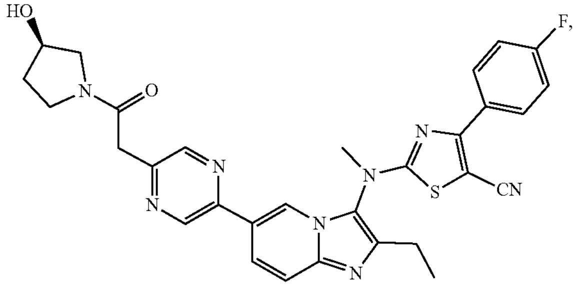
14
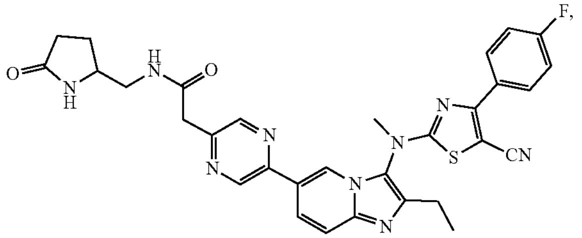
15
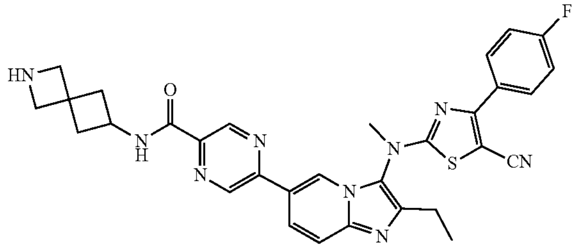
16
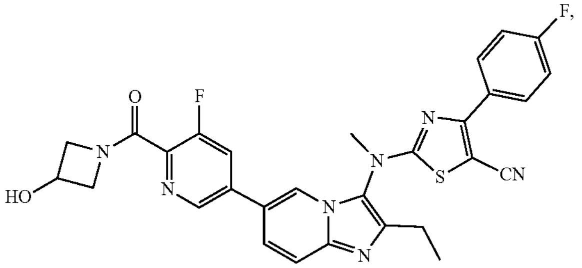
17
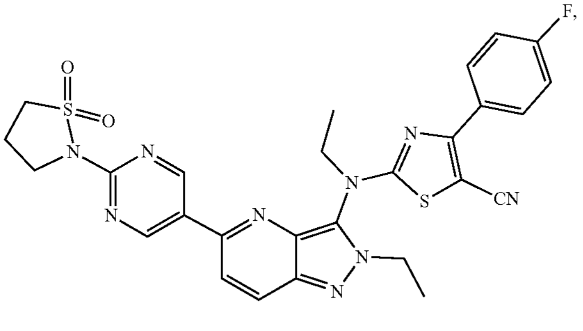
-continued
18
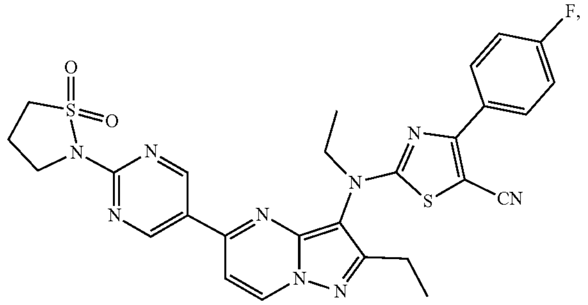
19
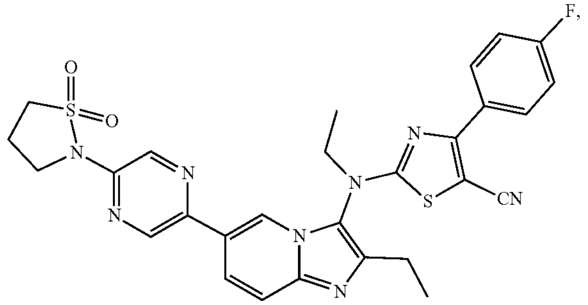
20
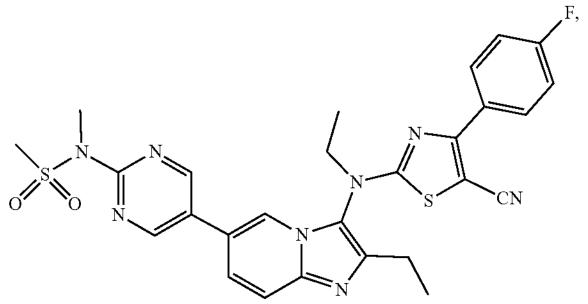
21
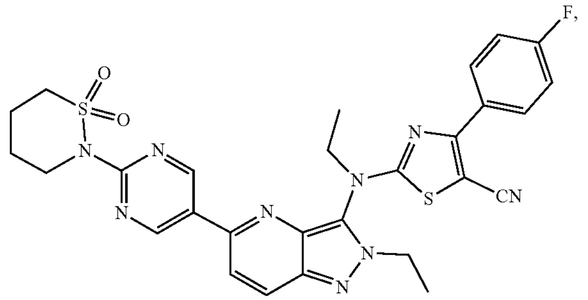
22
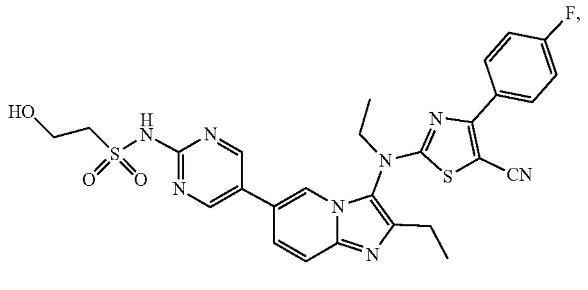

-continued

23

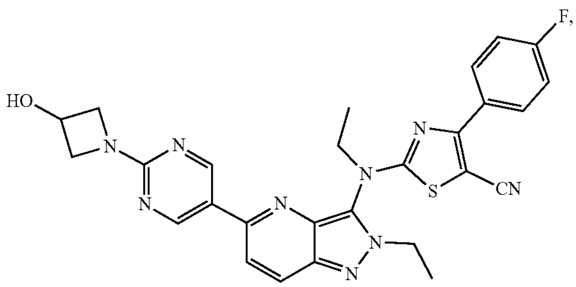

,

24

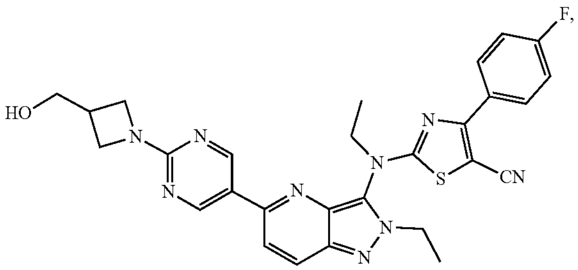

,

25

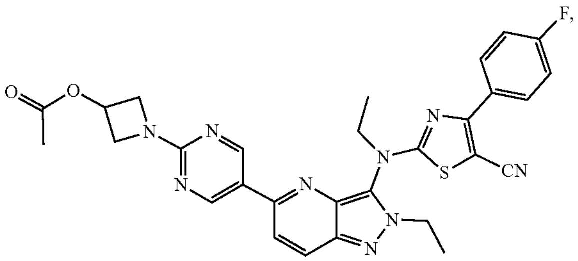

,

26

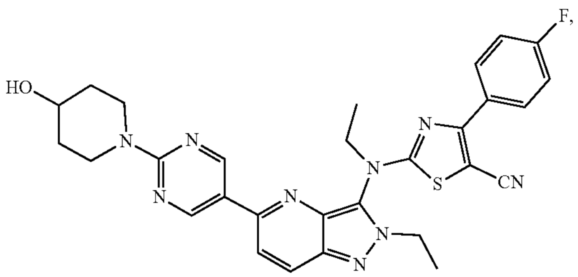

,

27

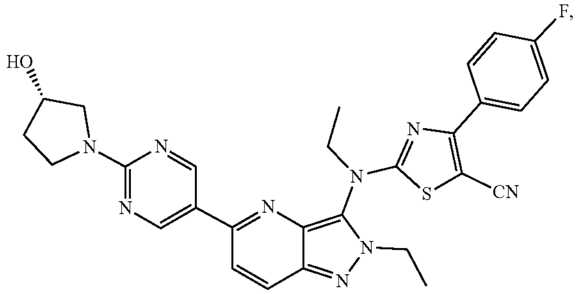

,

-continued

28

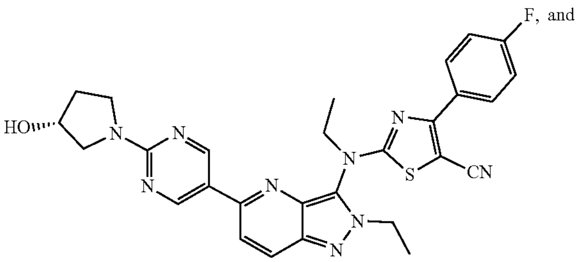

, and

29

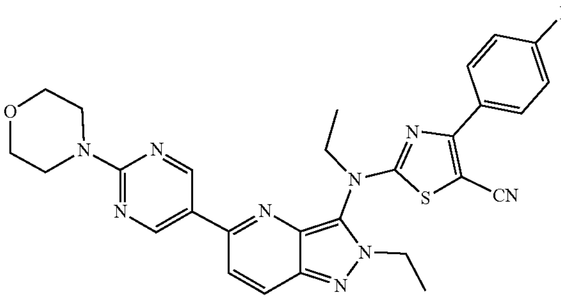

.

[Preparation Method]

The present disclosure also provides a typical synthesis method for the above compound of Formula I to further describe the technical solution of the present disclosure. The synthesis method comprises the following steps:

step 1: reacting compound 1 with a corresponding aldehyde and 1,1,3,3-tetramethylbutyl isocyanide under the catalysis of magnesium chloride to afford intermediate 2;

step 2: deprotecting the intermediate 2 by heating in formic acid to obtain intermediate 3;

step 3: optionally, performing nucleophilic substitution reaction between the intermediate 3 and a corresponding halohydrocarbon to obtain intermediate 4;

step 4: hydrolyzing the intermediate 4 to obtain intermediate 5;

step 5: performing nucleophilic substitution reaction between the intermediate 5 and intermediate 6 under alkaline conditions to obtain intermediate 7;

wherein the intermediate 6 is prepared from compound 11 by a two-step reaction: firstly, intermediate 12 is obtained by ring-closing reaction between the compound 11 and thiourea; then the intermediate 12 reacts in the presence of tert-butyl nitrite and copper chloride to obtain the intermediate 6;

step 6: performing Suzuki coupling reaction between the intermediate 7 and intermediate 10 to obtain intermediate 8;

as another alternative technical solution, the intermediate 8 can also be prepared by affording intermediate 13 from the intermediate 7 followed by Suzuki reaction between the intermediate 13 and intermediate 14 (X can be Cl, Br, or I);

step 7, hydrolyzing the intermediate 8 to obtain intermediate 9;

step 8: performing condensation reaction between the intermediate 9 and an amine to obtain the compound of Formula I, or a tert-butyloxycarboryl protected derivative of the compound of Formula I, which is further deprotected in the presence of trifluoroacetic acid to obtain the compound of Formula I.

The synthetic route is as follows:
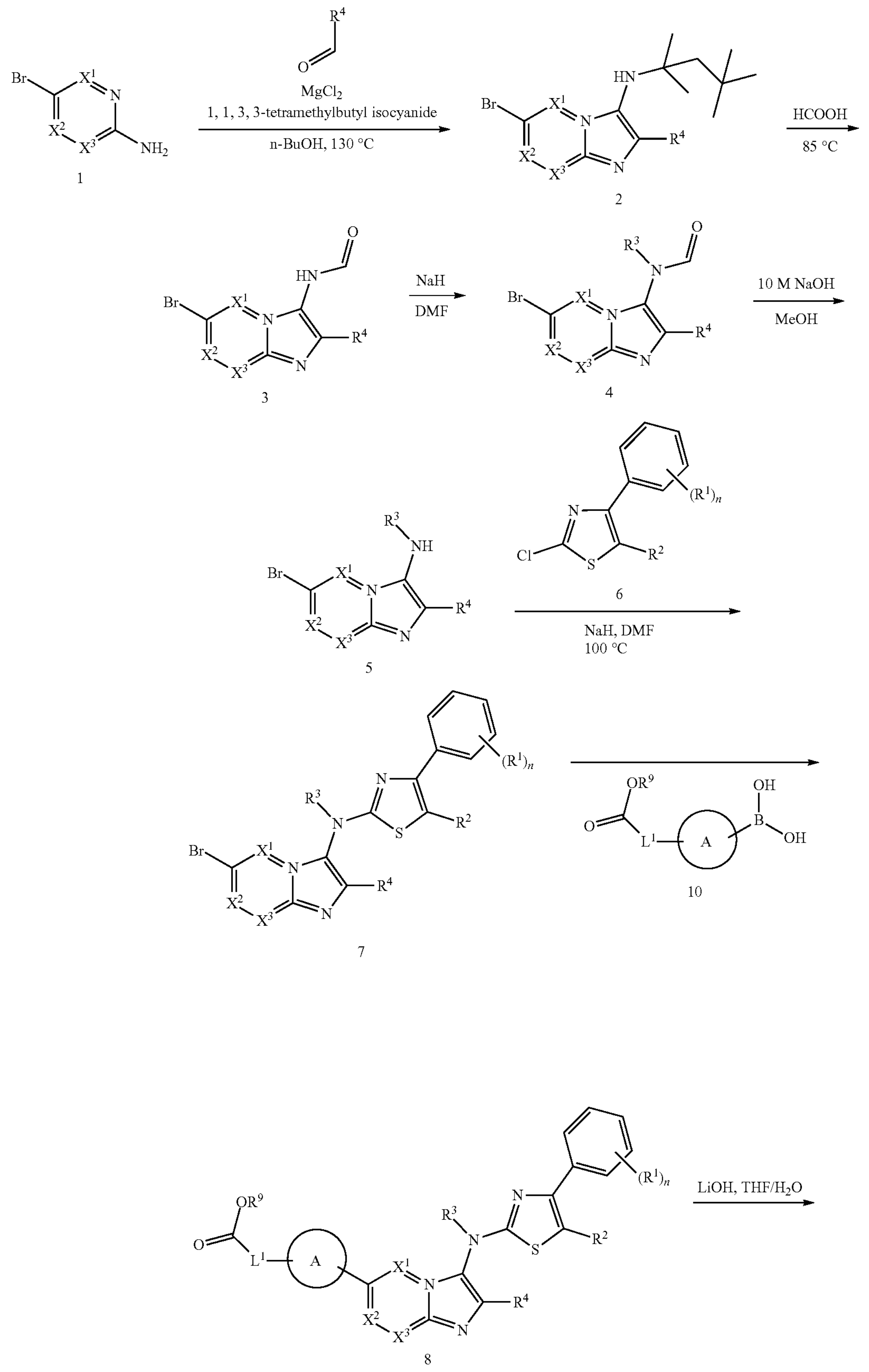
1
2
3
4
5
6
7
10
8

-continued
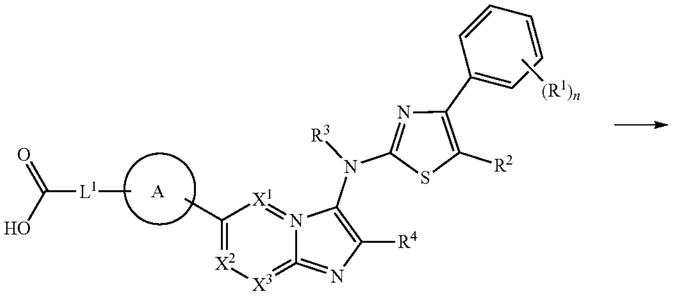
9
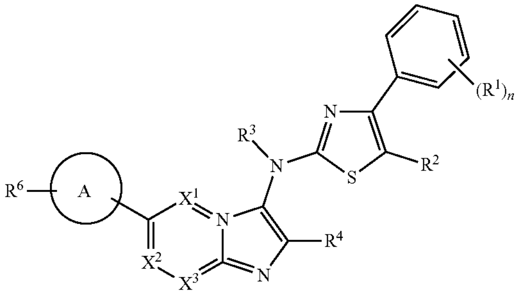
1
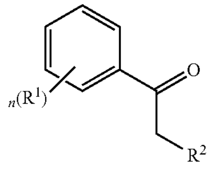
11
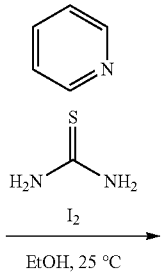
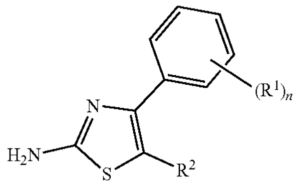
12
t-BuONO
$CuCl_2$, MeCN
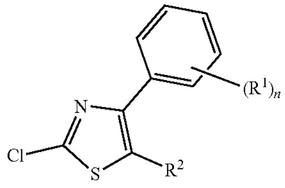
6
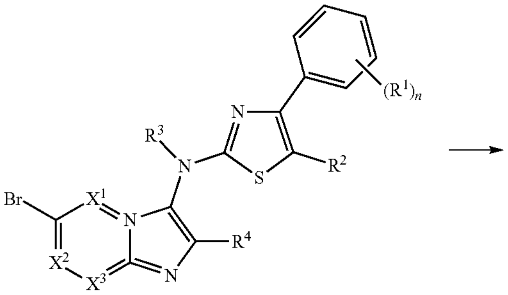
7
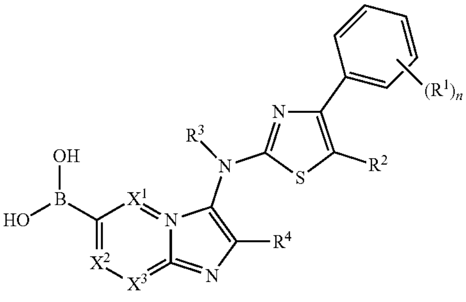
13
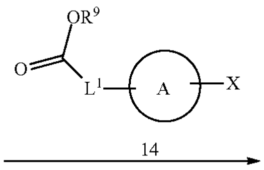
14

-continued

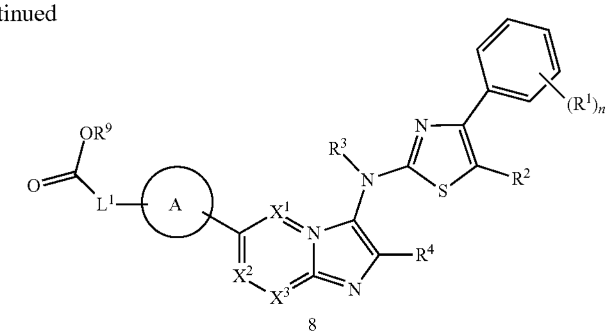

8 wherein the definitions of $R^1$-$R^6$, $X^1$—$X^3$, $L^1$, n and A are the same as above, and $R^9$ is methyl or ethyl.

The present disclosure also provides a typical synthesis method for the compound of Formula II (where $X^1$ is N) to further describe the technical solution of the present disclosure.

The synthesis method comprises the following steps:

step 1: reacting compound 1 with hydrogen peroxide in trifluoroacetic acid solution to afford intermediate 2;

step 2: reacting the intermediate 2 with trimethylcyanosilane under alkaline conditions to obtain intermediate 3;

step 3: optionally, performing ring-closing reaction between the intermediate 3 and a corresponding substituted hydrazine under alkaline conditions to obtain intermediate 4;

step 4: performing nucleophilic substitution reaction between the intermediate 4 and intermediate 12 under alkaline conditions to obtain intermediate 5;

wherein the intermediate 12 is prepared from compound 10 by a two-step reaction: firstly, intermediate 11 is obtained by ring-closing reaction between compound 10 and thiourea; then the intermediate 11 reacts in the presence of tert-butyl nitrite and copper chloride to obtain the intermediate 12;

step 5: performing nucleophilic substitution on intermediate 5 and a corresponding halohydrocarbon to obtain intermediate 6;

step 6: performing Suzuki coupling reaction between the intermediate 6 and intermediate 9 to obtain the compound of Formula II, or a tert-butyloxycarboryl protected derivative of the compound of Formula II, which is further deprotected in the presence of trifluoroacetic acid to obtain the compound of Formula II;

wherein the intermediate 9 is prepared from compound 7 by a two-step reaction: firstly, intermediate 8 is obtained by nucleophilic substitution between compound 7 and a corresponding amine; then the intermediate 8 reacts in the presence of a catalyst to obtain the intermediate 9 as a boronic acid reagent.

The synthetic route is as follows:

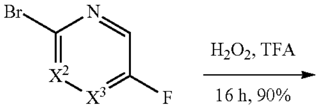

1

-continued

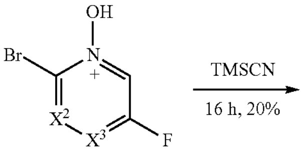

2

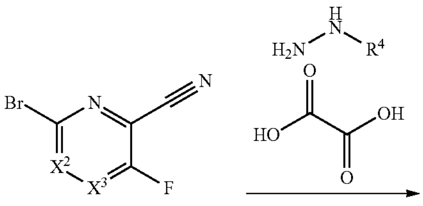

3

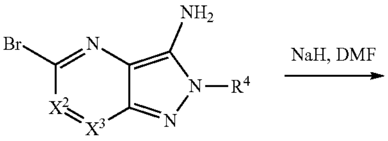

4

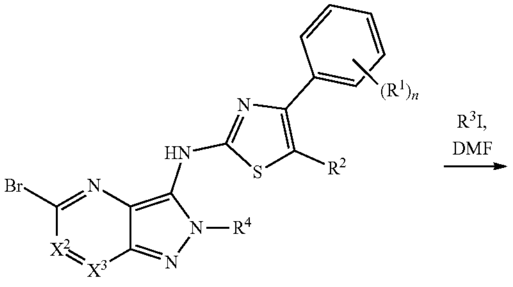

5

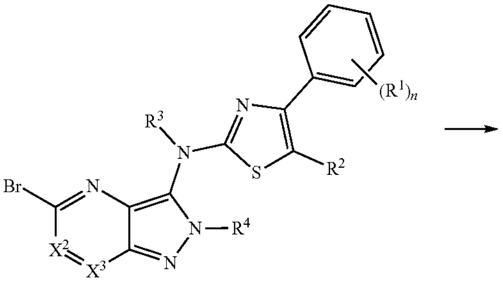

6

-continued

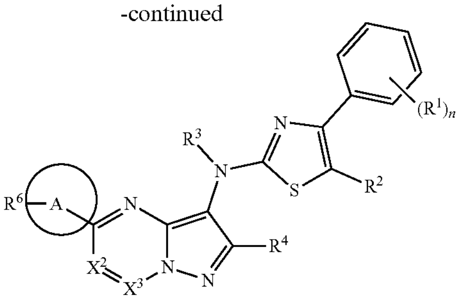

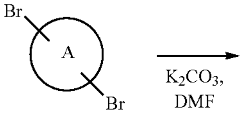

7

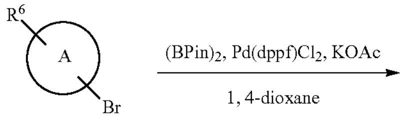

8

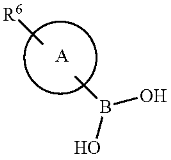

9

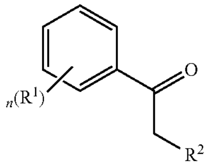

10

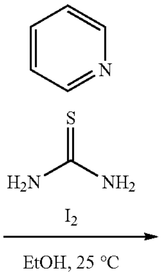

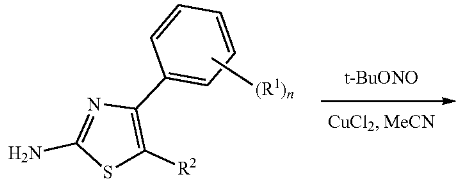

11

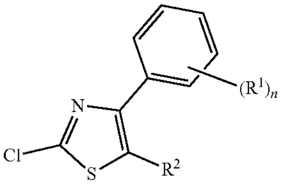

12 wherein the definitions of $R^1$-$R^6$, $X^2$-$X^3$, n and A are the same as above.

The present disclosure also provides a typical synthesis method for the compound of Formula III (where $X^1$ is N) to further describe the technical solution of the present disclosure.

The synthesis method comprises the following steps:

step 1: performing close-ring reaction between compound 1 and compound 2 under alkaline conditions to afford intermediate 3;

step 2: performing nitration reaction on the intermediate 3 to obtain intermediate 4;

step 3: performing chlorination reaction on the intermediate 4 in the presence of phosphorus oxychloride to obtain intermediate 5;

step 4: reducing the intermediate 5 to obtain intermediate 6;

step 5: performing nucleophilic substitution reaction between the intermediate 6 and intermediate 14 under alkaline conditions to obtain intermediate 7;

wherein the intermediate 14 is prepared from compound 12 by a two-step reaction: firstly, intermediate 13 is obtained by ring-closing reaction between the compound 12 and thiourea; then the intermediate 13 reacts in the presence of tert-butyl nitrite and copper chloride to obtain the intermediate 14;

step 6: performing nucleophilic substitution between the intermediate 7 and a corresponding halohydrocarbon to obtain intermediate 8;

step 7: performing Suzuki coupling reaction between the intermediate 8 and intermediate 11 to obtain the compound of Formula III, or a tert-butyloxycarboryl protected derivative of the compound of Formula III, which is further deprotected in the presence of trifluoroacetic acid to obtain the compound of Formula III;

wherein the intermediate 11 is prepared from compound 9 by a two-step reaction: firstly, intermediate 10 is obtained by nucleophilic substitution between the compound 9 and a corresponding amine; then the intermediate 10 reacts in the presence of a catalyst to obtain the intermediate 11 as a boronic acid reagent.

The synthetic route is as follows:

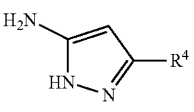

1

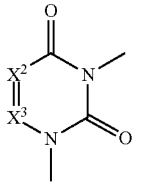

2

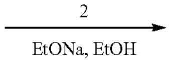

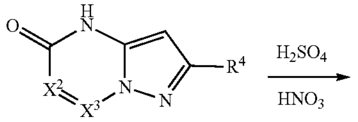

3

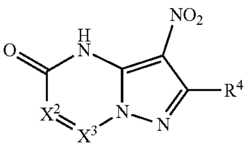

4

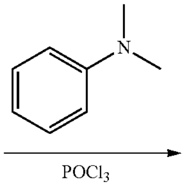

-continued

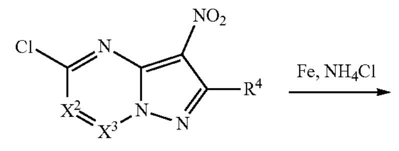

5

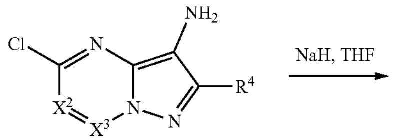

6

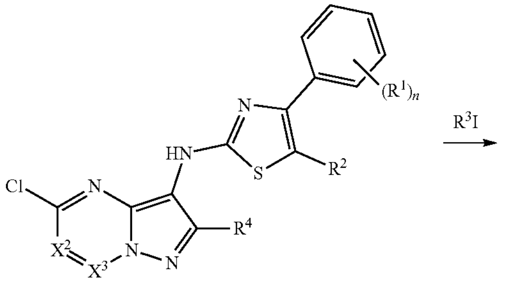

7

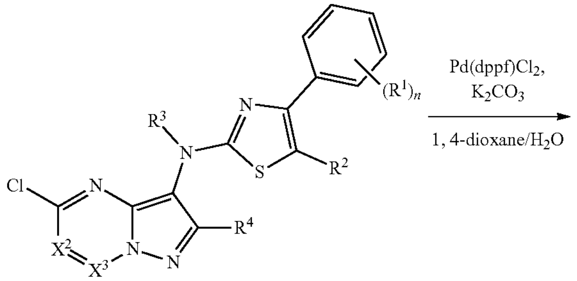

8

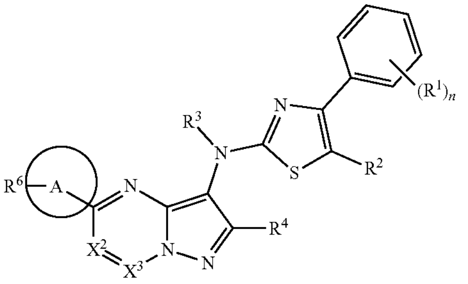

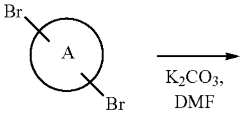

9

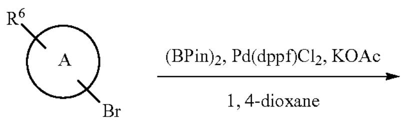

10

-continued

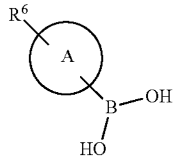

11

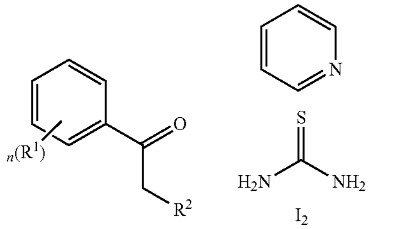

12

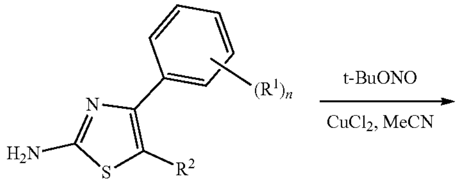

13

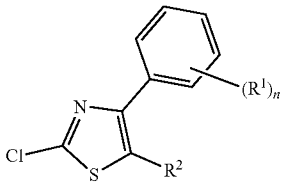

14 wherein the definitions of $R^1$-$R^6$, $X^2$—$X^3$, n and A are the same as above.

[Pharmaceutical Composition]

The term "pharmaceutical composition" refers to a composition that can be used as a drug, comprising an active pharmaceutical ingredient (API) and optionally one or more pharmaceutically acceptable carriers. The term "pharmaceutically acceptable carrier" refers to a pharmaceutical excipient that is compatible with the active pharmaceutical ingredient and is harmless to a testee, including (but not limited to) a diluent (or referred to as a filler), an adhesive, a disintegrant, a lubricant, a wetting agent, a thickener, a glidant, a flavorant, an odorant, a preservative, an antioxidant, a pH adjuster, a solvent, a cosolvent, a surfactant, etc.

The present disclosure provides a pharmaceutical composition, comprising the above compound having the structure of Formula I', Formula I, Formula I-1, Formula II, Formula II-1, Formula III or Formula III-1 or the pharmaceutically acceptable salt, ester, isomer, solvate, prodrug or isotopically labelled compound thereof.

In some embodiments of the present disclosure, the above pharmaceutical composition still comprises a pharmaceutically acceptable carrier.

[Pharmaceutical Formulation]

The present disclosure also provides a pharmaceutical formulation, comprising the above compound having the structure of Formula I', Formula I, Formula I-1, Formula II, Formula II-1, Formula III or Formula III-1 or the pharmaceutically acceptable salt, ester, isomer, solvate, prodrug or isotopically labelled compound thereof or the above pharmaceutical composition thereof, and the formulation is any one of a tablet, a capsule, an injection, a granule, a powder, a suppository, a pill, a cream, a paste, a gel, a pulvis, an oral solution, an inhalant, a suspension, a dry suspension, a patch, and a lotion.

[Medical Use]

Both the above compound having the structure of Formula I', Formula I, Formula I-1, Formula II, Formula II-1, Formula III or Formula III-1 or the pharmaceutically acceptable salt, ester, isomer, solvate, prodrug or isotopically labelled compound thereof and the above pharmaceutical composition or pharmaceutical formulation can be used for preventing and/or treating a related disease with a pathologic feature of increased ATX expression; preferably, the related disease with the pathologic feature of increased ATX expression includes cancer, fibrotic diseases, metabolic diseases, myelodysplastic syndrome, respiratory diseases, cardiovascular diseases, autoimmune diseases, inflammation, dermatological diseases, nervous system diseases or pain; more preferably, the related disease with the pathologic feature of increased ATX expression is pulmonary fibrosis, renal fibrosis, or liver fibrosis.

In addition, the present disclosure also provides the use of the above compound having the structure of Formula I', Formula I, Formula I-1, Formula II, Formula II-1, Formula III or Formula III-1 or the pharmaceutically acceptable salt, ester, isomer, solvate, prodrug or isotopically labelled compound thereof, and the above pharmaceutical composition or pharmaceutical formulation, in preparation of a drug for preventing and/or treating a related disease with a pathologic feature of increased ATX expression; preferably, the related disease with the pathologic feature of increased ATX expression includes cancer, fibrotic diseases, metabolic diseases, myelodysplastic syndrome, respiratory diseases, cardiovascular diseases, autoimmune diseases, inflammation, dermatological diseases, nervous system diseases or pain; more preferably, the related disease with the pathological feature of increased ATX expression is pulmonary fibrosis, renal fibrosis, or liver fibrosis.

[Treatment Method]

The present disclosure provides a method for preventing and/or treating a related disease with a pathologic feature of increased ATX expression, comprising the step of administering an effective amount of the above compound having a structure of Formula I', Formula I, Formula I-1, Formula II, Formula II-1, Formula III or Formula III-1 or the pharmaceutically acceptable salt, ester, isomer, solvate, prodrug or isotopically labelled compound thereof, or the above pharmaceutical composition or pharmaceutical formulation, to a subject in need thereof.

The term "therapeutically effective amount" refers to a dose of an active pharmaceutical ingredient capable of inducing a biological or medical response of a cell, a tissue, an organ or an organism (e.g., a subject).

The term "administration" refers to a process of applying an active pharmaceutical ingredient (such as the compound of the present disclosure) or a pharmaceutical composition comprising the active pharmaceutical ingredient (such as the pharmaceutical composition of the present disclosure) to a subject or the subject's cells, tissues, organs, biological fluids, etc., in order to contact the pharmaceutically active ingredient or the pharmaceutical composition with the subject or the subject's cells, tissues, organs, biological fluids, etc. Common routes of administration include, but are not limited to, oral administration, subcutaneous administration, intramuscular administration, subperitoneal administration, ocular administration, nasal administration, sublingual administration, rectal administration, vaginal administration, etc.

The term "in need thereof" refers to a judgment that a subject needs or will benefit from a prevention and/or treatment process, which is made by a physician or other healthcare providers based on various factors in the expertise field of the physician or other healthcare providers.

The term "subject" (or a testee) refers to a human or a non-human animal (such as a mammal).

The present disclosure will be further described in combination with the following examples; however, these examples should not be regarded as a limitation on the scope of the present disclosure.

Abbreviations used herein are as follows:

AcOH: acetic acid; HCOOH: formic acid; $I_2$: iodine; t-BuONO: tert-butyl nitrite; $CuCl_2$: copper chloride; n-BuOH: n-butanol; $MgCl_2$: magnesium chloride; NaH: sodium hydride; $CH_3I$: methyl iodide; Pd(dppf)$Cl_2$: [1,1'-bis(diphenylphosphino)ferrocene]palladium dichloride; Pd$(PPh_3)_4$: tetrakis(triphenylphosphine)palladium; KOAc: potassium acetate; $B_2(Pin)_2$: bis(pinacolato)diboron; $CDCl_3$: deuterated chloroform; dioxane: 1,4-dioxane; $CO_2$: carbon dioxide; conc. $H_2SO_4$: concentrated sulfuric acid; DCM: dichloromethane; DIEA: N,N-diisopropyl ethylamine; DMF: N,N-dimethylformamide; DMSO: dimethyl sulfoxide; DMSO-$d_6$: deuterated dimethyl sulfoxide; EtOH: ethanol; g: gram; HATU: 2-(7-azabenzotriazol-1-yl)-N,N,N',N'-tetramethyluronium hexafluorophosphate; Hz: hertz; h: hour; $IC_{50}$: half maximal inhibitory concentration; LiOH: lithium hydroxide; MeOH: methanol; mg: milligram; mL: milliliter; mmol: millimole; MHz: megahertz; NaOH: sodium hydroxide; NMR: nuclear magnetic resonance; M: mole/liter; PBS: phosphate buffered saline; TLC: thin layer chromatography; μM: micromole/liter; μg: microgram; μL: microliter; δ: chemical shift.

Common test conditions in examples of the present disclosure will be described below:

Firstly, the reactions in examples are generally carried out under the protection of nitrogen.

Further, intermediates and final products are separated and purified by a chromatography column, a preparative chromatography plate, and ICSO flash preparative chromatography system.

Further, a liquid chromatograph mass spectrometer (LC-MS) used is ACQUITY Arc equipped with QDa Detector from Waters Inc. An ESI source is used in the mass spectrometer (MS), which is only indicative of molecular weight M of a parent molecule, usually reported as $[M+H]^+$. An injection volume is determined by a sample concentration; a flow rate is 0.8 mL/min; peaks in HPLC are recorded and read under UV-Vis light at the wavelengths of 220 nm and 254 nm. Mobile phases are 0.01% formic acid solution in ultrapure water (mobile phase A) and 0.01% formic acid solution in acetonitrile (mobile phase B). The gradient elution conditions are shown in Table 1 and Table 2 below:

TABLE 1

| Gradient elution condition 1 | | |
|---|---|---|
| Time (min) | A ($H_2O$, 0.01% HCOOH) | B ($CH_3CN$, 0.01% HCOOH) |
| 0.0-0.3 | 95-85 | 5-15 |
| 0.3-3.2 | 85-20 | 15-80 |
| 3.2-3.8 | 20-5 | 80-95 |

TABLE 1-continued

| Gradient elution condition 1 | | |
|---|---|---|
| Time (min) | A ($H_2O$, 0.01% HCOOH) | B ($CH_3CN$, 0.01% HCOOH) |
| 3.8-3.81 | 5-95 | 95-5 |
| 3.81-4.0 | 95 | 5 |

TABLE 2

| Gradient elution condition 2 | | |
|---|---|---|
| Time (min) | A ($H_2O$, 0.01% HCOOH) | B ($CH_3CN$, 0.01% HCOOH) |
| 0.00-5.90 | 95-5 | 5-95 |
| 5.90-5.91 | 5-95 | 95-5 |
| 5.91-6.00 | 95 | 5 |

Further, NMR spectra are acquired on Varian 400 MHz NMR Spectrometer, generally in $CDCl_3$ and DMSO-$d_6$ as solvents, and chemical shifts are reported in ppm. The various types of peaks are described as follows: s (singlet), d (doublet), t (triplet), q (quartet), m (multiplet), and dd (doublet of doublets). The coupling constant is expressed in Hz.

Example 1: 2-((2-ethyl-6-(4-(2-(3-hydroxyazetidin-1-yl)-2-oxoethyl)phenyl)imidazo[1,2-a]pyridin-3-yl)(methyl)amino)-4-(4-fluorophenyl)thiazole-5-carbonitrile (compound 1)

1

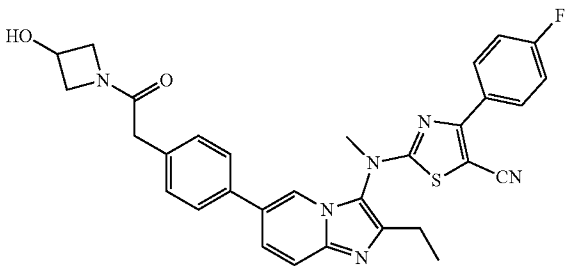

Step 1a: Preparation of 2-amino-4-(4-fluorophenyl)thiazole-5-carbonitrile

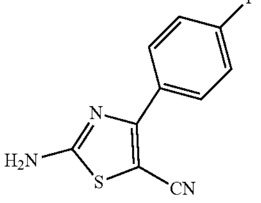

Specific method of Step 1a: pyridine (2.97 mL, 36.78 mmol) was added to a solution of 3-(4-fluorophenyl)-3-oxopropionitrile (6.0 g, 36.78 mmol) in ethanol (72 mL) at room temperature. The mixture was stirred at 70° C. for 15 min and then cooled to room temperature. A solution of thiourea (5.61 g, 73.56 mmol) and iodine (9.33 g, 6.78 mmol) in EtOH (36 mL) was slowly added dropwise. After stirring at room temperature for 1 h, 1 M of $Na_2S_2O_3$ (36 mL) was added for quenching the reaction. After filtration, the filter cake was washed with water, and dried to afford 2-amino-4-(4-fluorophenyl)thiazole-5-carbonitrile (4.2 g) as a white solid.

Step 1b: Preparation of 2-chloro-4-(4-fluorophenyl)thiazole-5-carbonitrile

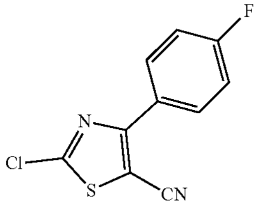 [SMILES: N#Cc1sc(Cl)nc1-c1ccc(F)cc1]

Specific method of Step 1b: tert-butyl nitrite (3.57 g, 34.6 mmol) was added to a solution of copper chloride (3.09 g, 23.0 mmol) in acetonitrile (42 mL) at room temperature. The mixture was stirred at room temperature for 30 min, then added with 2-amino-4-(4-fluorophenyl)thiazole-5-carbonitrile (4.2 g, 19.15 mmol) and stirred at room temperature for 1 h. 1 M of HCl (63 mL) was added for quenching the reaction, and ethyl acetate was used for extraction (100 mL×2). The organic phases were combined, washed with saturated saline (100 mL), dried with anhydrous sodium sulfate, filtered, and concentrated under reduced pressure to afford a crude product. The crude product was purified by flash column chromatography to afford 2-chloro-4-(4-fluorophenyl)thiazole-5-carbonitrile (4.8 g) as a white solid.

Step 1c: Preparation of 6-bromo-2-ethyl-N-(2,4,4-trimethylpent-2-yl)imidazo[1,2-a]pyridine-3-amine

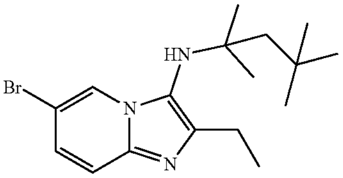 [SMILES: CCc1nc2ccc(Br)cn2c1NC(C)(C)CC(C)(C)C]

Specific method of Step 1c: 5-bromopyridin-2-amine (4.0 g, 23.1 mmol), propionaldehyde (4.4 mL, 25.4 mmol), 1,1,3,3-tetramethylbutyl isocyanide (4.0 mL, 57.8 mmol) and magnesium chloride (220 mg, 2.31 mmol) were dissolved into n-butanol (40 mL), heated to 130° C. and stirred to react for 3 h. After cooling, the reaction solution was concentrated and diluted with water (30 mL). An aqueous phase was extracted with ethyl acetate (80 mL×3), and a combined organic phase was washed with saturated saline (30 mL), dried with anhydrous sodium sulfate, filtered, and concentrated to afford 6-bromo-2-ethyl-N-(2,4,4-trimethylpentan-2-yl)imidazo[1,2-a]pyridine-3-amine (8.8 g) as a brown solid.

Step 1d: Preparation of N-(6-bromo-2-ethylimidazo[1,2-a]pyridin-3-yl)formamide

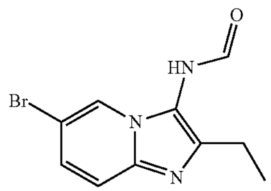

Specific method of Step 1d: 6-bromo-2-ethyl-N-(2,4,4-trimethylpentan-2-yl)imidazo[1,2-a]pyridine-3-amine (8.1 g, 23.0 mmol) was dissolved in formic acid (30 mL) and refluxed for 2 h. After cooling, the reaction solution was concentrated, and then methyl tert-butyl ether (30 mL) was added thereto. After stirring for 15 min and filtering, the filter cake was washed with methyl tert-butyl ether (10 mL) and dried in vacuum to afford N-(6-bromo-2-ethylimidazo[1,2-a]pyridin-3-yl)formamide (5.45 g) as an off-white solid.

Step 1e: Preparation of N-(6-bromo-2-ethylimidazo[1,2-a]pyridin-3-yl)-N-methylformamide

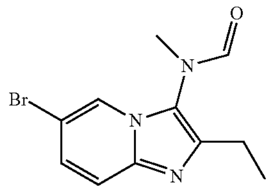 [SMILES: CCc1nc2ccc(Br)cn2c1N(C)C=O]

Specific method of Step 1e: at 0° C., 60% sodium hydride (1.3 g, 33.6 mmol) was added in batches to a solution of N-(6-bromo-2-ethylimidazo[1,2-a]pyridin-3-yl)formamide (6 g, 22.4 mmol) in DMF (50 mL) at a nitrogen atmosphere. The reaction solution was stirred at room temperature for 1 h, and then iodomethane (4.8 g, 33.6 mmol) was added thereto. The mixture was subject to further reaction at room temperature for 3 h and was quenched with water (50 mL), extracted with ethyl acetate (100 mL×3), then the combined organic phase was washed with saturated saline (50 mL), dried with anhydrous sodium sulfate, filtered, and concentrated under reduced pressure to afford a crude product. The crude product was purified by flash column chromatography to obtain N-(6-bromo-2-ethylimidazo[1,2-a]pyridin-3-yl)-N-methylformamide (5 g) as a grey solid.

Step 1f: Preparation of 6-bromo-2-ethyl-N-methyl-imidazo[1,2-a]pyridine-3-amine

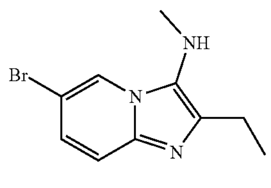

Specific method of Step 1f: 10 M of NaOH solution (24 mL, 240 mmol) was added to a solution of N-(6-bromo-2-ethylimidazo[1,2-a]pyridin-3-yl)-N-methylformamide (4.5 g, 16.0 mmol) in methanol (25 mL). The reaction solution was concentrated after being stirred at room temperature for 3 h, and diluted with ethyl acetate (100 mL), an organic phase was washed with saturated saline (50 mL), dried with anhydrous sodium sulfate, filtered, and concentrated under reduced pressure to afford 6-bromo-2-ethyl-N-methylimidazo[1,2-a]pyridine-3-amine (4.1 g) as an off-white solid.

Step 1g: Preparation of 2-((6-bromo-2-ethylimidazo[1,2-a]pyridin-3-yl)(methyl)amino)-4-(4-fluorophenyl)thiazole-5-carbonitrile

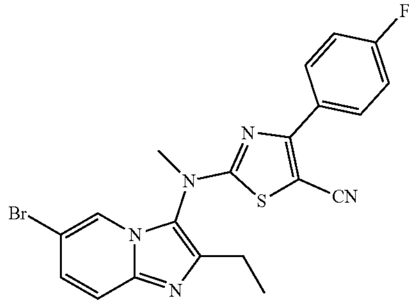 [SMILES: CCc1nc2ccc(Br)cn2c1N(C)c1nc(-c2ccc(F)cc2)c(C#N)s1]

Specific method of Step 1g: at 0° C., 60% sodium hydride (0.79 g, 19.67 mmol) was added to a solution of 6-bromo-2-ethyl-N-methylimidazo[1,2-a]pyridine-3-amine (2.5 g, 9.84 mmol) in DMF (30 mL) at a nitrogen atmosphere. The mixture was stirred at room temperature for 30 min, then added slowly with a solution of 2-chloro-4-(4-fluorophenyl)thiazole-5-carbonitrile (4.8 g, 20.11 mmol) in DMF (10 mL). The mixture was stirred at 80° C. for 4 h, then quenched with saturated aqueous ammonium chloride solution and extracted with ethyl acetate (80 mL×3). The combined organic phase was washed with saturated saline (100 mL), dried with anhydrous sodium sulfate, filtered, and concentrated under reduced pressure to afford a crude product. The crude product was purified by flash column chromatography to afford 2-((6-bromo-2-ethylimidazo[1,2-a]pyridin-3-yl)(methyl)amino)-4-(4-fluorophenyl)thiazole-5-carbonitrile (2.6 g) as a yellow solid.

Step 1h: Preparation of methyl 2-(4-(3-((5-cyano-4-(4-fluorophenyl)thiazol-2-yl)(methyl)amino)-2-ethylimidazo[1,2-a]pyridin-6-yl)phenyl)acetate

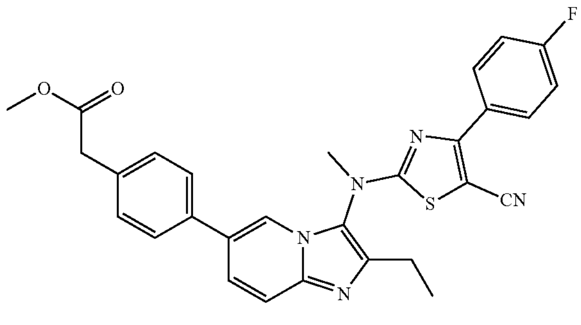 [SMILES: CCc1nc2ccc(-c3ccc(CC(=O)OC)cc3)cn2c1N(C)c1nc(-c2ccc(F)cc2)c(C#N)s1]

Specific method of Step 1h: [1,1'-bis(diphenylphosphino)ferrocene]palladium dichloride (18 mg, 0.022 mmol) and potassium phosphate (93 mg, 0.438 mmol) were added to a solution of 2-((6-bromo-2-ethylimidazo[1,2-a]pyridin-3-yl)(methyl)amino)-4-(4-fluorophenyl)thiazole-5-carbonitrile (100 mg, 0.219 mmol) and methyl 2-(4-(4,4,5,5-tetramethyl-1,3,2-dioxyboran-2-yl)phenyl)acetate (79 mg, 0.285 mmol) in DMF (5 mL) at a nitrogen atmosphere. The mixture was stirred at 85° C. for 4 h, then diluted with water (10 mL) and extracted with ethyl acetate (15 mL×3). The combined organic phase was washed with saturated saline (20 mL), dried with anhydrous sodium sulfate, filtered, and concentrated under reduced pressure to afford a crude product. The crude product was purified by flash column chromatography to afford methyl 2-(4-(3-((5-cyano-4-(4-fluorophenyl)thiazol-2-yl)(methyl)amino)-2-ethylimidazo[1,2-a]pyridin-6-yl)phenyl)acetate (68 mg) as a brown solid.

Step 1i: Preparation of 2-(4-(3-((5-cyano-4-(4-fluorophenyl)thiazol-2-yl)(methyl)amino)-2-ethylimidazo[1,2-a]pyridin-6-yl)phenyl)acetic acid

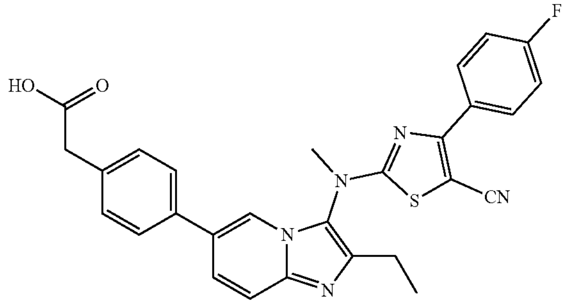 [SMILES: CCc1nc2ccc(-c3ccc(CC(=O)O)cc3)cn2c1N(C)c1nc(-c2ccc(F)cc2)c(C#N)s1]

Specific method of Step 1i: sodium hydroxide (16 mg, 0.387 mmol) was added to a solution of methyl 2-(4-(3-((5-cyano-4-(4-fluorophenyl)thiazol-2-yl)(methyl)amino)-2-ethylimidazo[1,2-a]pyridin-6-yl)phenyl)acetate (68 mg, 0.129 mmol) in tetrahydrofuran (3 mL) and water (1 mL). The mixture was stirred at room temperature for 4 h, then adjusted to pH 3-4 with 1 M of hydrochloric acid solution, and extracted with ethyl acetate (10 mL×3). The combined organic phase was washed with saturated saline (10 mL), dried with anhydrous sodium sulfate, filtered, and concentrated under reduced pressure to afford 2-(4-(3-((5-cyano-4-(4-fluorophenyl)thiazol-2-yl)(methyl)amino)-2-ethylimidazo[1,2-a]pyridin-6-yl)phenyl)acetic acid (55 mg) as a brown solid.

Step 1j: Preparation of 2-((2-ethyl-6-(4-(2-(3-hydroxyazetidin-1-yl)-2-oxoethyl)phenyl)imidazo[1,2-a]pyridin-3-yl)(methyl)amino)-4-(4-fluorophenyl)thiazole-5-carbonitrile

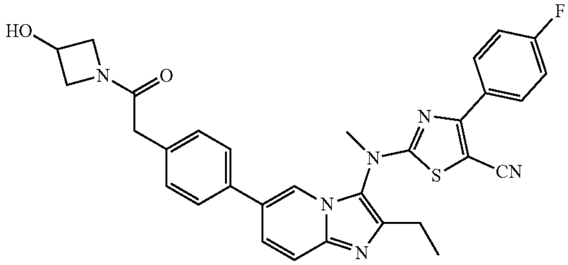

Specific method of Step 1j: DIEA (42 mg, 0.324 mmol) and HATU (62 mg, 0.162 mmol) were added to a solution of 2-(4-(3-((5-cyano-4-(4-fluorophenyl)thiazol-2-yl)(methyl)amino)-2-ethylimidazo[1,2-a]pyridin-6-yl) phenyl)acetic acid (55 mg, 0.11 mmol) and azetidin-3-ol (24 mg, 0.32 mmol) in DMF (2 mL). The mixture was stirred at room temperature for 2 h, then diluted with water (10 mL) and extracted with ethyl acetate (10 mL×3). The combined organic phase was washed with saturated saline (10 mL), dried with anhydrous sodium sulfate, filtered, and concentrated under reduced pressure to afford a crude product. The crude product was purified by flash column chromatography to afford 2-((2-ethyl-6-(4-(2-(3-hydroxyazetidin-1-yl)-2-oxoethyl)phenyl)imidazo[1,2-a]pyridin-3-yl)(methyl)amino)-4-(4-fluorophenyl)thiazole-5-carbonitrile (25.4 mg) as a white solid.

$^1$H NMR (400 MHz, DMSO-$d_6$): δ 8.72 (br. s, 1H), 8.09-8.06 (m, 2H), 7.89 (d, J=8.8 Hz, 1H), 7.80 (d, J=9.2 Hz, 1H), 7.72 (d, J=8.0 Hz, 2H), 7.42 (d, J=8.8 Hz, 2H), 7.34 (d, J=8.0 Hz, 2H), 4.46-4.41 (m, 1H), 4.36 (d, J=7.8 Hz, 1H), 4.04-3.99 (m, 1H), 3.91-3.88 (m, 1H), 3.65 (s, 3H), 3.58-3.54 (m, 1H), 3.47 (s, 2H), 2.75-2.70 (q, J=7.6 Hz, 2H), 1.38 (t, J=7.6 Hz, 3H).

Measured value of MS (ESI$^+$) [(M+H)$^+$]: 567.

Example 2: 2-((2-ethyl-6-(6-(2-(3-hydroxyazetidin-1-yl)-2-oxoethyl)pyridin-3-yl)imidazo[1,2-a]pyridin-3-yl)(methyl)amino)-4-(4-fluorophenyl)thiazole-5-carbonitrile (compound 2)

2

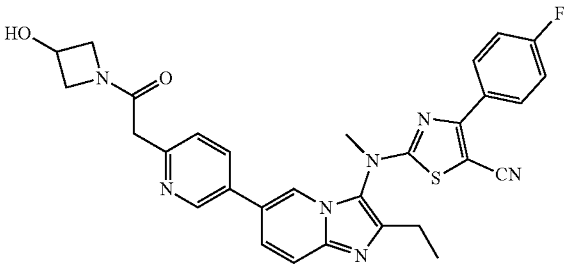

Step 2a: Preparation of ethyl 2-(5-(4,4,5,5-tetramethyl-1,3,2-dioxaborolan-2-yl)pyridin-2-yl)acetate

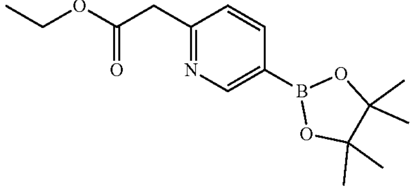 [SMILES: CCOC(=O)Cc1ccc(B2OC(C)(C)C(C)(C)O2)cn1]

Specific method of Step 2a: [1,1'-bis(diphenylphosphino)ferrocene]palladium dichloride (58 mg, 0.08 mmol) was added to a solution of ethyl 2-(5-bromopyridin-2-yl)acetate (200 mg, 0.82 mmol), bis(pinacolato)diboron (229 mg, 0.90 mmol) and potassium acetate (120 mg, 1.23 mmol) in 1,4-dioxane (2 mL) under nitrogen atmosphere. The mixture was heated to 85° C. and stirred for 2 h, then diluted with water (15 mL) and extracted with ethyl acetate (20 mL×2). The combined organic phase was washed with saturated saline (15 mL), dried with anhydrous sodium sulfate, filtered, and concentrated under reduced pressure to afford ethyl 2-(5-(4,4,5,5-tetramethyl-1,3,2-dioxaborolan-2-yl)pyridin-2-yl)acetate (171 mg) as a brown oil.

Step 2b: Preparation of ethyl 2-(5-(3-((5-cyano-4-(4-fluorophenyl)thiazol-2-yl)(methyl)amino)-2-ethylimidazo[1,2-a]pyridin-6-yl)pyridin-2-yl)acetate

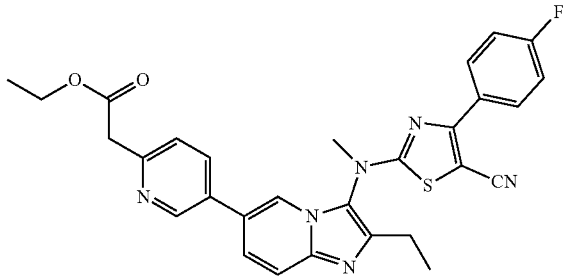 [SMILES: CCOC(=O)Cc1ccc(-c2ccc3nc(CC)c(N(C)c4nc(-c5ccc(F)cc5)c(C#N)s4)n3c2)cn1]

Specific method of Step 2b: ethyl 2-(5-(3-((5-cyano-4-(4-fluorophenyl)thiazol-2-yl)(methyl)amino)-2-ethylimidazo[1,2-a]pyridin-6-yl)pyridin-2-yl)acetate (60 mg) as a brown solid was prepared from 2-((6-bromo-2-ethylimidazo[1,2-a]pyridin-3-yl)(methyl)amino)-4-(4-fluorophenyl)thiazole-5-carbonitrile (100 mg, 0.22 mmol) and ethyl 2-(5-(4,4,5,5-tetramethyl-1,3,2-dioxaborolan-2-yl)pyridin-2-yl)acetate (55 mg, 0.26 mmol) according to the method of step 1h in Example 1.

Step 2c: Preparation of 2-(5-(3-((5-cyano-4-(4-fluorophenyl)thiazol-2-yl)(methyl)amino)-2-ethylimidazo[1,2-a]pyridin-6-yl)pyridin-2-yl)acetic acid

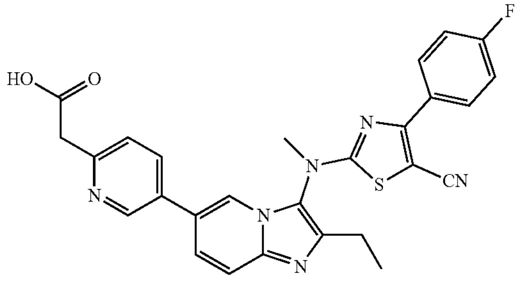

Specific method of Step 2c: 2-(5-(3-((5-cyano-4-(4-fluorophenyl)thiazol-2-yl)(methyl)amino)-2-ethylimidazo[1,2-a]pyridin-6-yl)pyridin-2-yl)acetic acid (45 mg) as a brown solid was prepared from ethyl 2-(5-(3-((5-cyano-4-(4-fluorophenyl)thiazol-2-yl)(methyl)amino)-2-ethylimidazo[1,2-a]pyridin-6-yl)pyridin-2-yl)acetate (50 mg, 0.09 mmol) and sodium hydroxide (11 mg, 0.27 mmol) according to the method of step 1i in Example 1.

Step 2d: Preparation of 2-((2-ethyl-6-(6-(2-(3-hydroxyazetidin-1-yl)-2-oxoethyl)pyridin-3-yl)imidazo[1,2-a]pyridin-3-yl)(methyl)amino)-4-(4-fluorophenyl)thiazole-5-carbonitrile

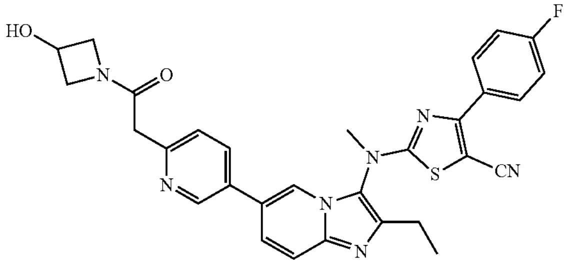 [SMILES: CCc1nc2ccc(-c3ccc(CC(=O)N4CC(O)C4)nc3)cn2c1N(C)c1nc(-c2ccc(F)cc2)c(C#N)s1]

Specific method of Step 2d: 2-((2-ethyl-6-(6-(2-(3-hydroxyazetidin-1-yl)-2-oxoethyl)pyridin-3-yl)imidazo[1,2-a]pyridin-3-yl)(methyl)amino)-4-(4-fluorophenyl)thiazole-5-carbonitrile (28.9 mg) as a white solid was prepared from 2-(5-(3-((5-cyano-4-(4-fluorophenyl)thiazol-2-yl)(methyl)amino)-2-ethylimidazo[1,2-a]pyridin-6-yl)pyridin-2-yl)acetic acid (45 mg, 0.09 mmol) and azetidin-3-ol (20 mg, 0.27 mmol) according to the method of step 1j in Example 1.

$^1$H NMR (400 MHz, $CDCl_3$): δ 8.68 (d, J=2.0 Hz, 1H), 8.15 (dd, J=8.8, 5.4 Hz, 2H), 7.92 (s, 1H), 7.81 (dd, J=8.1, 2.2 Hz, 1H), 7.74 (d, J=9.4 Hz, 1H), 7.51 (dd, J=9.4, 1.4 Hz, 1H), 7.46 (d, J=8.2 Hz, 1H), 7.20-7.15 (m, 2H), 4.71-4.65 (m, 1H), 4.54-4.48 (m, 1H), 4.29-4.24 (m, 1H), 4.16-4.13 (m, 1H), 3.91-3.88 (m, 1H), 3.70 (s, 2H), 3.68 (s, 3H), 3.17 (br. s, 1H), 2.80 (q, J=7.4 Hz, 2H), 1.40 (t, J=7.6 Hz, 3H).

Measured value of MS (ESI$^+$) [(M+H)$^+$]: 568.

Example 3: 2-((2-ethyl-6-(5-fluoro-6-(2-(3-hydroxyazetidin-1-yl)-2-oxoethyl)pyridin-3-yl)imidazo[1,2-a]pyridin-3-yl)(methyl)amino)-4-(4-fluorophenyl)thiazole-5-carbonitrile (compound 3)

3

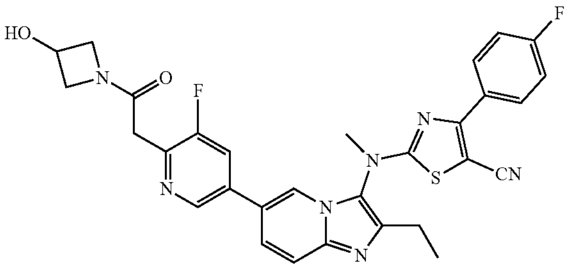

Step 3a: Preparation of 1-(tert-butyl) 3-ethyl 2-(5-bromo-3-fluoropyridin-2-yl)malonate

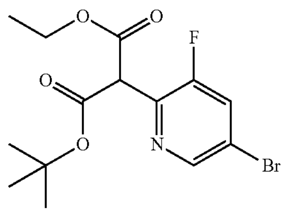 [SMILES: CCOC(=O)C(C(=O)OC(C)(C)C)c1ncc(Br)cc1F]

Specific method of Step 3a: at 0° C., 60% sodium hydride (893 mg, 22.3 mmol) was added in batches to a solution of tert-butyl ethyl malonate (3.5 g, 18.6 mmol) in dried DMF (30 mL) at nitrogen atmosphere. After the mixture continued to be stirred at 0° C. for half an hour, 5-bromo-2,3-difluoropyridine (3 g, 15.5 mmol) was added thereto, then the reaction solution was stirred at 80° C. for 3 h. The reaction was quenched with water (35 mL), extracted with ethyl acetate (30 mL×3), then the combined organic phase was washed with saturated saline (10 mL), dried with anhydrous sodium sulfate, filtered, and concentrated under reduced pressure to afford 1-(tert-butyl) 3-ethyl 2-(5-bromo-3-fluoropyridinyl-2-yl)malonate (3 g) as a brown oil.

Step 3b: Preparation of ethyl 2-(5-bromo-3-fluoropyridin-2-yl)acetate

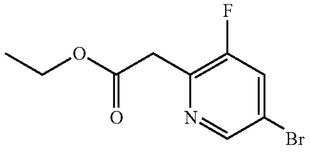

Specific method of Step 3b: at 0° C., trifluoroacetic acid (5 mL) was added to a solution of 1-(tert-butyl) 3-ethyl 2-(5-bromo-3-fluoropyridin-2-yl)malonate (3 g, 8.30 mmol) in dichloromethane (5 mL). The mixture continued to be stirred at room temperature for 2 h, concentrated, diluted with water (15 mL), and extracted with ethyl acetate (10 mL×3). The combined organic phase was washed with saturated saline (10 mL), dried with anhydrous sodium sulfate, filtered, and concentrated under reduced pressure to afford a crude product. The crude product was purified by column chromatography to afford ethyl 2-(5-bromo-3-fluoropyridin-2-yl)acetate (1.2 g) as a yellow oil.

Step 3c: Preparation of ethyl 2-(3-fluoro-5-(4,4,5,5-tetramethyl-1,3,2-dioxaborolan-2-yl)pyridin-2-yl) acetate

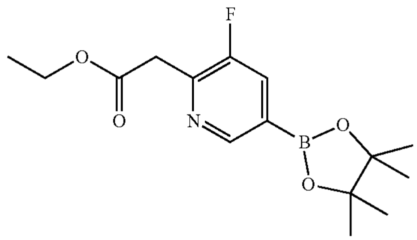 [SMILES: CCOC(=O)Cc1ncc(B2OC(C)(C)C(C)(C)O2)cc1F]

Specific method of Step 3c: [1,1'-bis(diphenylphosphino) ferrocene]palladium dichloride (29 mg, 0.04 mmol) was added to a solution of ethyl 2-(5-bromo-3-fluoropyridin-2-yl)acetate (100 mg, 0.38 mmol), bis(pinacolato)diboron (115 mg, 0.46 mmol) and potassium acetate (56 mg, 0.57 mmol) in 1,4-dioxane (2 mL) under the protection of nitrogen. The mixture was heated to 85° C. and stirred for 3 h, then diluted with water (15 mL) and extracted with ethyl acetate (20 mL×2). The combined organic phase was washed with saturated saline (15 mL), dried with anhydrous sodium sulfate, filtered, and concentrated under reduced pressure to afford ethyl 2-(3-fluoro-5-(4,4,5,5-tetramethyl-1,3,2-dioxaborolan-2-yl)pyridin-2-yl)acetate (100 mg) as a brown solid.

Step 3d: Preparation of ethyl 2-(5-(3-((5-cyano-4-(4-fluorophenyl)thiazol-2-yl)(methyl)amino)-2-ethylimidazo[1,2-a]pyridin-6-yl)-3-fluoropyridin-2-yl) acetate

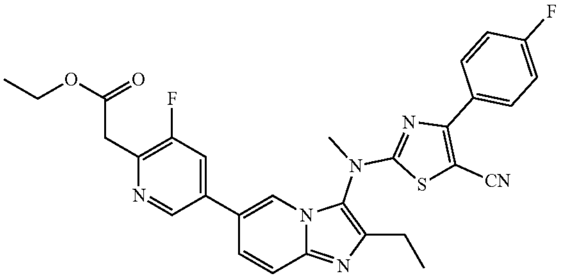 [SMILES: CCOC(=O)Cc1ncc(-c2ccc3nc(CC)c(N(C)c4nc(-c5ccc(F)cc5)c(C#N)s4)n3c2)cc1F]

Specific method of Step 3d: ethyl 2-(5-(3-((5-cyano-4-(4-fluorophenyl)thiazol-2-yl)(methyl)amino)-2-ethylimidazo [1,2-a]pyridin-6-yl)-3-fluoropyridin-2-yl)acetate (50 mg) as a brown solid was prepared from 2-((6-bromo-2-ethylimidazo[1,2-a]pyridin-3-yl)(methyl)amino)-4-(4-fluorophenyl) thiazole-5-carbonitrile (100 mg, 0.22 mmol) and ethyl 2-(3-fluoro-5-(4,4,5,5-tetramethyl-1,3,2-dioxaborolan-2-yl) pyridin-2-yl)acetate (100 mg, 0.33 mmol) according to the method of step 1h in Example 1.

Step 3e: Preparation of 2-(5-(3-((5-cyano-4-(4-fluorophenyl)thiazol-2-yl)(methyl)amino)-2-ethylimidazo[1,2-a]pyridin-6-yl)-3-fluoropyridin-2-yl)acetic acid

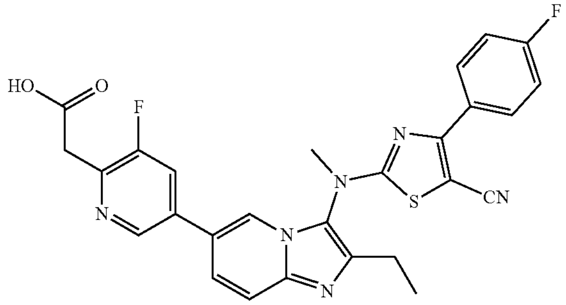 [SMILES: CCc1nc2ccc(-c3cnc(CC(=O)O)c(F)c3)cn2c1N(C)c1nc(-c2ccc(F)cc2)c(C#N)s1]

Specific method of Step 3e: 2-(5-(3-((5-cyano-4-(4-fluorophenyl)thiazol-2-yl)(methyl)amino)-2-ethylimidazo[1,2-a]pyridin-6-yl)-3-fluoropyridin-2-yl)acetic acid (45 mg) as a brown solid was prepared from ethyl 2-(5-(3-((5-cyano-4-(4-fluorophenyl)thiazol-2-yl)(methyl)amino)-2-ethylimidazo[1,2-a]pyridin-6-yl)-3-fluoropyridin-2-yl)acetate (50 mg, 0.09 mmol) and sodium hydroxide (11 mg, 0.27 mmol) according to the method of step 1i in Example 1.

Step 3f: Preparation of 2-((2-ethyl-6-(5-fluoro-6-(2-(3-hydroxyazetidin-1-yl)-2-oxoethyl)pyridin-3-yl)imidazo[1,2-a]pyridin-3-yl)(methyl)amino)-4-(4-fluorophenyl)thiazole-5-carbonitrile

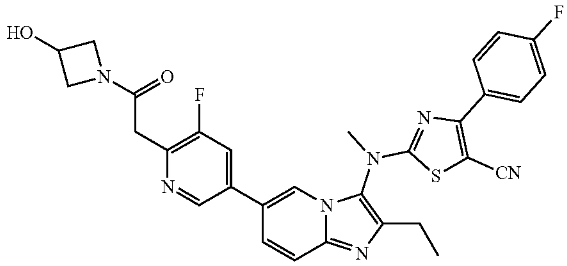 [SMILES: CCc1nc2ccc(-c3cnc(CC(=O)N4CC(O)C4)c(F)c3)cn2c1N(C)c1nc(-c2ccc(F)cc2)c(C#N)s1]

Specific method of Step 3f: 2-((2-ethyl-6-(5-fluoro-6-(2-(3-hydroxyazetidin-1-yl)-2-oxoethyl)pyridin-3-yl)imidazo[1,2-a]pyridin-3-yl)(methyl)amino)-4-(4-fluorophenyl)thiazole-5-carbonitrile (18 mg) as a white solid was prepared from 2-(5-(3-((5-cyano-4-(4-fluorophenyl)thiazol-2-yl)(methyl)amino)-2-ethylimidazo[1,2-a]pyridin-6-yl)-3-fluoropyridin-2-yl)acetic acid (45 mg, 0.08 mmol) and azetidin-3-ol (10 mg, 0.13 mmol) according to the method of step 1j in Example 1.

$^1$H NMR (400 MHz, $CDCl_3$): δ 8.54 (s, 1H), 8.17-8.13 (m, 2H), 7.92 (s, 1H), 7.75 (d, J=8.0 Hz, 1H), 7.52 (dd, J=8.0 Hz, 2.0 Hz, 2H), 7.17 (t, J=8.0 Hz, 2H), 4.70 (d, J 4.0 Hz, 1H), 4.49 (t, J=8.0 Hz, 1H), 4.32-4.28 (m, 1H), 4.14 (dd, J=8.0, 4.0 Hz, 1H), 3.91 (dd, J=8.0, 4.0 Hz, 1H), 3.76 (s, 2H), 3.72 (d, J=8.0 Hz, 1H), 3.68 (s, 3H), 2.80 (q, J=8.0 Hz, 2H), 1.39 (t, J=8.0 Hz, 3H).

Measured value of MS ($ESI^+$) [$(M+H)^+$]: 586.

Example 4: 2-((2-ethyl-6-(5-(2-(3-hydroxyazetidin-1-yl)-2-oxoethyl)pyrazin-2-yl)imidazo[1,2-a]pyridin-3-yl)(methyl)amino)-4-(4-fluorophenyl)thiazole-5-carbonitrile (compound 4)

4

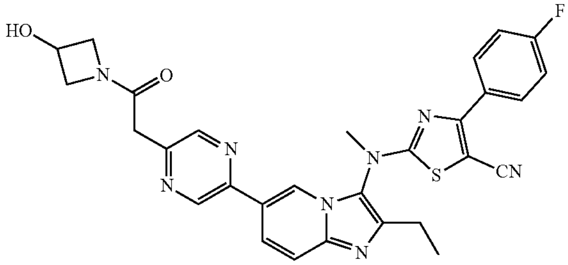

Step 4a: Preparation of 1-(tert-butyl) 3-ethyl 2-(5-bromopyrazin-2-yl)malonate

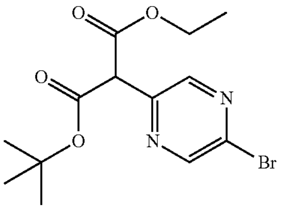 [SMILES: CCOC(=O)C(C(=O)OC(C)(C)C)c1cnc(Br)cn1]

Specific method of Step 4a: 1-(tert-butyl) 3-ethyl 2-(5-bromopyrazin-2-yl)malonate (1.5 g) as a yellow solid was prepared from 2,5-dibromopyrazine (1 g, 4.20 mmol) and tert-butyl ethyl malonate (870 mg, 4.62 mmol) according to the method of step 3a in Example 3.

Step 4b: Preparation of ethyl 2-(5-bromopyrazin-2-yl)acetate

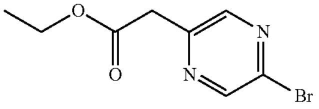

Specific method of Step 4b: ethyl 2-(5-bromopyrazin-2-yl)acetate (400 mg) as a yellow oil was prepared from 1-(tert-butyl) 3-ethyl 2-(5-bromopyrazin-2-yl)malonate (1.5 g, 4.35 mmol) according to the method of step 3b in Example 3.

Step 4c: Preparation of (3-((5-cyano-4-(4-fluorophenyl)thiazol-2-yl)(methyl)amino)-2-ethylimidazo[1,2-a]pyridin-6-yl)boronic acid

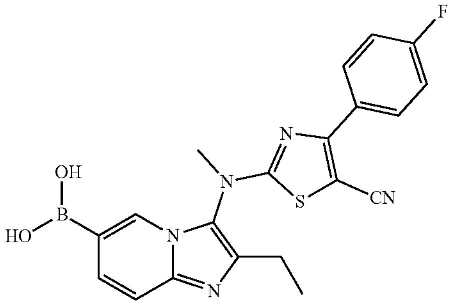 [SMILES: CCc1nc2ccc(B(O)O)cn2c1N(C)c1nc(-c2ccc(F)cc2)c(C#N)s1]

Specific method of Step 4c: (3-((5-cyano-4-(4-fluorophenyl)thiazol-2-yl)(methyl)amino)-2-ethylimidazo[1,2-a]pyridin-6-yl)boronic acid (100 mg) as a brown oil was prepared from 2-((6-bromo-2-ethylimidazo[1,2-a]pyridin-3-yl)(methyl)amino)-4-(4-fluorophenyl)thiazole-5-carbonitrile (100 mg, 0.22 mmol) and bis(pinacolato)diboron (67 mg, 0.26 mmol) according to the method of step 3c in Example 3.

Step 4d: Preparation of ethyl 2-(5-(3-((5-cyano-4-(4-fluorophenyl)thiazol-2-yl)(methyl)amino)-2-ethylimidazo[1,2-a]pyridin-6-yl)pyrazin-2-yl)acetate

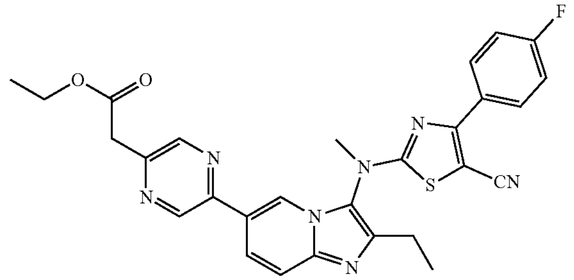 [SMILES: CCOC(=O)Cc1cnc(-c2ccc3nc(CC)c(N(C)c4nc(-c5ccc(F)cc5)c(C#N)s4)n3c2)cn1]

Specific method of Step 4d: ethyl 2-(5-(3-((5-cyano-4-(4-fluorophenyl)thiazol-2-yl)(methyl)amino)-2-ethylimidazo[1,2-a]pyridin-6-yl)pyrazin-2-yl)acetate (50 mg) as a brown solid was prepared from (3-((5-cyano-4-(4-fluorophenyl)thiazol-2-yl)(methyl)amino)-2-ethylimidazo[1,2-a]pyridin-6-yl)boronic acid (100 mg, 0.22 mmol) and ethyl 2-(5-bromopyrazin-2-yl)acetate (87 mg, 0.36 mmol) according to the method of step 1h in Example 1.

Step 4e: Preparation of 2-(5-(3-((5-cyano-4-(4-fluorophenyl)thiazol-2-yl)(methyl)amino)-2-ethylimidazo[1,2-a]pyridin-6-yl)pyrazin-2-yl)acetic acid

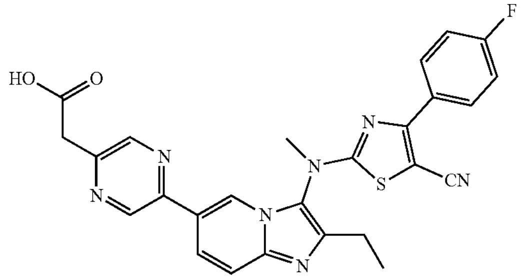 [SMILES: CCc1nc2ccc(-c3cnc(CC(=O)O)cn3)cn2c1N(C)c1nc(-c2ccc(F)cc2)c(C#N)s1]

Specific method of Step 4e: 2-(5-(3-((5-cyano-4-(4-fluorophenyl)thiazol-2-yl)(methyl)amino)-2-ethylimidazo[1,2-a]pyridin-6-yl)pyrazin-2-yl)acetic acid (40 mg) as a brown solid was prepared from ethyl 2-(5-(3-((5-cyano-4-(4-fluorophenyl)thiazol-2-yl)(methyl)amino)-2-ethylimidazo[1,2-a]pyridin-6-yl)pyrazin-2-yl)acetate (50 mg, 0.09 mmol) and sodium hydroxide (11 mg, 0.27 mmol) according to the method of step 1i in Example 1.

Step 4f: Preparation of 2-((2-ethyl-6-(5-(2-(3-hydroxyazetidin-1-yl)-2-oxoethyl)pyrazin-2-yl)imidazo[1,2-a]pyridin-3-yl)(methyl)amino)-4-(4-fluorophenyl)thiazole-5-carbonitrile

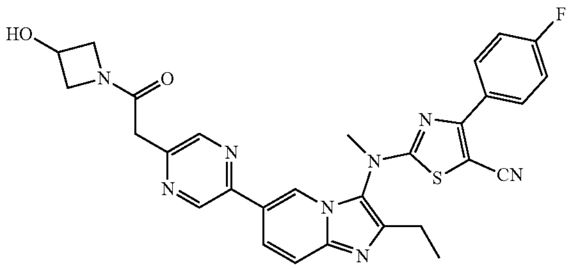 [SMILES: CCc1nc2ccc(-c3cnc(CC(=O)N4CC(O)C4)cn3)cn2c1N(C)c1nc(-c2ccc(F)cc2)c(C#N)s1]

Specific method of Step 4f: 2-((2-ethyl-6-(5-(2-(3-hydroxyazetidin-1-yl)-2-oxoethyl)pyrazin-2-yl)imidazo[1,2-a]pyridin-3-yl)(methyl)amino)-4-(4-fluorophenyl)thiazole-5-carbonitrile (7 mg) as an off-white solid was prepared from 2-(5-(3-((5-cyano-4-(4-fluorophenyl)thiazol-2-yl)(methyl)amino)-2-ethylimidazo[1,2-a]pyridin-6-yl)pyrazin-2-yl)acetic acid (40 mg, 0.08 mmol) and azetidin-3-ol (18 mg, 0.23 mmol) according to the method of step 1j in Example 1.

$^1$H NMR (400 MHz, $CDCl_3$): δ 8.91 (s, 1H), 8.66 (s, 1H), 8.56 (s, 1H), 8.15 (dd, J=8.8, 5.2 Hz, 2H), 7.94 (d, J=9.6 Hz, 1H), 7.86 (d, J=8.8 Hz, 1H), 7.18 (t, J=8.6 Hz, 2H), 4.75-4.71 (m, 1H), 4.58-4.51 (m, 1H), 4.34-4.27 (m, 1H), 4.23-4.17 (m, 1H), 3.95-3.89 (m, 1H), 3.73 (s, 2H), 3.70 (s, 3H), 2.82 (q, J=7.7 Hz, 2H), 1.40 (t, J=7.4 Hz, 3H).

Measured value of MS ($ESI^+$) [$(M+H)^+$]: 569.

Example 5: 2-((2-ethyl-6-(6-(2-(3-hydroxyazetidin-1-yl)-2-oxoethyl)pyridazin-3-yl)imidazo[1,2-a]pyridin-3-yl)(methyl)amino)-4-(4-fluorophenyl)thiazole-5-carbonitrile (compound 5)

5

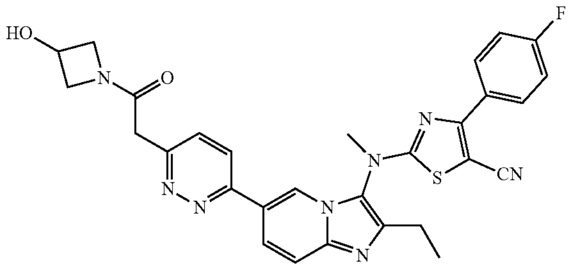

Step 5a: Preparation of 1-(tert-butyl) 3-ethyl 2-(6-chloropyridazin-3-yl)malonate

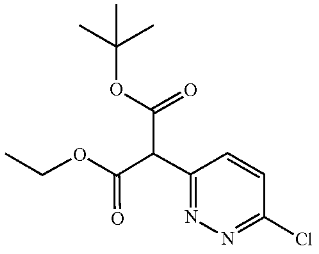 [SMILES: CCOC(=O)C(C(=O)OC(C)(C)C)c1ccc(Cl)nn1]

Specific method of Step 5a: 1-(tert-butyl) 3-ethyl 2-(6-chloropyridazin-3-yl)malonate (1.0 g) as a yellow liquid was prepared from 3,6-dichloropyridazine (1 g, 6.70 mmol) and tert-butyl ethyl malonate (1.3 g, 6.70 mmol) according to the method of step 3a in Example 3.

Step 5b: Preparation of ethyl 2-(6-chloropyridazin-3-yl)acetate

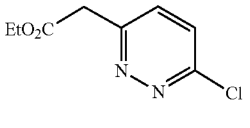 [SMILES: CCOC(=O)Cc1ccc(Cl)nn1]

Specific method of Step 5b: ethyl 2-(6-chloropyridazin-3-yl)acetate (400 mg) as a yellow oil was prepared from 1-(tert-butyl) 3-ethyl 2-(6-chloropyridazin-3-yl)malonate (1.0 g, 3.33 mmol) according to the method of step 3b in Example 3.

Step 5c: Preparation of ethyl 2-(6-(3-((5-cyano-4-(4-fluorophenyl)thiazol-2-yl)(methyl)amino)-2-ethylimidazo[1,2-a]pyridin-6-yl)pyridazin-2-yl)acetate

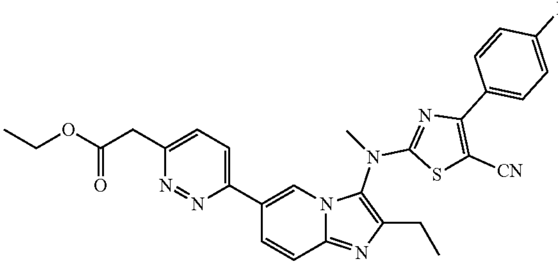

Specific method of Step 5c: ethyl 2-(6-(3-((5-cyano-4-(4-fluorophenyl)thiazol-2-yl)(methyl)amino)-2-ethylimidazo[1,2-a]pyridin-6-yl)pyridazin-2-yl)acetate (90 mg) as a brown solid was prepared from 2-((6-bromo-2-ethylimidazo[1,2-a]pyridin-3-yl)(methyl)amino)-4-(4-fluorophenyl)thiazole-5-carbonitrile (100 mg, 0.22 mmol) and ethyl 2-(6-chloropyridazin-3-yl)acetate (60 mg, 0.30 mmol) according to the method of step 1h in Example 1.

Step 5d: Preparation of 2-(6-(3-((5-cyano-4-(4-fluorophenyl)thiazol-2-yl)(methyl)amino)-2-ethylimidazo[1,2-a]pyridin-6-yl)pyridazin-3-yl)acetic acid

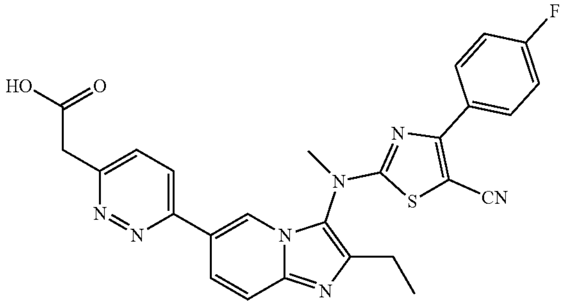 [SMILES: CCc1nc2ccc(-c3ccc(CC(=O)O)nn3)cn2c1N(C)c1nc(-c2ccc(F)cc2)c(C#N)s1]

Specific method of Step 5d: lithium hydroxide monohydrate (10 mg, 0.250 mmol) was added to a solution of ethyl 2-(6-(3-((5-cyano-4-(4-fluorophenyl)thiazol-2-yl)(methyl)amino)-2-ethylimidazo[1,2-a]pyridin-6-yl)pyridazin-3-yl)acetate (90 mg, 0.166 mmol) in tetrahydrofuran (1 mL) and water (0.2 mL). The mixture was stirred at room temperature for 2 h, then concentrated under reduced pressure by an oil pump to obtain 2-(6-(3-((5-cyano-4-(4-fluorophenyl)thiazol-2-yl)(methyl)amino)-2-ethylimidazo[1,2-a]pyridin-6-yl)pyridazin-3-yl)acetic acid (100 mg) as a brown solid.

Step 5e: Preparation of 2-((2-ethyl-6-(6-(2-(3-hydroxyazetidin-1-yl)-2-oxoethyl)pyridazin-3-yl)imidazo[1,2-a]pyridin-3-yl)(methyl)amino)-4-(4-fluorophenyl)thiazole-5-carbonitrile

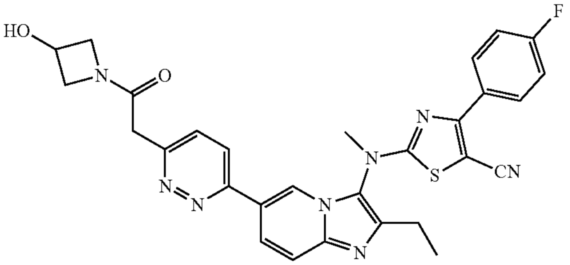 [SMILES: CCc1nc2ccc(-c3ccc(CC(=O)N4CC(O)C4)nn3)cn2c1N(C)c1nc(-c2ccc(F)cc2)c(C#N)s1]

Specific method of Step 5e: a solution of 2-(6-(3-((5-cyano-4-(4-fluorophenyl)thiazol-2-yl)(methyl)amino)-2-ethylimidazo[1,2-a]pyridin-6-yl)pyridazin-3-yl)acetic acid (90 mg, 0.175 mmol) and HATU (80 mg, 0.211 mmol) in DMF (2 mL) was stirred at 0° C. for half an hour, and then azetidin-3-ol (18 mg, 0.23 mmol) was added thereto. The mixture was stirred at room temperature for 1 h, then diluted with water (10 mL) and extracted with ethyl acetate (10 mL×3). The combined organic phase was washed with saturated saline (10 mL), dried with anhydrous sodium sulfate, filtered, and concentrated under reduced pressure to afford a crude product. The crude product was purified by flash column chromatography to afford 2-((2-ethyl-6-(6-(2-(3-hydroxyazetidin-1-yl)-2-oxoethyl)pyridazin-3-yl)imidazo[1,2-a]pyridin-3-yl)(methyl)amino)-4-(4-fluorophenyl)thiazole-5-carbonitrile (15.0 mg) as a white solid.

$^1H$ NMR (400 MHz, $CDCl_3$): δ 8.78 (s, 1H), 8.16-8.12 (m, 2H), 7.84-7.75 (m, 4H), 7.18 (t, J=8.0 Hz, 2H), 4.69 (br.

s, 1H), 4.59 (t, J=8.0 Hz, 1H), 4.28-4.18 (m, 2H), 3.92-3.91 (m, 1H), 3.88 (s, 2H), 3.69 (s, 3H), 2.80 (q, J=8.0 Hz, 2H), 1.40 (t, J=8.0 Hz, 3H).

Measured value of MS (ESI$^+$) [(M+H)$^+$]: 569.

Example 6: 2-((2-ethyl-6-(6-(2-(3-hydroxyazetidin-1-yl)-2-oxoethyl)-2-methylpyridin-3-yl)imidazo[1,2-a]pyridin-3-yl)(methyl)amino)-4-(4-fluorophenyl) thiazole-5-carbonitrile (compound 6)

6

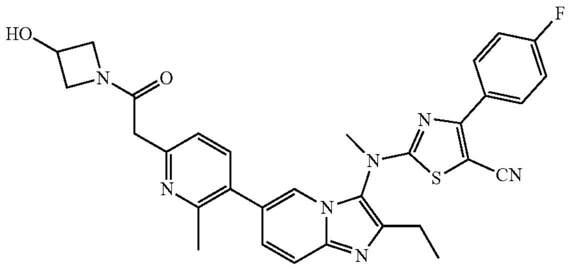

Step 6a: Preparation of 1-(tert-butyl) 3-ethyl 2-(5-bromo-6-methylpyridin-2-yl)malonate

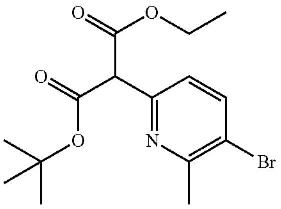 [SMILES: CCOC(=O)C(C(=O)OC(C)(C)C)c1ccc(Br)c(C)n1]

Specific method of Step 6a: 1-(tert-butyl) 3-ethyl 2-(5-bromo-6-methylpyridin-2-yl)malonate (0.3 g) as a yellow solid was prepared from 3-bromo-6-fluoro-2-methylpyridine (0.5 g, 2.63 mmol) and tert-butyl ethyl malonate (1.5 mL, 7.89 mmol) according to the method of step 3a in Example 3.

Step 6b: Preparation of ethyl 2-(5-bromo-6-methylpyridin-2-yl)acetate

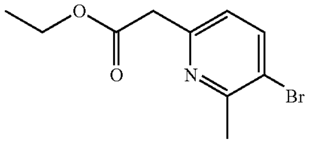

Specific method of Step 6b: ethyl 2-(5-bromo-6-methylpyridin-2-yl)acetate (100 mg) as a yellow oil was prepared from 1-(tert-butyl) 3-ethyl 2-(5-bromo-6-methylpyridin-2-yl)malonate (0.3 g, 1.58 mmol) according to the method of step 3b in Example 3.

Step 6c: Preparation of (3-((5-cyano-4-(4-fluorophenyl)thiazol-2-yl)(methyl)amino)-2-ethylimidazo [1,2-a]pyridin-6-yl)boronic acid

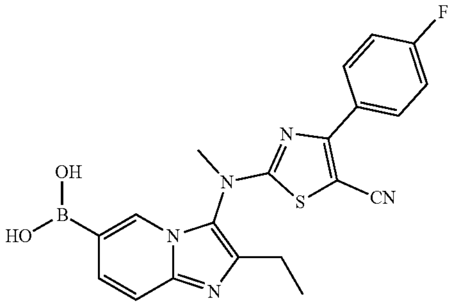 [SMILES: CCc1nc2ccc(B(O)O)cn2c1N(C)c1nc(-c2ccc(F)cc2)c(C#N)s1]

Specific method of Step 6c: (3-((5-cyano-4-(4-fluorophenyl)thiazol-2-yl)(methyl)amino)-2-ethylimidazo[1,2-a]pyridin-6-yl)boronic acid (200 mg) as a brown oil was prepared from 2-((6-bromo-2-ethylimidazo[1,2-a]pyridin-3-yl)(methyl)amino)-4-(4-fluorophenyl)thiazole-5-carbonitrile (200 mg, 0.44 mmol) and bis(pinacolato)diboron (134 mg, 0.52 mmol) according to the method of step 3c in Example 3.

Step 6d: Preparation of ethyl 2-(5-(3-((5-cyano-4-(4-fluorophenyl)thiazol-2-yl)(methyl)amino)-2-ethylimidazo[1,2-a]pyridin-6-yl)-6-methylpyridin-2-yl) acetate

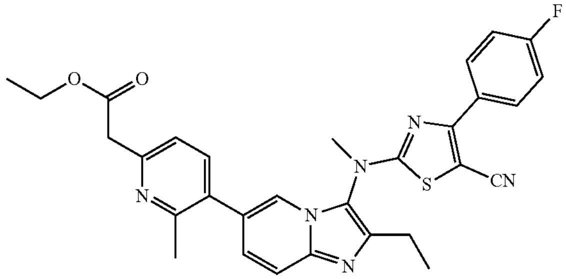 [SMILES: CCOC(=O)Cc1ccc(-c2ccc3nc(CC)c(N(C)c4nc(-c5ccc(F)cc5)c(C#N)s4)n3c2)c(C)n1]

Specific method of Step 6d: ethyl 2-(5-(3-((5-cyano-4-(4-fluorophenyl)thiazol-2-yl)(methyl)amino)-2-ethylimidazo [1,2-a]pyridin-6-yl)-6-methylpyridin-2-yl)acetate (27 mg) as a brown solid was prepared from (3-((5-cyano-4-(4-fluorophenyl)thiazol-2-yl)(methyl)amino)-2-ethylimidazo [1,2-a]pyridin-6-yl)boronic acid (90 mg, 0.21 mmol) and ethyl 2-(5-bromo-6-methylpyridin-2-yl)acetate (66 mg, 0.26 mmol) according to the method of step 1h in Example 1.

Step 6e: Preparation of 2-(5-(3-((5-cyano-4-(4-fluorophenyl)thiazol-2-yl)(methyl)amino)-2-ethylimidazo[1,2-a]pyridin-6-yl)-6-methylpyridin-2-yl)acetic acid

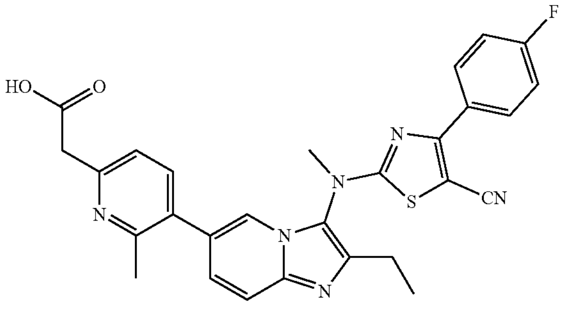 [SMILES: CCc1nc2ccc(-c3ccc(CC(=O)O)nc3C)cn2c1N(C)c1nc(-c2ccc(F)cc2)c(C#N)s1]

Specific method of Step 6e: 2-(5-(3-((5-cyano-4-(4-fluorophenyl)thiazol-2-yl)(methyl)amino)-2-ethylimidazo[1,2-a]pyridin-6-yl)-6-methylpyridin-2-yl)acetic acid (25.6 mg) as a brown solid was prepared from ethyl 2-(5-(3-((5-cyano-4-(4-fluorophenyl)thiazol-2-yl)(methyl)amino)-2-ethylimidazo[1,2-a]pyridin-6-yl)-6-methylpyridin-2-yl)acetate (27 mg, 0.05 mmol) and sodium hydroxide (8.0 mg, 0.20 mmol) according to the method of step 1i in Example 1.

Step 6f: Preparation of 2-((2-ethyl-6-(6-(2-(3-hydroxyazetidin-1-yl)-2-oxoethyl)-2-methylpyridin-3-yl)imidazo[1,2-a]pyridin-3-yl)(methyl)amino)-4-(4-fluorophenyl)thiazole-5-carbonitrile

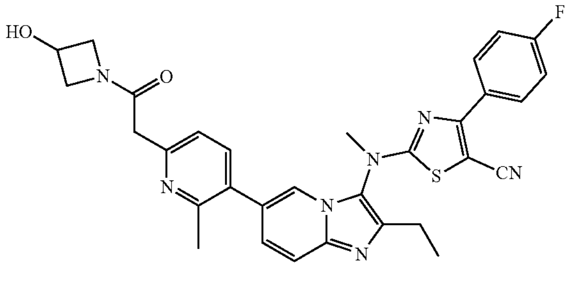 [SMILES: CCc1nc2ccc(-c3ccc(CC(=O)N4CC(O)C4)nc3C)cn2c1N(C)c1nc(-c2ccc(F)cc2)c(C#N)s1]

Specific method of Step 6f: 2-((2-ethyl-6-(6-(2-(3-hydroxyazetidin-1-yl)-2-oxoethyl)-2-methylpyridin-3-yl)imidazo[1,2-a]pyridin-3-yl)(methyl)amino)-4-(4-fluorophenyl)thiazole-5-carbonitrile (6.2 mg) as an off-white solid was prepared from 2-(5-(3-((5-cyano-4-(4-fluorophenyl)thiazol-2-yl)(methyl)amino)-2-ethylimidazo[1,2-a]pyridin-6-yl)-6-methylpyridin-2-yl)acetic acid (25.6 mg, 0.05 mmol) and azetidin-3-ol (7 mg, 0.1 mmol) according to the method of step 1j in Example 1.

$^1$H NMR (400 MHz, $CDCl_3$): δ 8.12 (dd, J=8.8, 5.4 Hz, 2H), 7.73-7.64 (m, 2H), 7.52-7.47 (m, 1H), 7.32-7.26 (m, 2H), 7.17-7.13 (m, 2H), 4.70-4.64 (m, 1H), 4.56-4.49 (m, 1H), 4.28-4.24 (m, 1H), 4.17-4.13 (m, 1H), 3.90-3.86 (m, 1H), 3.66 (s, 2H), 3.64 (s, 3H), 2.79 (q, J=7.6 Hz, 2H), 2.46 (s, 3H), 1.39 (t, J=7.60 Hz, 3H).

Measured value of MS ($ESI^+$) [$(M+H)^+$]: 582.

Example 7: 2-((2-ethyl-6-(5-(2-(3-hydroxyazetidin-1-yl)-2-oxoethyl)pyridin-2-yl)imidazo[1,2-a]pyridin-3-yl)(methyl)amino)-4-(4-fluorophenyl)thiazole-5-carbonitrile (compound 7)

7

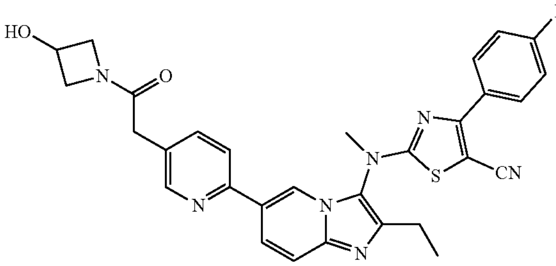

Step 7a: Preparation of 2-bromo-5-(bromomethyl)pyridine

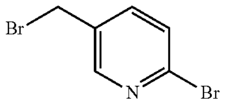

Specific method of Step 7a: 2-bromo-5-methylpyridine (0.5 g, 2.91 mmol) was dissolved into 5 mL of carbon tetrachloride, followed by adding azobisisobutyronitrile (48 mg, 0.29 mmol) and N-bromosuccinimide (0.67 g, 3.78 mmol), then heated to 70° C. to react for 3 hours under the protection of nitrogen. The reaction solution was concentrated, and then 2-bromo-5-(bromomethyl)pyridine (0.4 g) as a colorless oil was obtained by column chromatography purification.

Step 7b: Preparation of 2-(6-bromopyridin-3-yl)acetonitrile

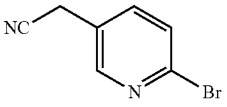

Specific method of Step 7b: 2-bromo-5-(bromomethyl)pyridine (300 mg, 1.2 mmol) was dissolved into 5 mL of acetonitrile, followed by adding tetrabutylammonium cyanide (320 mg, 1.2 mmol), and then reacted at room temperature for 2 hours. The reaction solution was concentrated, added with 20 mL of water, extracted with ethyl acetate (50 mL×3), dried with anhydrous sodium sulfate, filtered, and concentrated. The concentrated reaction solution was purified by column chromatography to obtain 2-(6-bromopyridin-3-yl)acetonitrile (200 mg) as a colorless oil.

Step 7c: Preparation of methyl 2-(6-bromopyridin-3-yl)acetate

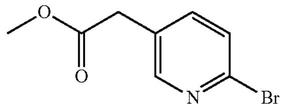

Specific method of Step 7c: 2-(6-bromopyridin-3-yl)acetonitrile (200 mg, 1.02 mmol) was dissolved into 3 mL of methanol, followed by adding thionyl chloride (0.4 mL, 5.10 mmol) under the protection of nitrogen, and the reaction was carried out at room temperature for 5 hours. The reaction solution was added with 20 mL of water, extracted with ethyl acetate (50 mL), dried with anhydrous sodium sulfate, filtered, and concentrated. The concentrated reaction solution was purified by column chromatography to obtain methyl 2-(6-bromopyridin-3-yl)acetate (200 mg) as a colorless oil.

Step 7d: Preparation of methyl 2-(6-(3-((5-cyano-4-(4-fluorophenyl)thiazol-2-yl)(methyl)amino)-2-ethylimidazo[1,2-a]pyridin-6-yl)pyridin-3-yl)acetate

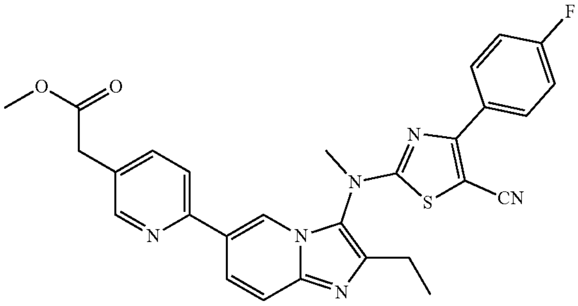 [SMILES: CCc1nc2ccc(-c3ccc(CC(=O)OC)cn3)cn2c1N(C)c1nc(-c2ccc(F)cc2)c(C#N)s1]

Specific method of Step 7d: methyl 2-(6-(3-((5-cyano-4-(4-fluorophenyl)thiazol-2-yl)(methyl)amino)-2-ethylimidazo[1,2-a]pyridin-6-yl)pyridin-3-yl)acetate (70 mg) as a brown solid was prepared from (3-((5-cyano-4-(4-fluorophenyl)thiazol-2-yl)(methyl)amino)-2-ethylimidazo[1,2-a]pyridin-6-yl)boronic acid (150 mg, 0.36 mmol) and methyl 2-(6-bromopyridin-3-yl)acetate (98 mg, 0.43 mmol) according to the method of step 1h in Example 1.

Step 7e: Preparation of 2-(6-(3-((5-cyano-4-(4-fluorophenyl)thiazol-2-yl)(methyl)amino)-2-ethylimidazo[1,2-a]pyridin-6-yl)pyridin-3-yl)acetic acid

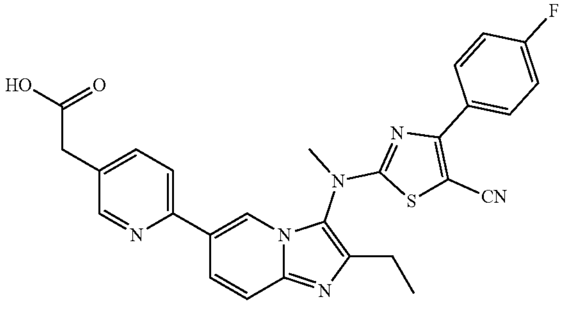 [SMILES: CCc1nc2ccc(-c3ccc(CC(=O)O)cn3)cn2c1N(C)c1nc(-c2ccc(F)cc2)c(C#N)s1]

Specific method of Step 7e: 2-(6-(3-((5-cyano-4-(4-fluorophenyl)thiazol-2-yl)(methyl)amino)-2-ethylimidazo[1,2-a]pyridin-6-yl)pyridin-3-yl)acetic acid (68 mg) as a brown solid was prepared from methyl 2-(6-(3-((5-cyano-4-(4-fluorophenyl)thiazol-2-yl)(methyl)amino)-2-ethylimidazo[1,2-a]pyridin-6-yl)pyridin-3-yl)acetate (70 mg, 0.13 mmol) and sodium hydroxide (16 mg, 0.40 mmol) according to the method of step 1i in Example 1.

Step 7f: Preparation of 2-((2-ethyl-6-(5-(2-(3-hydroxyazetidin-1-yl)-2-oxoethyl)pyridin-2-yl)imidazo[1,2-a]pyridin-3-yl)(methyl)amino)-4-(4-fluorophenyl)thiazole-5-carbonitrile

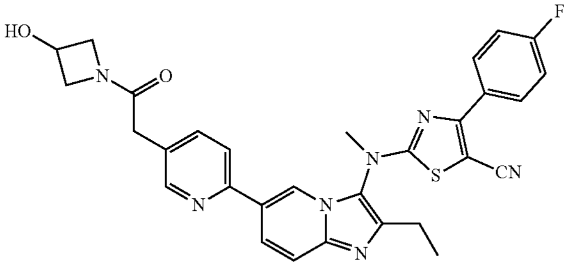 [SMILES: CCc1nc2ccc(-c3ccc(CC(=O)N4CC(O)C4)cn3)cn2c1N(C)c1nc(-c2ccc(F)cc2)c(C#N)s1]

Specific method of Step 7f: 2-((2-ethyl-6-(5-(2-(3-hydroxyazetidin-1-yl)-2-oxoethyl)pyridin-2-yl)imidazo[1,2-a]pyridin-3-yl)(methyl)amino)-4-(4-fluorophenyl)thiazole-5-carbonitrile (6.3 mg) as an off-white solid was prepared from 2-(6-(3-((5-cyano-4-(4-fluorophenyl)thiazol-2-yl)(methyl)amino)-2-ethylimidazo[1,2-a]pyridin-6-yl)pyridin-3-yl)acetic acid (66 mg, 0.13 mmol) and azetidin-3-ol (14 mg, 0.2 mmol) according to the method of step 1j in Example 1.

$^1H$ NMR (400 MHz, $CDCl_3$): δ 8.53 (d, J=8.5 Hz, 2H), 8.17 (dd, J=8.5, 5.4 Hz, 2H), 7.87 (d, J=8.8 Hz, 1H), 7.78 (d, J=7.7 Hz, 1H), 7.69 (dd, J=19.1, 8.8 Hz, 2H), 7.19 (t, J=8.6 Hz, 2H), 4.75-4.61 (m, 1H), 4.44-4.39 (m, 1H), 4.31-4.26 (m, 1H), 4.08-4.06 (m, 1H), 3.92-3.88 (m, 1H), 3.70 (s, 3H), 3.50 (s, 2H), 2.79 (q, J=7.6 Hz, 2H), 1.40 (t, J=7.2 Hz, 3H).

Measured value of MS ($ESI^+$) [$(M+H)^+$]: 568.

Example 8: 2-((2-ethyl-6-(5-(3-hydroxyazetidin-1-carbonyl)pyrazin-2-yl)imidazo[1,2-a]pyridin-3-yl)(methyl)amino)-4-(4-fluorophenyl)thiazole-5-carbonitrile (compound 8)

8

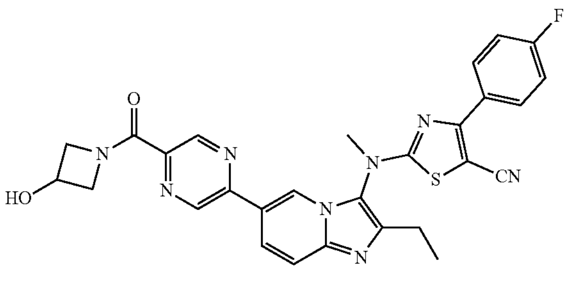

Step 8a: Preparation of methyl 5-(3-((5-cyano-4-(4-fluorophenyl)thiazol-2-yl)(methyl)amino)-2-ethyl-imidazo[1,2-a]pyridin-6-yl)pyrazin-2-carboxylate

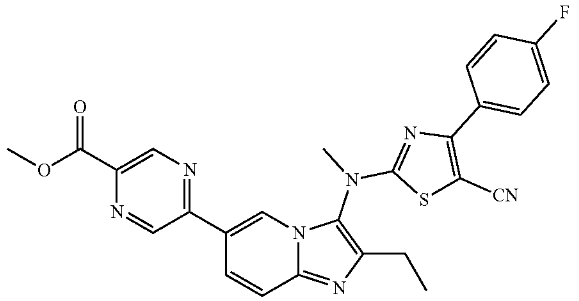 [SMILES: CCc1nc2ccc(-c3cnc(C(=O)OC)cn3)cn2c1N(C)c1nc(-c2ccc(F)cc2)c(C#N)s1]

Specific method of Step 8a: methyl 5-(3-((5-cyano-4-(4-fluorophenyl)thiazol-2-yl)(methyl)amino)-2-ethylimidazo[1,2-a]pyridin-6-yl)pyrazin-2-carboxylate (143 mg) as a brown solid was prepared from (3-((5-cyano-4-(4-fluorophenyl)thiazol-2-yl)(methyl)amino)-2-ethylimidazo[1,2-a]pyridin-6-yl)boronic acid (210 mg, 0.50 mmol) and methyl 5-bromopyrazin-2-carboxylate (216 mg, 1.0 mmol) according to the method of step 1h in Example 1.

Step 8b: Preparation of 5-(3-((5-cyano-4-(4-fluorophenyl)thiazol-2-yl)(methyl)amino)-2-ethylimidazo[1,2-a]pyridin-6-yl)pyrazin-2-carboxylic acid

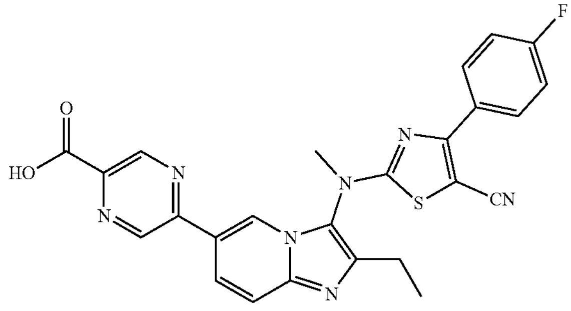 [SMILES: CCc1nc2ccc(-c3cnc(C(=O)O)cn3)cn2c1N(C)c1nc(-c2ccc(F)cc2)c(C#N)s1]

Specific method of Step 8b: 5-(3-((5-cyano-4-(4-fluorophenyl)thiazol-2-yl)(methyl)amino)-2-ethylimidazo[1,2-a]pyridin-6-yl)pyrazin-2-carboxylic acid (139 mg) as a brown solid was prepared from methyl 5-(3-((5-cyano-4-(4-fluorophenyl)thiazol-2-yl)(methyl)amino)-2-ethylimidazo[1,2-a]pyridin-6-yl)pyrazin-2-carboxylate (143 mg, 0.28 mmol) and sodium hydroxide (24 mg, 0.60 mmol) according to the method of step 1i in Example 1 at room temperature.

Step 8c: Preparation of 2-((2-ethyl-6-(5-(3-hydroxyazetidin-1-carbonyl)pyrazin-2-yl)imidazo[1,2-a]pyridin-3-yl)(methyl)amino)-4-(4-fluorophenyl)thiazole-5-carbonitrile

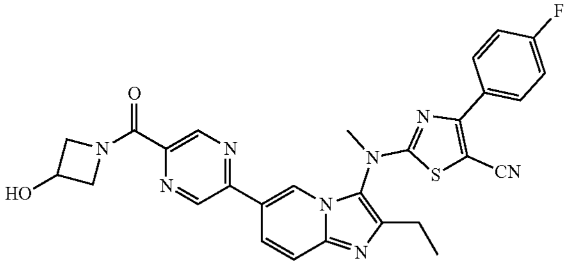 [SMILES: CCc1nc2ccc(-c3cnc(C(=O)N4CC(O)C4)cn3)cn2c1N(C)c1nc(-c2ccc(F)cc2)c(C#N)s1]

Specific method of Step 8c: 2-((2-ethyl-6-(5-(3-hydroxyazetidin-1-carbonyl)pyrazin-2-yl)imidazo[1,2-a]pyridin-3-yl)(methyl)amino)-4-(4-fluorophenyl)thiazole-5-carbonitrile (14.2 mg) as a white solid was prepared from 5-(3-((5-cyano-4-(4-fluorophenyl)thiazol-2-yl)(methyl)amino)-2-ethylimidazolo[1,2-a]pyridin-6-yl)pyrazin-2-carboxylic acid (46 mg, 0.092 mmol) with azetidin-3-ol (14 mg, 0.2 mmol) according to the method of step 1j in Example 1 at room temperature.

f[1]H NMR (400 MHz, $CDCl_3$): δ 9.34 (s, 1H), 8.97 (s, 1H), 8.66 (s, 1H), 8.17 (dd, J=8.8, 5.6 Hz, 2H), 7.95 (d, J=9.6 Hz, 1H), 7.79 (d, J=9.6 Hz, 1H), 7.20 (t, J=8.8 Hz, 2H), 4.99-4.94 (m, 1H), 4.80-4.79 (m, 1H), 4.58-4.51 (m, 2H), 4.13 (dd, J=12.0, 3.2 Hz, 1H), 3.73 (s, 3H), 2.82 (q, J=7.6 Hz, 2H), 1.42 (t, J=7.6 Hz, 3H).

Measured value of MS ($ESI^+$) $[(M+H)^+]$: 555.

Example 9: 2-((2-ethyl-6-(5-(1-(3-hydroxyazetidin-1-yl)-2-methyl-1-oxopropan-2-yl)pyrazin-2-yl)imidazo[1,2-a]pyridin-3-yl)(methyl)amino)-4-(4-fluorophenyl)thiazole-5-carbonitrile (compound 9)

9

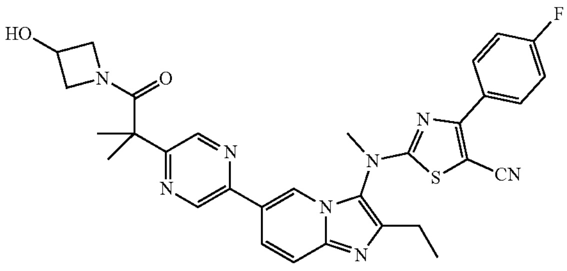

Step 9a: Preparation of ethyl 2-(5-bromopyrazin-2-yl)-2-methylpropionate

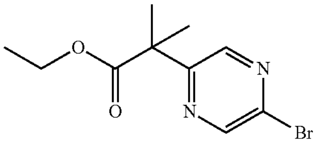

Specific method of Step 9a: at 0° C., 60% sodium hydride (69 mg, 1.73 mmol) was added in batches to a solution of ethyl 2-(5-bromopyrazin-2-yl)-2-acetate (200 mg, 0.82 mmol) in dried DMF (5 mL) at nitrogen atmosphere. After the mixture was stirred at 0° C. for half an hour, methyl iodide (244 mg, 1.73 mmol) was added thereto, and then the reaction solution was stirred at room temperature for 2 h. The reaction was quenched with water (15 mL), extracted with ethyl acetate (20 mL×3), then the combined organic phase was washed with saturated saline (10 mL), dried with anhydrous sodium sulfate, filtered, and concentrated under reduced pressure to afford a crude product. The crude product was purified by column chromatography to afford ethyl 2-(5-bromopyrazin-2-yl)-2-methylpropionate (120 mg) as a yellow oil.

Step 9b: Preparation of ethyl 2-(5-(3-((5-cyano-4-(4-fluorophenyl)thiazol-2-yl)(methyl)amino)-2-ethylimidazo[1,2-a]pyridin-6-yl)pyrazin-2-yl)-2-methylpropionate

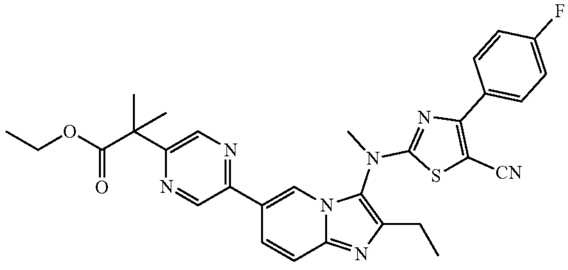 [SMILES: CCOC(=O)C(C)(C)c1cnc(-c2ccc3nc(CC)c(N(C)c4nc(-c5ccc(F)cc5)c(C#N)s4)n3c2)cn1]

Specific method of Step 9b: ethyl 2-(5-(3-((5-cyano-4-(4-fluorophenyl)thiazol-2-yl)(methyl)amino)-2-ethylimidazo[1,2-a]pyridin-6-yl)pyrazin-2-yl)-2-methylpropionate (100 mg) as a brown solid was prepared from (3-((5-cyano-4-(4-fluorophenyl)thiazol-2-yl)(methyl)amino)-2-ethylimidazo[1,2-a]pyridin-6-yl)boronic acid (100 mg, 0.24 mmol) and ethyl 2-(5-bromopyrazin-2-yl)-2-methylpropionate (97 mg, 0.36 mmol) according to the method of step 1h in Example 1.

Step 9c: Preparation of 2-(5-(3-((5-cyano-4-(4-fluorophenyl)thiazol-2-yl)(methyl)amino)-2-ethylimidazo[1,2-a]pyridin-6-yl)pyrazin-2-yl)-2-methylpropionic acid

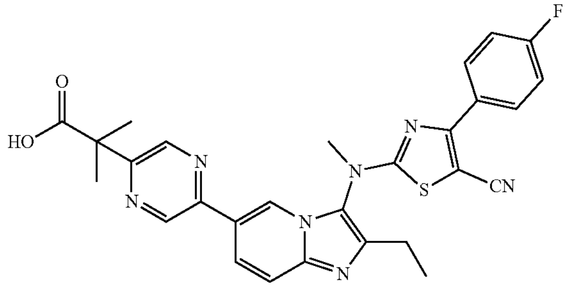 [SMILES: CCc1nc2ccc(-c3cnc(C(C)(C)C(=O)O)cn3)cn2c1N(C)c1nc(-c2ccc(F)cc2)c(C#N)s1]

Specific method of Step 9c: 2-(5-(3-((5-cyano-4-(4-fluorophenyl)thiazol-2-yl)(methyl)amino)-2-ethylimidazo[1,2-a]pyridin-6-yl)pyrazin-2-yl)-2-methylpropionic acid (110 mg) as a brown solid was prepared from ethyl 2-(5-(3-((5-cyano-4-(4-fluorophenyl)thiazol-2-yl)(methyl)amino)-2-ethylimidazolo[1,2-a]pyridin-6-yl)pyrazin-2-yl)-2-methylpropionate (100 mg, 0.18 mmol) and lithium hydroxide monohydrate (15 mg, 0.35 mmol) according to the method of step 5d in Example 5 at room temperature.

Step 9d: Preparation of 2-((2-ethyl-6-(5-(1-(3-hydroxyazetidin-1-yl)-2-methyl-1-oxopropan-2-yl)pyrazin-2-yl)imidazo[1,2-a]pyridin-3-yl)(methyl)amino)-4-(4-fluorophenyl)thiazole-5-carbonitrile

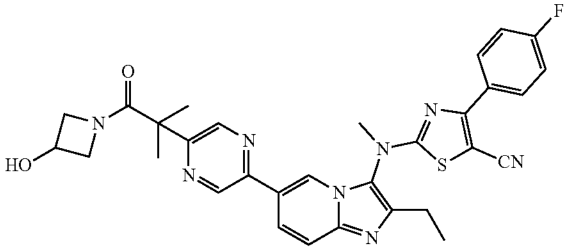 [SMILES: CCc1nc2ccc(-c3cnc(C(C)(C)C(=O)N4CC(O)C4)cn3)cn2c1N(C)c1nc(-c2ccc(F)cc2)c(C#N)s1]

Specific method of Step 9d: 2-((2-ethyl-6-(5-(1-(3-hydroxyazetidin-1-yl)-2-methyl-1-oxopropan-2-yl)pyrazin-2-yl)imidazo[1,2-a]pyridin-3-yl)(methyl)amino)-4-(4-fluorophenyl)thiazole-5-carbonitrile (45 mg) as a white solid was prepared from 2-(5-(3-((5-cyano-4-(4-fluorophenyl)thiazol-2-yl)(methyl)amino)-2-ethylimidazolo[1,2-a]pyridin-6-yl)pyrazin-2-yl)-2-methylpropionic acid (100 mg, 0.18 mmol) and azetidin-3-ol (27 mg, 0.37 mmol) at room temperature according to the method of step 5e in Example 5.

$^1H$ NMR (400 MHz, $CDCl_3$): δ 8.95 (s, 1H), 8.63 (s, 1H), 8.58 (s, 1H), 8.16 (dd, J=8.8, 5.6 Hz, 2H), 7.90 (d, J=9.6 Hz, 1H), 7.76 (d, J=9.2 Hz, 1H), 7.20 (t, J=8.8 Hz, 2H), 4.50-4.48 (m, 1H), 4.24-4.19 (m, 1H), 3.91-3.80 (m, 2H), 3.70 (s, 3H), 3.40-3.30 (m, 1H), 2.81 (q, J=7.6 Hz, 2H), 1.63 (s, 6H), 1.42 (t, J=7.6 Hz, 3H).

Measured value of MS ($ESI^+$) [$(M+H)^+$]: 597.

Example 10: 2-((2-ethyl-6-(3-fluoro-5-(2-(3-hydroxyazetidin-1-yl)-2-oxoethyl)pyridin-2-yl)imidazo[1,2-a]pyridin-3-yl)(methyl)amino)-4-(4-fluorophenyl)thiazole-5-carbonitrile (compound 10)

10

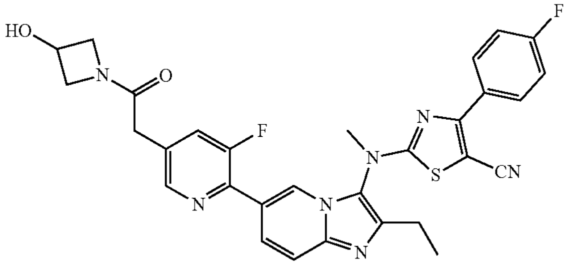

Step 10a: Preparation of 5-(bromomethyl)-2-chloro-3-fluoropyridine

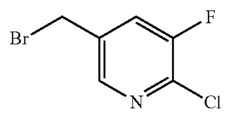

Specific method of Step 10a: 2-chloro-3-fluoro-5-methylpyridine (1.0 g, 6.90 mmol) was dissolved into 10 mL of carbon tetrachloride, followed by adding azobisisobutyronitrile (113 mg, 0.69 mmol) and NBS (1.35 g, 7.59 mmol), then heated to 70° C. to react for 3 hours under the protection of nitrogen. The reaction solution was concentrated, and then 5-(bromomethyl)-2-chloro-3-fluoropyridine (0.45 g) as a colorless oil was obtained by column chromatography purification.

Step 10b: Preparation of 2-(6-chloro-5-fluoropyridin-3-yl)acetonitrile

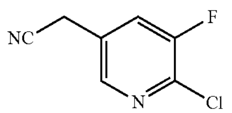 [SMILES: N#CCc1cnc(Cl)c(F)c1]

Specific method of Step 10b: 5-(bromomethyl)-2-chloro-3-fluoropyridine (450 mg, 2.0 mmol) was dissolved into 5 mL of acetonitrile, followed by adding tetrabutylammonium cyanide (644 mg, 2.4 mmol), and then the reaction solution reacted at room temperature for 2 hours. The reaction solution was concentrated, added with 20 mL of water, extracted with ethyl acetate (50 mL×3), dried with anhydrous sodium sulfate, filtered, and concentrated. The concentrated reaction solution was purified by column chromatography to obtain 2-(6-chloro-5-fluoropyridin-3-yl) acetonitrile (275 mg) as a colorless oil.

Step 10c: Preparation of methyl 2-(6-chloro-5-fluoropyridin-3-yl) acetate

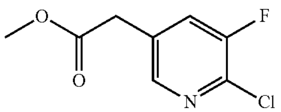

Specific method of Step 10c: 2-(6-chloro-5-fluoropyridin-3-yl)acetonitrile (275 mg, 1.62 mmol) was dissolved into 3 mL of methanol, followed by adding thionyl chloride (0.6 mL, 8.10 mmol) under the protection of nitrogen, then the reaction solution reacted at room temperature for 5 hours. The reaction solution was added with 20 mL of water, extracted with ethyl acetate (50 mL), dried with anhydrous sodium sulfate, filtered, and concentrated. The concentrated reaction solution was purified by column chromatography to obtain methyl 2-(6-chloro-5-fluoropyridin-3-yl)acetate (253 mg) as a colorless oil.

Step 10d: Preparation of methyl 2-(6-(3-((5-cyano-4-(4-fluorophenyl)thiazol-2-yl)(methyl)amino)-2-ethylimidazo[1,2-a]pyridin-6-yl)5-fluoropyridin-3-yl)acetate

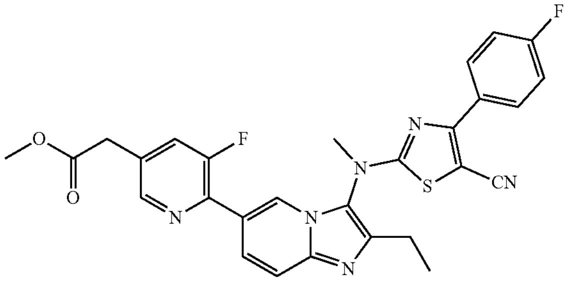 [SMILES: CCc1nc2ccc(-c3ncc(CC(=O)OC)cc3F)cn2c1N(C)c1nc(-c2ccc(F)cc2)c(C#N)s1]

Specific method of Step 10d: methyl 2-(6-(3-((5-cyano-4-(4-fluorophenyl)thiazol-2-yl)(methyl)amino)-2-ethylimidazo[1,2-a]pyridin-6-yl)5-fluoropyridin-3-yl)acetate (110 mg) as a brown solid was prepared from (3-((5-cyano-4-(4-fluorophenyl)thiazol-2-yl)(methyl)amino)-2-ethylimidazo [1,2-a]pyridin-6-yl)boronic acid (351 mg, 0.83 mmol) and methyl 2-(6-chloro-5-fluoropyridin-3-yl)acetate (253 mg, 1.25 mmol) according to the method of step 1h in Example 1.

Step 10e: Preparation of 2-(6-(3-((5-cyano-4-(4-fluorophenyl)thiazol-2-yl)(methyl)amino)-2-ethylimidazo[1,2-a]pyridin-6-yl)-5-fluoropyridin-3-yl) acetic acid

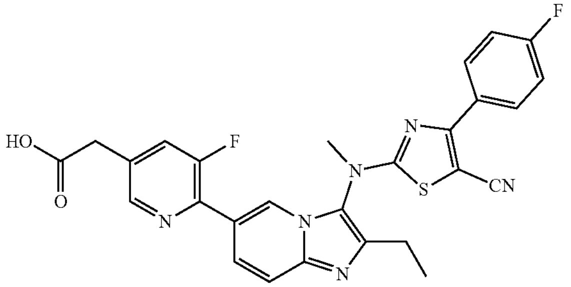 [SMILES: CCc1nc2ccc(-c3ncc(CC(=O)O)cc3F)cn2c1N(C)c1nc(-c2ccc(F)cc2)c(C#N)s1]

Specific method of Step 10e: 2-(6-(3-((5-cyano-4-(4-fluorophenyl)thiazol-2-yl)(methyl)amino)-2-ethylimidazo[1,2-a]pyridin-6-yl)-5-fluoropyridin-3-yl)acetic acid (106 mg) as a brown solid was prepared from methyl 2-(6-(3-((5-cyano-4-(4-fluorophenyl)thiazol-2-yl)(methyl)amino)-2-ethylimidazolo[1,2-a]pyridin-6-yl)-5-fluoropyridin-3-yl)acetate (110 mg, 0.20 mmol) and sodium hydroxide (16 mg, 0.40 mmol) according to the method of step 1i in Example 1.

Step 10f: Preparation of 2-((2-ethyl-6-(3-fluoro-5-(2-(3-hydroxyazetidin-1-yl)-2-oxoethyl)pyridin-2-yl)imidazo[1,2-a]pyridin-3-yl)(methyl)amino)-4-(4-fluorophenyl)thiazole-5-carbonitrile

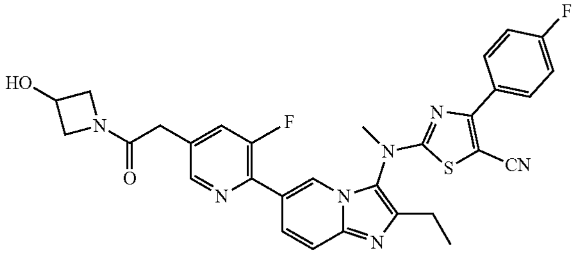 [SMILES: CCc1nc2ccc(-c3ncc(CC(=O)N4CC(O)C4)cc3F)cn2c1N(C)c1nc(-c2ccc(F)cc2)c(C#N)s1]

Specific method of Step 10f: 2-((2-ethyl-6-(3-fluoro-5-(2-(3-hydroxyazetidin-1-yl)-2-oxoethyl)pyridin-2-yl)imidazo[1,2-a]pyridin-3-yl)(methyl)amino)-4-(4-fluorophenyl)thiazole-5-carbonitrile (29.4 mg) as an off-white solid was prepared from 2-(6-(3-((5-cyano-4-(4-fluorophenyl)thiazol-2-yl)(methyl)amino)-2-ethylimidazo[1,2-a]pyridin-6-yl)-5-fluoropyridin-3-yl)acetic acid (106 mg, 0.2 mmol) and azetidin-3-ol (27 mg, 0.37 mmol) according to the method of step 1j in Example 1.

$^{1}$H NMR (400 MHz, $CDCl_3$): δ8.48 (s, 1H), 8.37 (s, 1H), 8.19-8.16 (dd, J=8.8, 5.2 Hz, 2H), 8.05 (d, J=9.6 Hz, 1H), 7.72 (d, J=9.2 Hz, 1H), 7.57 (d, J=12.0 Hz, 1H), 7.19 (t, J=8.8 Hz, 2H), 4.74 (br. s, 1H), 4.45 (t, J=8.4 Hz, 1H), 4.32-4.28 (m, 1H), 4.14-4.09 (m, 1H), 3.95-3.90 (m, 1H), 3.70 (s, 3H), 2.81 (q, J=7.6 Hz, 2H), 2.52 (s, 2H), 1.41 (t, J=7.6 Hz, 3H).

Measured value of MS ($ESI^+$) [$(M+H)^+$]: 586.

Example 11: (S)-2-((2-ethyl-6-(5-(2-(3-hydroxypyrrolidin-1-yl)-2-oxoethyl)pyrazin-2-yl)imidazo[1,2-a]pyridin-3-yl)(methyl)amino)-4-(4-fluorophenyl)thiazole-5-carbonitrile (compound 11)

11

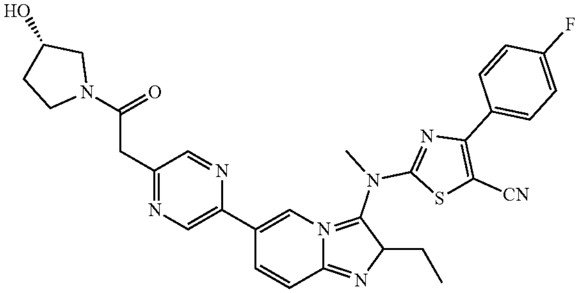

Step 11a: Preparation of (S)-2-((2-ethyl-6-(5-(2-(3-hydroxypyrrolidin-1-yl)-2-oxoethyl)pyrazin-2-yl)imidazo[1,2-a]pyridin-3-yl)(methyl)amino)-4-(4-fluorophenyl)thiazole-5-carbonitrile

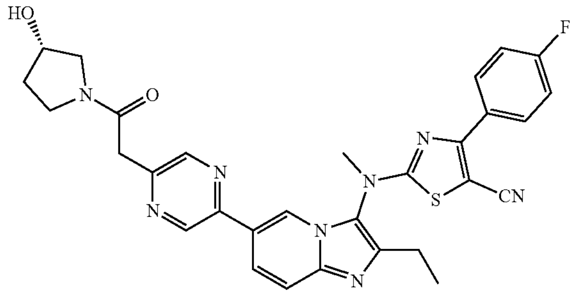 [SMILES: CCc1nc2ccc(-c3cnc(CC(=O)N4CC[C@H](O)C4)cn3)cn2c1N(C)c1nc(-c2ccc(F)cc2)c(C#N)s1]

Specific method of Step 11a: (S)-2-((2-ethyl-6-(5-(2-(3-hydroxypyrrolidin-1-yl)-2-oxoethyl)pyrazin-2-yl)imidazo[1,2-a]pyridin-3-yl)(methyl)amino)-4-(4-fluorophenyl)thiazole-5-carbonitrile (20.5 mg) as an off-white solid was prepared from 2-(5-(3-((5-cyano-4-(4-fluorophenyl)thiazol-2-yl)(methyl)amino)-2-ethylimidazo[1,2-a]pyridin-6-yl)pyrazin-2-yl)acetic acid (40 mg, 0.08 mmol) and (S)-pyrrolidin-3-ol (8.14 mg, 0.093 mmol) according to the method of step 1j in Example 1.

$^{1}$H NMR (400 MHz, $CDCl_3$): δ 8.90 (s, 1H), 8.66 (s, 1H), 8.55 (s, 1H), 8.17 (dd, J=8.4, 5.6 Hz, 2H), 7.90 (d, J=9.2 Hz, 1H), 7.77 (d, J=9.2 Hz, 1H), 7.19 (t, J=8.4 Hz, 2H), 4.63-4.48 (m, 1H), 3.94 (s, 2H), 3.86-3.73 (m, 2H), 3.71 (s, 3H), 3.69-3.63 (m, 2H), 2.81 (q, J=7.6 Hz, 2H), 2.02-1.99 (m, 2H), 1.40 (t, J=7.6 Hz, 3H).

Measured value of MS ($ESI^+$) [$(M+H)^+$]: 583.

Example 12: 2-((2-ethyl-6-(5-(2-(3-(hydroxymethyl)azetidin-1-yl)-2-oxoethyl)pyrazin-2-yl)imidazo[1,2-a]pyridin-3-yl)(methyl)amino)-4-(4-fluorophenyl)thiazole-5-carbonitrile (compound 12)

12

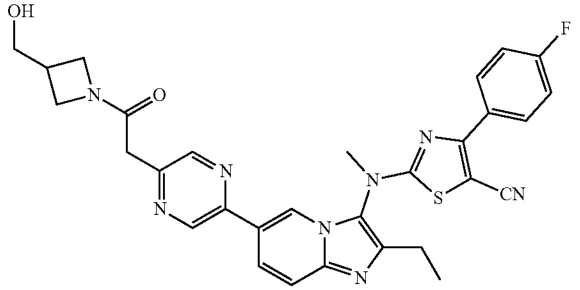

Step 12a: Preparation of 2-((2-ethyl-6-(5-(2-(3-(hydroxymethyl)azetidin-1-yl)-2-oxoethyl)pyrazin-2-yl) imidazo[1,2-a]pyridin-3-yl)(methyl)amino)-4-(4-fluorophenyl)thiazole-5-carbonitrile

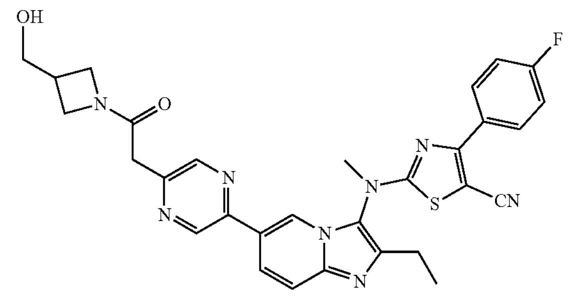 [SMILES: CCc1nc2ccc(-c3cnc(CC(=O)N4CC(CO)C4)cn3)cn2c1N(C)c1nc(-c2ccc(F)cc2)c(C#N)s1]

Specific method of Step 12a: 2-((2-ethyl-6-(5-(2-(3-(hydroxymethyl)azetidin-1-yl)-2-oxoethyl)pyrazin-2-yl)imidazo[1,2-a]pyridin-3-yl)(methyl)amino)-4-(4-fluorophenyl) thiazole-5-carbonitrile (12.5 mg) as an off-white solid was prepared from 2-(5-(3-((5-cyano-4-(4-fluorophenyl)thiazol-2-yl)(methyl)amino)-2-ethylimidazo[1,2-a]pyridin-6-yl) pyrazin-2-yl)acetic acid (40 mg, 0.08 mmol) and 3-(hydroxymethyl)azetidine hydrochloride (11.55 mg, 0.093 mmol) according to the method of step 1j in Example 1.

$^1$H NMR (400 MHz, $CDCl_3$): δ 8.91 (s, 1H), 8.66 (s, 1H), 8.55 (s, 1H), 8.17 (dd, J=8.4, 5.6 Hz, 2H), 7.90 (d, J=9.2 Hz, 1H), 7.76 (d, J=9.2 Hz, 1H), 7.19 (t, J=8.4 Hz, 2H), 4.41-4.30 (m, 1H), 4.17-4.07 (m, 2H), 3.88-3.79 (m, 3H), 3.73 (s, 2H), 3.70 (s, 3H), 2.90-2.86 (m, 1H), 2.82 (q, J=7.6 Hz, 2H), 1.41 (t, J=7.60 Hz, 3H).

Measured value of MS ($ESI^+$) $[(M+H)^+]$: 583.

Example 13: (R)-2-((2-ethyl-6-(5-(2-(3-hydroxypyrrolidin-1-yl)-2-oxoethyl)pyrazin-2-yl)imidazo[1,2-a] pyridin-3-yl)(methyl)amino)-4-(4-fluorophenyl)thiazole-5-carbonitrile (compound 13)

13

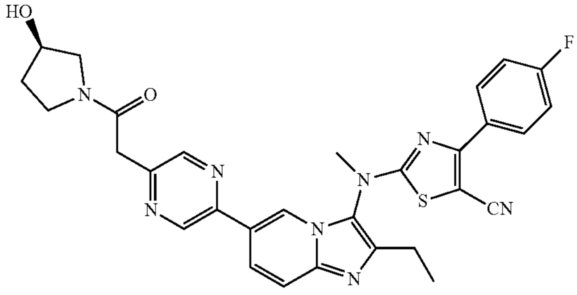

Step 13a: Preparation of (R)-2-((2-ethyl-6-(5-(2-(3-hydroxypyrrolidin-1-yl)-2-oxoethyl)pyrazin-2-yl) imidazo[1,2-a]pyridin-3-yl)(methyl)amino)-4-(4-fluorophenyl)thiazole-5-carbonitrile

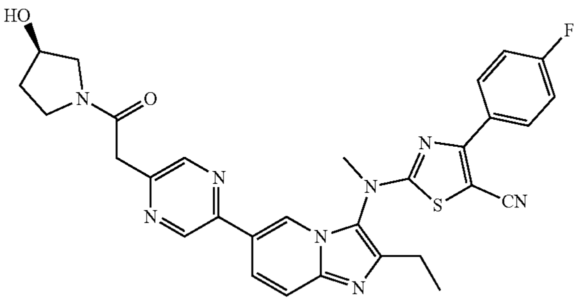 [SMILES: CCc1nc2ccc(-c3cnc(CC(=O)N4CC[C@@H](O)C4)cn3)cn2c1N(C)c1nc(-c2ccc(F)cc2)c(C#N)s1]

Specific method of Step 13a: (R)-2-((2-ethyl-6-(5-(2-(3-hydroxypyrrolidin-1-yl)-2-oxoethyl)pyrazin-2-yl)imidazo [1,2-a]pyridin-3-yl)(methyl)amino)-4-(4-fluorophenyl)thiazole-5-carbonitrile (16 mg) as an off-white solid was prepared from 2-(5-(3-((5-cyano-4-(4-fluorophenyl)thiazol-2-yl)(methyl)amino)-2-ethylimidazo[1,2-a]pyridin-6-yl) pyrazin-2-yl)acetic acid (40 mg, 0.08 mmol) and (R)-pyrrolidin-3-ol (14 mg, 0.16 mmol) according to the method of step 1j in Example 1.

$^1$H NMR (400 MHz, $CDCl_3$): δ 8.90 (s, 1H), 8.67 (s, 1H), 8.55 (s, 1H), 8.17 (dd, J=8.4, 5.6 Hz, 2H), 7.90 (d, J=9.2 Hz, 1H), 7.78-7.76 (m, 1H), 7.19 (t, J=8.4 Hz, 2H), 4.61-4.52 (m, 1H), 3.94 (s, 2H), 3.86-3.73 (m, 2H), 3.73 (s, 3H), 3.69-3.63 (m, 2H), 2.81 (q, J=7.6 Hz, 2H), 2.13-1.97 (m, 2H), 1.41 (t, J=7.6 Hz, 3H).

Measured value of MS ($ESI^+$) $[(M+H)^+]$: 583.

Example 14: 2-(5-(3-((5-cyano-4-(4-fluorophenyl) thiazol-2-yl)(methyl)amino)-2-ethylimidazo[1,2-a] pyridin-6-yl)pyrazin-2-yl)-N-((5-oxopyrrolidin-2-yl) methyl)acetamide (compound 14)

14

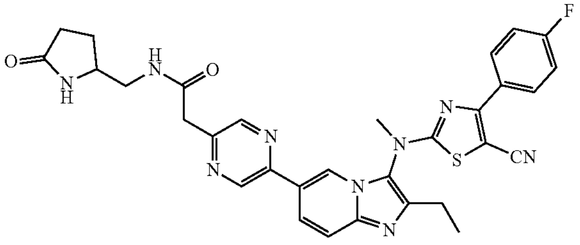

Step 14a: Preparation of 2-(5-(3-((5-cyano-4-(4-fluorophenyl)thiazol-2-yl)(methyl)amino)-2-ethyl-imidazo[1,2-a]pyridin-6-yl)pyrazin-2-yl)-N-((5-oxopyrrolidin-2-yl)methyl)acetamide

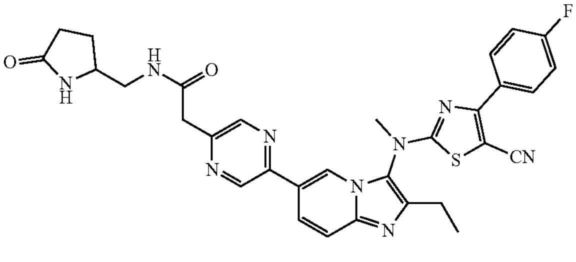 [SMILES: CCc1nc2ccc(-c3cnc(CC(=O)NCC4CCC(=O)N4)cn3)cn2c1N(C)c1nc(-c2ccc(F)cc2)c(C#N)s1]

Specific method of Step 14a: 2-(5-(3-((5-cyano-4-(4-fluorophenyl)thiazol-2-yl)(methyl)amino)-2-ethylimidazo[1,2-a]pyridin-6-yl)pyrazin-2-yl)-N-((5-oxopyrrolidin-2-yl) methyl)acetamide (20 mg) as an off-white solid was prepared from 2-(5-(3-((5-cyano-4-(4-fluorophenyl)thiazol-2-yl)(methyl)amino)-2-ethylimidazo[1,2-a]pyridin-6-yl) pyrazin-2-yl)acetic acid (40 mg, 0.08 mmol) and 5-(aminomethyl)pyrrolidin-2-one (18 mg, 0.16 mmol) according to the method of step 1j in Example 1.

$^1$H NMR (400 MHz, $CDCl_3$): δ 8.83-8.79 (m, 1H), 8.62-8.51 (m, 2H), 8.16 (dd, J=8.5, 5.4 Hz, 2H), 7.89 (d, J=9.3 Hz, 1H), 7.75 (d, J=7.5 Hz, 1H), 7.70-7.55 (m, 1H), 7.18 (t, J=8.6 Hz, 2H), 6.93-6.79 (m, 1H), 3.91-3.90 (m, 1H), 3.77 (s, 2H), 3.71 (s, 3H), 3.59-3.49 (m, 1H), 3.26-3.16 (m, 1H), 2.81 (q, J=7.6 Hz, 2H), 2.32-2.17 (m, 2H), 1.84-1.73 (m, 2H), 1.41 (t, J=7.6 Hz, 3H).

Measured value of MS ($ESI^+$) [$(M+H)^+$]: 610.

Example 15: 5-(3-((5-cyano-4-(4-fluorophenyl)thiazol-2-yl)(methyl)amino)-2-ethylimidazo[1,2-a]pyridin-6-yl)-N-(2-azaspiro[3.3]heptan-6-yl)pyrazin-2-carboxamide (compound 15)

15

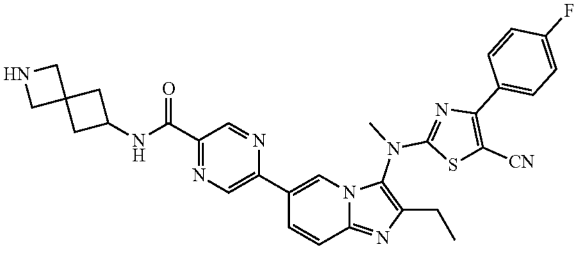

Step 15a: Preparation of tert-butyl 6-(5-(3-((5-cyano-4-(4-fluorophenyl)thiazol-2-yl)(methyl)amino)-2-ethylimidazo[1,2-a]pyridin-6-yl)pyrazine-2-carboxamido)-2-azaspiro[3.3]heptane-2-carboxylate

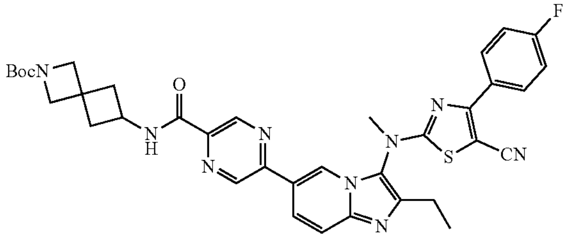 [SMILES: CCc1nc2ccc(-c3cnc(C(=O)NC4CC5(C4)CN(C(=O)OC(C)(C)C)C5)cn3)cn2c1N(C)c1nc(-c2ccc(F)cc2)c(C#N)s1]

Specific method of Step 15a: tert-butyl 6-(5-(3-((5-cyano-4-(4-fluorophenyl)thiazol-2-yl)(methyl)amino)-2-ethylimidazo[1,2-a]pyridin-6-yl)pyrazin-2-carboxamido)-2-azaspiro[3.3]heptane-2-carboxylate (32 mg) as an off-white solid was prepared from 5-(3-((5-cyano-4-(4-fluorophenyl)thiazol-2-yl)(methyl)amino)-2-ethylimidazo[1,2-a]pyridin-6-yl)pyrazine-2-carboxylic acid (40 mg, 0.08 mmol) and tert-butyl 6-amino-2-azaspiro[3.3]heptane-2-carboxylate (34 mg, 0.16 mmol) according to the method of step 1j in Example 1.

Step 15b: Preparation of 5-(3-((5-cyano-4-(4-fluorophenyl)thiazol-2-yl)(methyl)amino)-2-ethylimidazo[1,2-a]pyridin-6-yl)-N-(2-azaspiro[3.3]heptan-6-yl)pyrazin-2-carboxamide

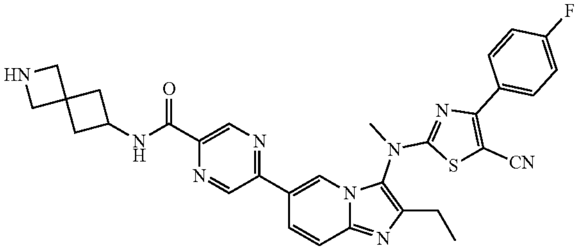 [SMILES: CCc1nc2ccc(-c3cnc(C(=O)NC4CC5(CNC5)C4)cn3)cn2c1N(C)c1nc(-c2ccc(F)cc2)c(C#N)s1]

Specific method of Step 15b: trifluoroacetic acid (2 ml) was added to a solution of tert-butyl 6-(5-(3-((5-cyano-4-(4-fluorophenyl)thiazol-2-yl)(methyl)amino)-2-ethylimidazo[1,2-a]pyridin-6-yl)pyrazine-2-carboxamide)-2-azaspiro[3.3]heptane-2-carboxylate (32 mg, 0.046 mmol) in dichloromethane (1 ml), which was stirred at room temperature for 1 h, quenched with saturated aqueous sodium bicarbonate solution, and extracted with dichloromethane (10 mL×3). The combined organic phase was washed with saturated saline (20 mL), dried with anhydrous sodium sulfate, filtered, and concentrated under reduced pressure to afford a crude product. The crude product was purified by flash column chromatography to afford 5-(3-((5-cyano-4-(4-fluorophenyl)thiazol-2-yl)(methyl)amino)-2-ethylimidazo[1,2-a]pyridin-6-yl)-N-(2-azaspiro[3.3]heptan-6-yl)pyrazin-2-carboxamide (10.4 mg) as a white solid.

$^1$H NMR (400 MHz, DMSO $d_6$): δ 9.38 (s, 1H), 8.91 (s, 1H), 8.68 (s, 1H), 8.19-8.16 (m, 2H), 7.94 (d, J=9.2 Hz, 1H), 7.81 (t, J=10.0 Hz, 1H), 7.20 (t, J=8.8 Hz, 2H), 4.50-4.44 (m,

1H), 3.82 (s, 2H), 3.73 (s, 3H), 3.70 (s, 2H), 2.81 (q, J=7.6 Hz, 2H), 2.79-2.74 (m, 2H), 2.27-2.19 (m, 2H), 1.42 (t, J=7.6 Hz, 3H).

Measured value of MS (ESI$^+$) [(M+H)$^+$]: 594.

Example 16: 2-((2-ethyl-6-(5-fluoro-6-(3-hydroxyazetidin-1-carbonyl)pyridin-3-yl)imidazo[1,2-a]pyridin-3-yl)(methyl)amino)-4-(4-fluorophenyl) thiazole-5-carbonitrile (compound 16)

16

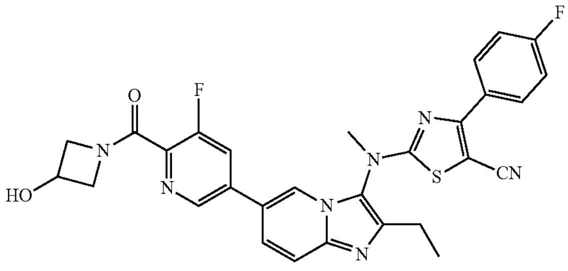

Step 16a: Preparation of (5-fluoro-6-(methoxycarbonyl)pyridin-3-yl)boronic acid

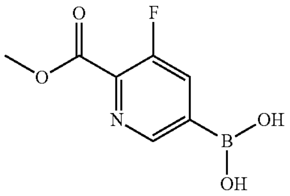

Specific method of Step 16a: (5-fluoro-6-(methoxycarbonyl)pyridin-3-yl)boronic acid (140 mg) as a black oil was prepared from methyl 5-bromo-3-fluoropicolinate (100 mg, 0.429 mmol) and bis(pinacolato)diboron (130 mg, 0.52 mmol) according to the method of step 2a in Example 2.

Step 16b: Preparation of methyl 5-(3-((5-cyano-4-(4-fluorophenyl)thiazol-2-yl)(methyl)amino)-2-ethylimidazo[1,2-a]pyridin-6-yl)-3-fluoropicolinate

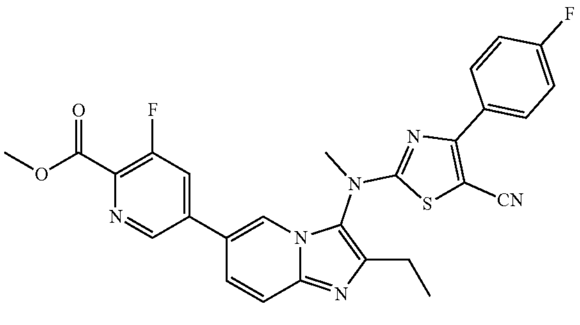 [SMILES: CCc1nc2ccc(-c3cnc(C(=O)OC)c(F)c3)cn2c1N(C)c1nc(-c2ccc(F)cc2)c(C#N)s1]

Specific method of Step 16b: methyl 5-(3-((5-cyano-4-(4-fluorophenyl)thiazol-2-yl)(methyl)amino)-2-ethylimidazo[1,2-a]pyridin-6-yl)-3-fluoropicolinate (150 mg) as a yellow solid was prepared from (5-fluoro-6-(methoxycarbonyl)pyridin-3-yl)boronic acid (85 mg, 0.43 mmol) and 2-((6-bromo-2-ethylimidazo[1,2-a]pyridin-3-yl)(methyl)amino)-4-(4-fluorophenyl)thiazole-5-carbonitrile (391 mg, 0.86 mmol) according to the method of step 1h in Example 1.

Step 16c: Preparation of 5-(3-((5-cyano-4-(4-fluorophenyl)thiazol-2-yl)(methyl)amino)-2-ethylimidazo [1,2-a]pyridin-6-yl)3-fluoropicolinic acid

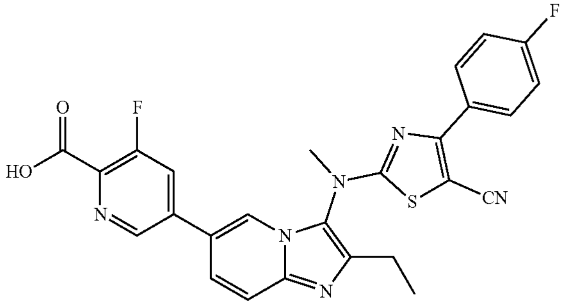 [SMILES: CCc1nc2ccc(-c3cnc(C(=O)O)c(F)c3)cn2c1N(C)c1nc(-c2ccc(F)cc2)c(C#N)s1]

Specific method of Step 16c: 5-(3-((5-cyano-4-(4-fluorophenyl)thiazol-2-yl)(methyl)amino)-2-ethylimidazo[1,2-a] pyridin-6-yl)3-fluoropicolinic acid (191 mg) as a white solid was prepared from methyl 5-(3-((5-cyano-4-(4-fluorophenyl)thiazol-2-yl)(methyl)amino)-2-ethylimidazolo[1,2-a] pyridin-6-yl)-3-fluoropicolinate (150 mg, 0.28 mmol) and sodium hydroxide (24 mg, 0.60 mmol) according to the method of step 1i in Example 1.

Step 16d: Preparation of 2-((2-ethyl-6-(5-fluoro-6-(3-hydroxyazetidin-1-carbonyl)pyridin-3-yl)imidazo [1,2-a]pyridin-3-yl)(methyl)amino)-4-(4-fluorophenyl)thiazole-5-carbonitrile

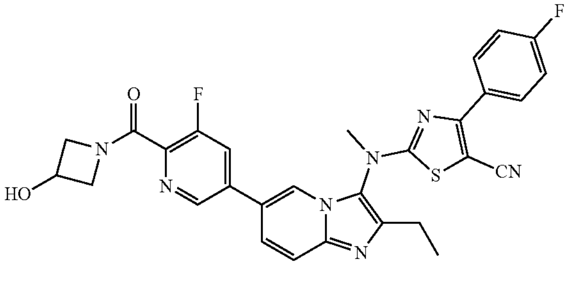 [SMILES: CCc1nc2ccc(-c3cnc(C(=O)N4CC(O)C4)c(F)c3)cn2c1N(C)c1nc(-c2ccc(F)cc2)c(C#N)s1]

Specific method of Step 16d: 2-((2-ethyl-6-(5-fluoro-6-(3-hydroxyazetidin-1-carbonyl)pyridin-3-yl)imidazo[1,2-a] pyridin-3-yl)(methyl)amino)-4-(4-fluorophenyl)thiazole-5-carbonitrile (65.8 mg) as a white solid was prepared from 5-(3-((5-cyano-4-(4-fluorophenyl)thiazol-2-yl)(methyl) amino)-2-ethylimidazo[1,2-a]pyridin-6-yl)-3-fluoropicolinic acid (146 mg, 0.28 mmol) and azetidin-3-ol (27 mg, 0.37 mmol) according to the method of step 1j in Example 1.

$^1$H NMR (400 MHz, $CDCl_3$): δ 8.59 (s, 1H), 8.15-8.11 (m, 2H), 8.00 (s, 1H), 7.80 (d, J=9.2 Hz, 1H), 7.66 (d, J=10.4 Hz, 1H), 7.52 (d, J=8.8 Hz, 1H), 7.16 (t, J=8.8 Hz, 2H), 4.74 (s, 1H), 4.60-4.56 (m, 1H), 4.51-4.46 (m, 1H), 4.27-4.23 (m, 1H), 4.11-4.07 (m, 1H), 3.68 (s, 3H), 2.79 (q, J=7.6 Hz, 2H), 1.39 (t, J=7.6 Hz, 3H).

Measured value of MS ($ESI^+$) [$(M+H)^+$]: 572.

Example 17: 2-((5-(2-(1,1-dioxidoisothiazolidin-2-yl)pyrimidin-5-yl)-2-ethyl-2H-pyrazolo[4,3-b]pyridin-3-yl)(ethyl)amino)-4-(4-fluorophenyl)thiazole-5-carbonitrile (compound 17)

17

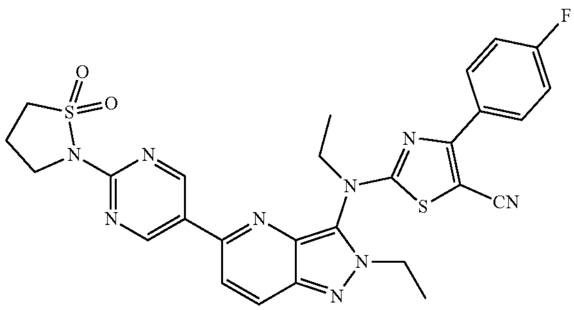

Step 17a: Preparation of 2-bromo-5-fluoro-1-hydroxypyridin-1-ium

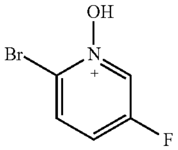

Specific method of Step 17a: hydrogen peroxide (80 mL) was added to a solution of 2-bromo-5-fluoropyridine (50.0 g, 36.78 mmol) in trifluoroacetic acid (400 mL) at room temperature. The mixture was stirred at 85° C. for 10 hours, then cooled to room temperature, added with sodium thiosulfate (120 g), quenched, and filtered. The mother liquor was adjusted to pH 7-8 with an aqueous sodium hydroxide solution and extracted with dichloromethane (800 ml×3). The organic phase was washed with saturated saline, dried with anhydrous sodium sulfate, filtered, and concentrated to afford 2-bromo-5-fluoro-1-hydroxypyridin-1-ium (50 g) as a grey solid.

Step 17b: Preparation of 6-bromo-3-fluoro-2-cyanopyridine

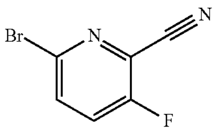

Specific method of Step 17b: triethylamine (126 g, 1.25 mol) and trimethylcyanosilane (125 g, 1.25 mol) were added to a solution of 2-bromo-5-fluoro-1-hydroxypyridin-1-ium (50 g, 0.25 mol) in acetonitrile (400 mL) at room temperature. The mixture was heated to 90° C. and reacted for 12 hours, then concentrated, and the crude product was purified by flash column chromatography to afford 6-bromo-3-fluoro-2-cyanopyridine (22 g) as a white-like solid.

Step 17c: Preparation of 5-bromo-2-ethyl-2H-pyrazolo[4,3-b]pyridine-3-amine

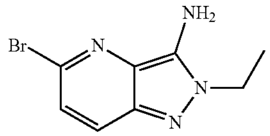

Specific method of Step 17c: potassium carbonate (53 g, 0.38 mol) was added to a solution of 6-bromo-3-fluoro-2-cyanopyridine (22 g, 0.11 mol) and ethylhydrazine oxalate (25 g, 0.16 mol) in dimethyl sulfoxide (110 ml), then heated to 110° C. to react for 2 h. The reaction solution was cooled to room temperature, diluted with ethyl acetate (800 ml), and the organic phase was washed with water (200 ml×3) and saturated saline (200 ml), respectively, dried, filtered, and concentrated. The crude product was purified by flash column chromatography to afford 5-bromo-2-ethyl-2H-pyrazolo[4,3-b]pyridin-3-amine (3.2 g) as a yellow solid.

Step 17d: Preparation of 2-((5-bromo-2-ethyl-2H-pyrazolo[4,3-b]pyridin-3-yl)amino)-4-(4-fluorophenyl)thiazole-5-carbonitrile

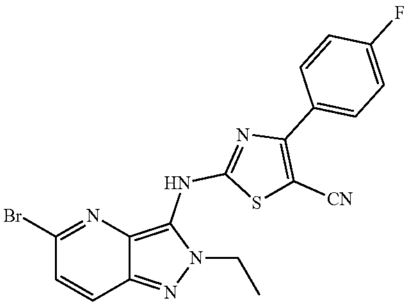

Specific method of Step 17d: at 0° C., 60% sodium hydride (1.1 g, 26.4 mmol) was added in batches to a solution of 5-bromo-2-ethyl-2H-pyrazolo[4,3-b]pyridin-3-amine (3.2 g, 13 mmol) in DMF (30 mL) at nitrogen atmosphere. The reaction solution was stirred at 0° C. for 15 min, and then added in batches with 2-chloro-4-(4-fluorophenyl)thiazole-5-carbonitrile (3.4 g, 14.5 mmol). The mixture continued to react at room temperature for 1 h, then was quenched with water (60 mL) and filtered. The filter cake was washed with ethyl acetate (20 mL×3) and then dried to afford 2-((5-bromo-2-ethyl-2H-pyrazolo[4,3-b]pyridin-3-yl)amino)-4-(4-fluorophenyl)thiazole-5-carbonitrile (6 g) as a yellow solid.

Step 17e: Preparation of 2-((5-bromo-2-ethyl-2H-pyrazolo[4,3-b]pyridin-3-yl)(ethyl)amino)-4-(4-fluorophenyl)thiazole-5-carbonitrile

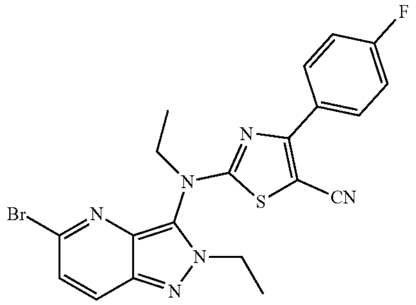 [SMILES: CCN(c1nc(-c2ccc(F)cc2)c(C#N)s1)c1c2nc(Br)ccc2nn1CC]

Specific method of Step 1a: at 0° C., 60% sodium hydride (1.4 g, 33.9 mmol) was added in batches to a solution of 2-((5-bromo-2-ethyl-2H-pyrazolo[4,3-b]pyridin-3-yl) amino)-4-(4-fluorophenyl)thiazole-5-carbonitrile (6 g, 13.6 mmol) in DMF (50 mL) at nitrogen atmosphere. The reaction solution was stirred at room temperature for 0.5 h, and then iodoethane (4.2 g, 27.1 mmol) was added thereto. The mixture continued to react at room temperature for 3 h, then was quenched with water (200 mL), extracted with ethyl acetate (100 mL×3), and then the combined organic phase was washed with saturated saline (50 mL), dried with anhydrous sodium sulfate, filtered, and concentrated under reduced pressure to afford a crude product. The crude product was purified by flash column chromatography to afford 2-((5-bromo-2-ethyl-2H-pyrazolo[4,3-b]pyridin-3-yl) (ethyl)amino)-4-(4-fluorophenyl)thiazole-5-carbonitrile (5.5 g) as a yellow solid.

Step 17f: Preparation of 2-(5-bromopyrimidin-2-yl)isothiazolidine 1,1-dioxide

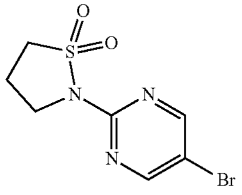 [SMILES: O=S1(=O)CCCN1c1ncc(Br)cn1]

Specific method of Step 17f: tris(dibenzylideneacetone) dipalladium (277 mg, 0.30 mmol), 2-(di-tert-butylphosphine)biphenyl (180 mg, 0.61 mmol), 4,5-bis(diphenylphosphino)-9,9-dimethylxanthene (350 mg, 0.61 mmol) and cesium carbonate (3.94 g, 12.11 mmol) were added to a solution of 3-chloropropane-1-sulfonamide (1.85 g, 7.87 mmol) and 2,5-dibromopyrimidine (954 mg, 6.05 mmol) in tert-butanol (10 mL) under nitrogen atmosphere. The mixture was stirred at 100° C. for 4 h, diluted with water (40 mL) and ethyl acetate (3 mL), stirred at room temperature for 10 min and then filtered, and the filter cake was washed with water, then washed with ethyl acetate/petroleum ether (1:5, 10 mL×2), and dried to afford 2-(5-bromopyrimidin-2-yl)isothiazolidine 1,1-dioxide (1.5 g).

Step 17g: Preparation of (2-(1,1-dioxidoisothiazolidin-2-yl)pyrimidin-5-yl)boronic acid

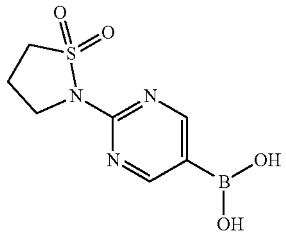 [SMILES: O=S1(=O)CCCN1c1ncc(B(O)O)cn1]

Specific method of Step 17g: [1,1'-bis(diphenylphosphino)ferrocene]palladium dichloride (661 mg, 0.9 mmol) was added to a solution of 2-(5-bromopyrimidin-2-yl)isothiazolidine 1,1-dioxide (5 g, 18.0 mmol), bis(pinacolato) diboron (5.0 g, 19.8 mmol) and potassium acetate (5.3 g, 54.1 mmol) in 1,4-dioxane (50 mL) under the protection of nitrogen. The mixture was heated to 85° C. with stirring for 2 h, then diluted with water (80 mL) and extracted with ethyl acetate (100 mL×2). The combined organic phase was washed with saturated saline (100 mL), dried with anhydrous sodium sulfate, filtered, and concentrated to afford (2-(1,1-dioxidoisothiazolidin-2-yl)pyrimidin-5-yl)boronic acid (5 g) as a brown oily matter.

Step 17h: Preparation of 2-((5-(2-(1,1-dioxidoisothiazolidin-2-yl)pyrimidin-5-yl)-2-ethyl-2H-pyrazolo [4,3-b]pyridin-3-yl)(ethyl)amino)-4-(4-fluorophenyl) thiazole-5-carbonitrile

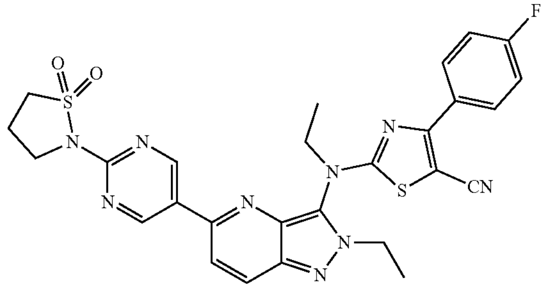 [SMILES: CCN(c1nc(-c2ccc(F)cc2)c(C#N)s1)c1c2nc(-c3cnc(N4CCCS4(=O)=O)nc3)ccc2nn1CC]

Specific method of Step 17h: [1,1'-bis(diphenylphosphino)ferrocene]palladium dichloride (389 mg, 0.53 mmol) and potassium phosphate (2.3 g, 17.0 mmol) were added to a solution of 2-((5-bromo-2-ethyl-2H-pyrazolo[4,3-b]pyridin-3-yl)(ethyl)amino)-4-(4-fluorophenyl)thiazole-5-carbonitrile (5 g, 10.6 mmol) and (2-(1,1-dioxidoisothiazolidin-2-yl)pyrimidin-5-yl)boronic acid (3.1 g, 12.8 mmol) in 1,4-dioxane (50 mL) and water (7 mL) under nitrogen atmosphere. The mixture was stirred at 75° C. for 2 h, then diluted with water (50 mL) and extracted with ethyl acetate (50 mL×3). The combined organic phase was washed with saturated saline (100 mL), dried with anhydrous sodium sulfate, filtered, and concentrated under reduced pressure to afford a crude product. The crude product was purified by flash column chromatography to afford methyl 2-(4-(3-((5-cyano-4-(4-fluorophenyl)thiazol-2-yl)(methyl)amino)-2-ethylimidazo[1,2-a]pyridin-6-yl)phenyl)acetate (4.5 g) as a brown solid.

$^1H$ NMR (400 MHz, DMSO-$d_6$): δ9.26 (s, 2H), 8.20 (d, J=9.2 Hz, 1H), 8.13 (dd, J=8.8, 5.2 Hz, 2H), 7.70 (d, J=9.2 Hz, 1H), 7.17 (t, J=8.4 Hz, 2H), 4.50-4.65 (m, 1H), 4.44 (q, J=7.2 Hz, 2H), 4.12 (t, J=6.4 Hz, 2H), 3.98-3.84 (m, 1H), 3.50 (q, J=7.2 Hz, 2H), 2.57-2.51 (m, 2H), 1.68 (t, J=7.2 Hz, 3H), 1.48 (t, J=7.2 Hz, 3H).

Measured value of MS ($ESI^+$) [$(M+H)^+$]: 590.

Example 18: 2-((5-(2-(1,1-dioxidoisothiazolidin-2-yl)pyrimidin-5-yl)-2-ethyl-pyrazolo[1,5-a]pyrimidin-3-yl)(ethyl)amino)-4-(4-fluorophenyl)thiazole-5-carbonitrile (compound 18)

18

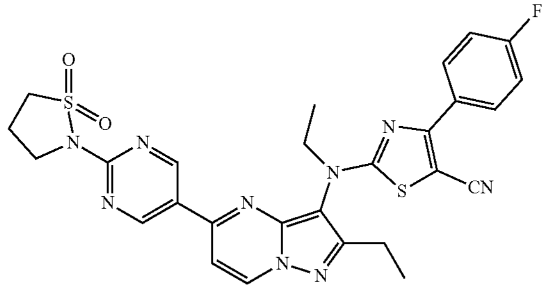

Step 18a: Preparation of 2-ethylpyrazolo[1,5-a]pyrimidin-5(4H)-one

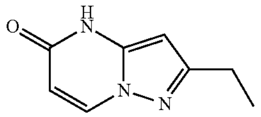

Specific method of Step 18a: sodium ethoxide (9.2 g, 135 mmol) was added to a solution of 3-ethyl-1H-pyrazol-5-amine (5 g, 45 mmol) and 1,3-dimethylpyrimidine-2,4(1H, 3H)-dione (7.6 g, 54 mmol) in ethanol (50 mL) at room temperature. The mixture was stirred at 90° C. for 5 hours, then cooled to room temperature, concentrated, and added with diluted hydrochloric acid (2 M) to adjust pH to 2-3. After filtration, the filter cake was dried to afford 2-ethylpyrazolo[1,5-a]pyrimidin-5(4H)-one (5 g) as a white solid.

Step 18b: Preparation of 2-ethyl-3-nitropyrazolo[1,5-a]pyrimidin-5(4H)-one

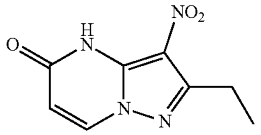

Specific method of Step 18b: at 0° C., concentrated nitric acid (2.2 ml) was slowly added dropwise to a solution of 2-ethylpyrazolo[1,5-a]pyrimidin-5(4H)-one (5 g, 0.25 mol) in concentrated sulfuric acid (20 mL). The mixture continued to react at 0° C. for 2 h, then the reaction solution was slowly added into ice water for quenching, filtered and dried to afford 2-ethyl-3-nitropyrazolo[1,5-a]pyrimidin-5(4H)-one (5 g) as a light yellow solid.

Step 18c: Preparation of 5-chloro-2-ethyl-3-nitropyrazolo[1,5-a]pyrimidine

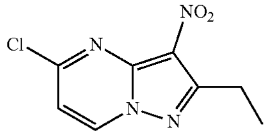

Specific method of Step 18c: N,N-dimethylaniline (4.4 g, 36 mol) was added to a solution of 2-ethyl-3-nitropyrazolo [1,5-a]pyrimidin-5(4H)-one (5 g, 24 mol) in phosphorus oxychloride (30 ml), and the reaction was heated to 90° C. to react for 2 h. The reaction solution was cooled to room temperature, concentrated, quenched with water and extracted with ethyl acetate (100 ml), then the organic phase was washed with 1 M of sodium bicarbonate solution (40 ml) and saturated saline (40 ml), respectively, dried, filtered, and concentrated to afford 5-chloro-2-ethyl-3-nitropyrazole [1,5-a]pyrimidine (4.5 g) as a yellow solid.

Step 18d: Preparation of 5-chloro-2-ethylpyrazolo [1,5-a]pyrimidin-3-amine

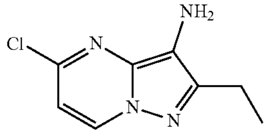

Specific method of Step 18d: iron powders (1.1 g, 26.4 mmol) and saturated ammonium chloride solution (20 ml) were added to a solution of 5-chloro-2-ethyl-3-nitropyrazolo [1,5-a]pyrimidine (4.5 g, 13 mmol) in ethanol (40 mL). The reaction solution is heated to 45° C. and reacted for 2 hours, then filtered, and concentrated. The residue was extracted with ethyl acetate (50 mL×3) and the combined organic phase was washed with saturated saline, dried and concentrated to afford a crude product. The crude product was purified by flash column chromatography to afford 5-chloro-2-ethylpyrazolo[1,5-a]pyrimidin-3-amine (3 g) as a yellow solid.

Step 18e: Preparation of 2-((5-chloro-2-ethylpyrazolo[1,5-a]pyrimidin-3-yl)amino)-4-(4-fluorophenyl) thiazole-5-carbonitrile

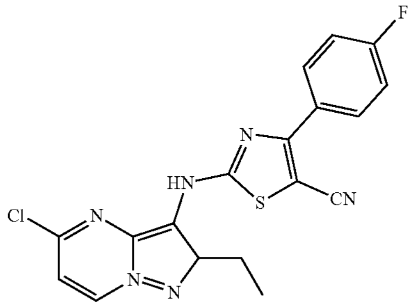

Specific method of Step 18e: at 0° C., 60% sodium hydride (1.2 g, 30.1 mmol) was added in batches to a solution of 5-chloro-2-ethylpyrazolo[1,5-a]pyrimidin-3-amine (3.0 g, 15 mmol) in THE (30 mL) under nitrogen atmosphere. The reaction solution was stirred at 0° C. for 15 minutes, then added in batches with 2-chloro-4-(4-fluorophenyl)thiazole-5-carbonitrile (4.3 g, 18.4 mmol). The mixture continued to react at 90° C. for 6 hours, then was quenched with water (60 mL), extracted with ethyl acetate (30 mL×3), and then the combined organic phase was washed with saturated saline (50 mL), dried, filtered, and concentrated under reduced pressure to afford a crude product. The crude product was purified by flash column chromatography to afford 2-((5-chloro-2-ethylpyrazolo[1,5-a]pyrimidin-3-yl)amino)-4-(4-fluorophenyl)thiazole-5-carbonitrile (600 mg) as a yellow solid.

Step 18f: Preparation of 2-((5-chloro-2-ethylpyrazolo[1,5-a]pyrimidin-3-yl)(ethyl)amino)-4-(4-fluorophenyl)thiazole-5-carbonitrile

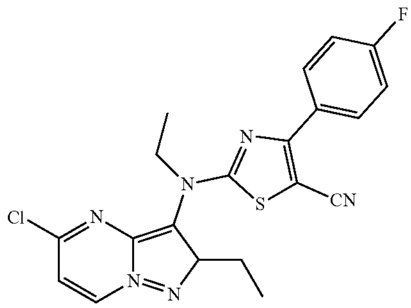

Specific method of Step 18f: at 0° C., cesium carbonate (733 mg, 2.2 mmol) was added to a solution of 2-((5-chloro-2-ethylpyrazolo[1,5-a]pyrimidin-3-yl)amino)-4-(4-fluorophenyl)thiazole-5-carbonitrile (600 mg, 1.5 mmol) in DMF (6 mL) under nitrogen atmosphere. The reaction solution was stirred at room temperature for 10 min, and then iodoethane (305 mg, 1.9 mmol) was added thereto. The mixture continued to react at room temperature for 2 h, then was quenched with water (20 mL) and extracted with ethyl acetate (20 mL×3), and then the combined organic phase was washed with saline (20 mL), dried, filtered, and concentrated under reduced pressure to afford a crude product. The crude product was purified by flash column chromatography to afford 2-((5-chloro-2-ethylpyrazolo[1,5-a]pyrimidin-3-yl)(ethyl)amino)-4-(4-fluorophenyl)thiazole-5-carbonitrile (400 mg) as a yellow solid.

Step 18g: Preparation of 2-((5-(2-(1,1-dioxidoisothiazolidin-2-yl)pyrimidin-5-yl)-2-ethylpyrazolo[1,5-a]pyrimidin-3-yl)(ethyl)amino)-4-(4-fluorophenyl) thiazole-5-carbonitrile

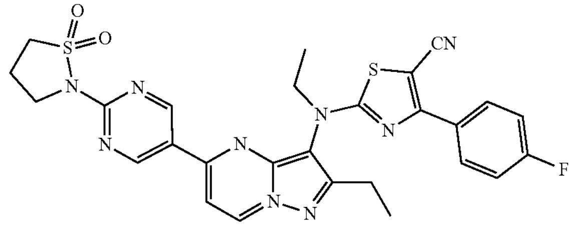

Specific method of Step 18g: 2-((5-(2-(1,1-dioxidoisothiazolidin-2-yl)pyrimidin-5-yl)-2-ethylpyrazolo[1,5-a]pyrimidin-3-yl)(ethyl)amino)-4-(4-fluorophenyl)thiazole-5-carbonitrile (108 mg) as a yellow solid was prepared from 2-((5-chloro-2-ethylpyrazolo[1,5-a]pyrimidin-3-yl)(ethyl) amino)-4-(4-fluorophenyl)thiazole-5-carbonitrile (122 mg, 0.258 mmol) and (2-(1,1-dioxidoisothiazolidin-2-yl)pyrimidin-5-yl)boronic acid (94 mg, 0.388 mmol) according to the method of step 17 h in Example 17 under nitrogen atmosphere.

$^1$H NMR (400 MHz, $CDCl_3$): δ 9.27 (s, 2H), 8.72 (d, J=7.6 Hz, 1H), 8.16 (dd, J=8.8, 5.6 Hz, 2H), 7.26 (br. s., 1H), 7.18 (t, J=8.8 Hz, 2H), 4.36-4.32 (m, 1H), 4.13 (t, J=6.4 Hz, 2H), 3.95-3.83 (m, 1H), 3.51 (t, J=7.2 Hz, 2H), 2.90-2.80 (m, 2H), 2.59-2.54 (m, 2H), 1.47-1.34 (m, 6H).

Measured value of MS ($ESI^+$) [$(M+H)^+$]: 590.

Example 19: 2-((6-(5-(1,1-dioxidoisothiazolidin-2-yl)pyrazin-2-yl)-2-ethylimidazo[1,2-a]pyridin-3-yl) (ethyl)amino)-4-(4-fluorophenyl)thiazole-5-carbonitrile (compound 19)

19

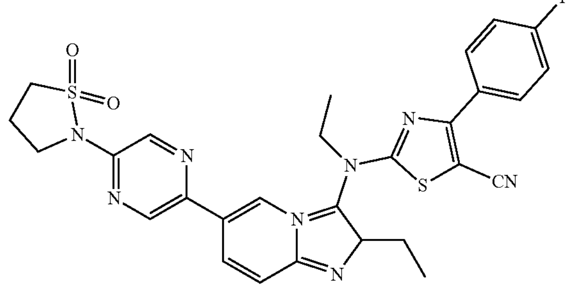

Step 19a: Preparation of 2-(5-bromopyrazin-2-yl)isothiazolidine 1,1-dioxide

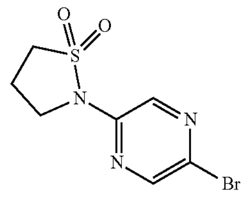 [SMILES: O=S1(=O)CCCN1c1cnc(Br)cn1]

Specific method of Step 19a: 2-(5-bromopyrazin-2-yl) isothiazolidine 1,1-dioxide as a brown solid was prepared from 2,5-dibromopyrazine (900 mg, 3.82 mmol) and 3-chloropropane-1-sulfonamide (400 mg, 2.54 mmol) according to the method of step 17f in Example 17 under nitrogen atmosphere.

Step 19b: Preparation of 2-((6-(5-(1,1-dioxidoisothiazolidin-2-yl)pyrazin-2-yl)-2-ethylimidazo[1,2-a] pyridin-3-yl)(ethyl)amino)-4-(4-fluorophenyl)thiazole-5-carbonitrile

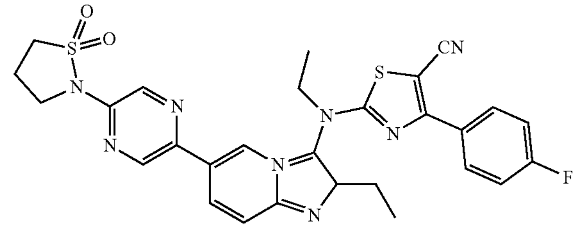

Specific method of Step 19b: 2-((6-(5-(1,1-dioxidoisothiazolidin-2-yl)pyrazin-2-yl)-2-ethylimidazo[1,2-a]pyridin-3-yl)(ethyl)amino)-4-(4-fluorophenyl)thiazole-5-carbonitrile (74.8 mg) as a white solid was prepared from 2-(5-bromopyrazin-2-yl)isothiazolidine 1,1-dioxide (170 mg, 0.614 mmol) and (3-((5-cyano-4-(4-fluorophenyl)thiazol-2-yl) (ethyl)amino)-2-ethylimidazo[1,2-a]pyridin-6-yl)boronic acid (400 mg, 0.921 mmol) according to the method of step 17 h in Example 17 under nitrogen atmosphere.

$^1$H NMR (400 MHz, DMSO-$d_6$): δ 8.76 (s, 1H), 8.67 (s, 1H), 8.52 (s, 1H), 8.18-8.15 (m, 2H), 7.84 (d, J=9.2 Hz, 1H), 7.74 (d, J=9.2 Hz, 1H), 7.20 (t, J=8.4 Hz, 2H), 4.35-4.26 (m, 1H), 4.08-4.03 (m, 3H), 3.48 (t, J=7.2 Hz, 2H), 2.81-2.76 (m, 2H), 2.66-2.59 (m, 2H), 1.44 (t, J=7.2 Hz, 3H), 1.38 (t, J=7.6 Hz, 3H).

Measured value of MS (ESI$^+$) [(M+H)$^+$]: 589.

Example 20: N-(5-(3-((5-cyano-4-(4-fluorophenyl) thiazol-2-yl)(ethyl)amino)-2-ethylimidazo[1,2-a] pyridin-6-yl)pyrimidin-2-yl)-N-methylmethanesulfonamide (compound 20)

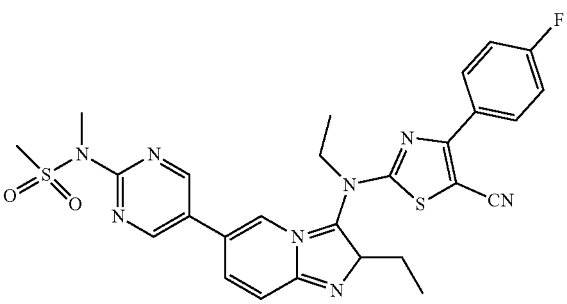

Step 20a: Preparation of N-(5-bromopyrimidin-2-yl)-N-methylmethanesulfonamide

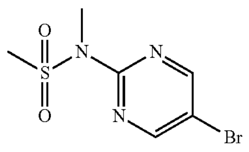

Specific method of Step 20a: N-(5-bromopyrimidin-2-yl)-N-methylmethanesulfonamide (114 mg) was prepared from N-methylmethanesulfonamide (77 mg, 0.707 mmol) and 2,5-dibromopyrimidine (200 mg, 0.848 mmol) according to the method of step 17f in Example 17 under nitrogen atmosphere.

Step 20b: Preparation of N-(5-(3-((5-cyano-4-(4-fluorophenyl)thiazol-2-yl)(ethyl)amino)-2-ethylimidazo[1,2-a]pyridin-6-yl)pyrimidin-2-yl)-N-methylmethanesulfonamide

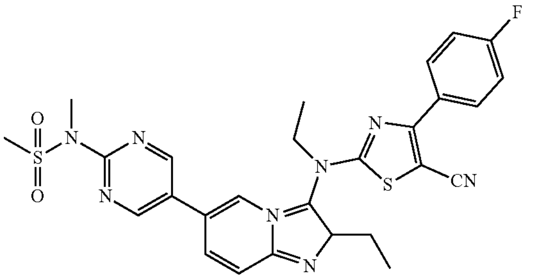

Specific method of Step 20b: N-(5-(3-((5-cyano-4-(4-fluorophenyl)thiazol-2-yl)(ethyl)amino)-2-ethylimidazo[1,2-a]pyridin-6-yl)pyrimidin-2-yl)-N-methylmethanesulfonamide (45 mg) as a brown solid was prepared from N-(5-bromopyrimidin-2-yl)-N-methylmethanesulfonamide (70 mg, 0.263 mmol) and (3-((5-cyano-4-(4-fluorophenyl)thiazol-2-yl)(ethyl)amino)-2-ethylimidazo[1,2-a]pyridin-6-yl)

boronic acid (172 mg, 0.395 mmol) according to the method of step 17 h in Example 17 under nitrogen atmosphere.

$^1$H NMR (400 MHz, $CDCl_3$): δ 8.77 (s, 2H), 8.16 (dd, J=8.8, 5.6 Hz, 2H), 7.92 (br. s, 1H), 7.80 (d, J=9.2 Hz, 1H), 7.48 (dd, J=9.2, 1.2 Hz, 1H), 7.19 (t, J=8.8 Hz, 2H), 4.26-4.21 (m, 1H), 4.10-4.05 (m, 1H), 3.60 (s, 3H), 3.53 (s, 3H), 2.81 (q, J=7.6 Hz, 2H), 1.44 (t, J=7.6 Hz, 3H), 1.38 (t, J=7.2 Hz, 3H).

Measured value of MS ($ESI^+$) $[(M+H)^+]$: 577.

Example 21: 2-((5-(2-(1,1-dioxido-1,2-thiazinan-2-yl)pyrimidin-5-yl)-2-ethyl-2H-pyrazolo[4,3-b]pyridin-3-yl)(ethyl)amino)-4-(4-fluorophenyl)thiazole-5-carbonitrile (compound 21)

21

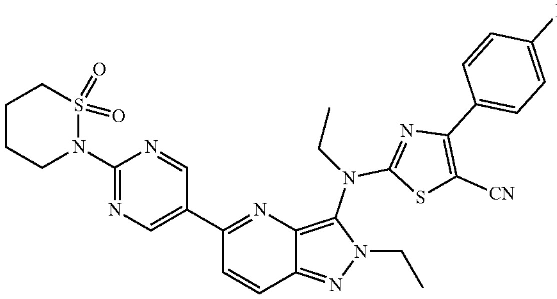

Step 21a: Preparation of 2-(5-bromopyrimidin-2-yl)-1,2-thiazinane 1,1-dioxide

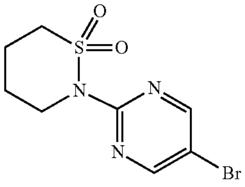 [SMILES: O=S1(=O)CCCCN1c1ncc(Br)cn1]

Specific method of Step 21a: 2-(5-bromopyrimidin-2-yl)-1,2-thiazinane 1,1-dioxide (500 mg) as a brown-like solid was prepared from 1,2-thiazinane 1,1-dioxide (300 mg, 2.22 mmol) and 2,5-dibromopyrimidine (792 mg, 3.33 mmol) according to the method of step 17f in Example 17 at room temperature and under nitrogen atmosphere.

Step 21b: Preparation of (2-(1,1-dioxido-1,2-thiazinan-2-yl)pyrimidin-5-yl)boronic acid

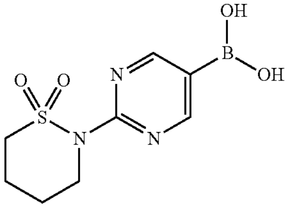 [SMILES: O=S1(=O)CCCCN1c1ncc(B(O)O)cn1]

Specific method of Step 21b: (2-(1,1-dioxido-1,2-thiazinan-2-yl)pyrimidin-5-yl) boronic acid (176 mg) was prepared from 2-(5-bromopyrimidin-2-yl)-1,2-thiazinane 1,1-dioxide (200 mg, 0.68 mmol) and bis(pinacolato)diboron (191 mg, 0.75 mmol) according to the method of step 17g in Example 17 under nitrogen atmosphere.

Step 21c: Preparation of 2-((5-(2-(1,1-dioxido-1,2-thiazinan-2-yl)pyrimidin-5-yl)-2-ethyl-2H-pyrazolo[4,3-b]pyridin-3-yl)(ethyl)amino)-4-(4-fluorophenyl)thiazole-5-carbonitrile

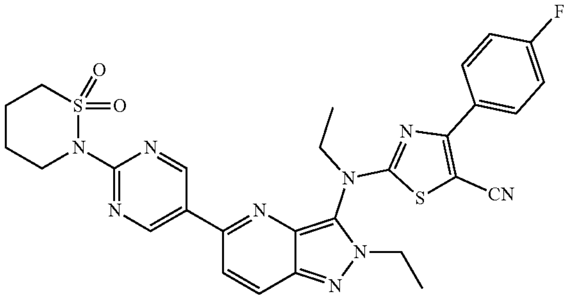 [SMILES: CCN(c1nc(-c2ccc(F)cc2)c(C#N)s1)c1c2nc(-c3cnc(N4CCCCS4(=O)=O)nc3)ccc2nn1CC]

Specific method of Step 21c: 2-((5-(2-(1,1-dioxido-1,2-thiazinan-2-yl)pyrimidin-5-yl)-2-ethyl-2H-pyrazolo[4,3-b]pyridin-3-yl)(ethyl)amino)-4-(4-fluorophenyl)thiazole-5-carbonitrile (60 mg) as a white-like solid was prepared from (2-(1,1-dioxido-1,2-thiazinan-2-yl)pyrimidin-5-yl)boronic acid (175 mg, 0.68 mmol) and 2-((5-bromo-2-ethyl-2H-pyrazolo[4,3-b]pyridin-3-yl)(ethyl)amino)-4-(4-fluorophenyl)thiazole-5-carbonitrile (320 mg, 0.68 mmol) according to the method of step 17 h in Example 17 under nitrogen atmosphere.

$^1$H NMR (400 MHz, CDCl3): δ 9.30 (s, 2H), 8.22 (d, J=9.2 Hz, 1H), 8.12 (dd, J=8.4, 5.2 Hz, 2H), 7.72 (d, J=9.2 Hz, 1H), 7.19-7.15 (m, 2H), 4.63-4.49 (m, 1H), 4.44 (q, J=7.2 Hz, 2H), 4.38-4.32 (m, 2H), 3.93-3.89 (m, 1H), 3.39-3.30 (m, 2H), 2.38-2.30 (m, 2H), 1.89-1.80 (m, 2H), 1.68 (t, J=7.2 Hz, 3H), 1.47 (t, J=7.2 Hz, 3H).

Measured value of MS ($ESI^+$) $[(M+H)^+]$: 604.

Example 22: N-(5-(3-((5-cyano-4-(4-fluorophenyl)thiazol-2-yl)(ethyl)amino)-2-ethylimidazo[1,2-a]pyridin-6-yl)pyrimidin-2-yl)-2-hydroxyethane-1-sulfonamide (compound 22)

22

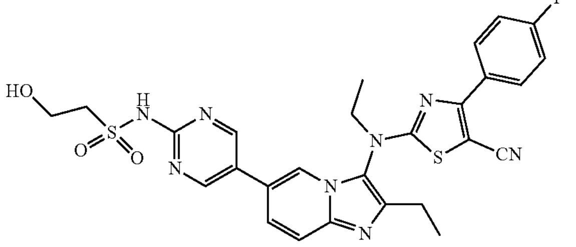

Step 22a: Preparation of 2-(benzyloxy)ethane-1-sulfonic acid

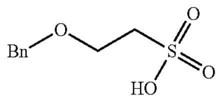 [SMILES: O=S(=O)(O)CCOCc1ccccc1]

Specific method of Step 22a: ((2-bromoethoxy)methyl) benzene (5 g, 23.36 mmol) was added to an aqueous sodium sulfite (3.62 g, 28.67 mmol) solution (170 mL) at room temperature. The mixture was stirred at 100° C. for 6 h, then concentrated to afford a white solid. The white solid was added to methanol (170 mL), and the mixture was heated to 50° C. with stirring for 20 min, filtered, and concentrated to afford 2-(benzyloxy)ethane-1-sulfonic acid (6.8 g) as a white solid.

Step 22b: Preparation of 2-(benzyloxy)ethane-1-sulfonyl chloride

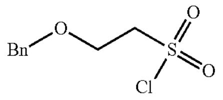 [SMILES: O=S(=O)(Cl)CCOCc1ccccc1]

Specific method of Step 22b: DMF (163 mg, 2.3 mmol) and thionyl chloride (5.1 mL, 90.81 mmol) were added to a solution of 2-(benzyloxy)ethane-1-sulfonic acid (5.0 g, 23.14 mmol) in tetrahydrofuran (20 mL) at room temperature and under nitrogen atmosphere. The mixture was stirred at 65° C. for 5 h. After filtration, the filtrate was concentrated to afford 2-(benzyloxy)ethane-1-sulfonyl chloride (5.6 g) as a yellow oily matter.

Step 22c: Preparation of 2-(benzyloxy)-N-(5-bromopyrimidin-2-yl)ethane-1-sulfonamide

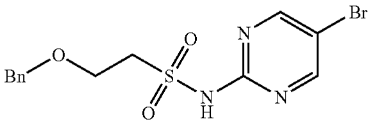 [SMILES: O=S(=O)(CCOCc1ccccc1)Nc1ncc(Br)cn1]

Specific method of Step 22c: 5-bromopyridin-2-amine (6.0 g, 34.69 mmol) and triethylamine (6.4 mL, 46.15 mmol) were added to a solution of 2-(benzyloxy)ethane-1-sulfonyl chloride (5.4 g, 23.08 mmol) in tetrahydrofuran (50 mL) at room temperature, heated to 80° C. and stirred to react for 10 hours. After cooling, the reaction solution was diluted with water (50 mL). The aqueous phase was extracted with ethyl acetate (80 mL×3), and the combined organic phase was washed with saturated saline (50 mL), dried with anhydrous sodium sulfate, filtered, and concentrated under reduced pressure to afford a crude product. The crude product was purified by flash column chromatography to afford 2-(benzyloxy)-N-(5-bromopyrimidin-2-yl)ethane-1-sulfonamide (560 mg) as a white solid.

Step 22d: Preparation of 2-(benzyloxy)-N-(5-(3-((5-cyano-4-(4-fluorophenyl)thiazol-2-yl)(ethyl)amino)-2-ethylimidazo[1,2-a]pyridin-6-yl)pyrimidin-2-yl) ethane-1-sulfonamide

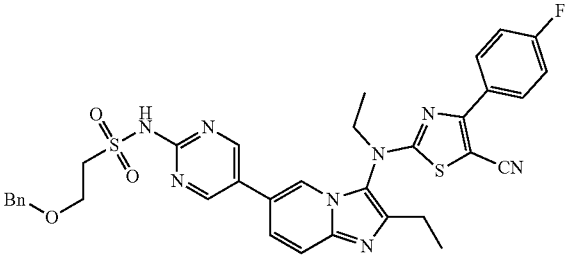 [SMILES: CCc1nc2ccc(-c3cnc(NS(=O)(=O)CCOCc4ccccc4)nc3)cn2c1N(CC)c1nc(-c2ccc(F)cc2)c(C#N)s1]

Specific method of Step 22d: 2-(benzyloxy)-N-(5-(3-((5-cyano-4-(4-fluorophenyl)thiazol-2-yl)(ethyl)amino)-2-ethylimidazo[1,2-a]pyridin-6-yl)pyrimidin-2-yl)ethane-1-sulfonamide (530 mg) as a brown solid was prepared from (3-((5-cyano-4-(4-fluorophenyl)thiazol-2-yl)(ethyl)amino)-2-ethylimidazo[1,2-a]pyridin-6-yl)boronic acid (985 mg, 2.26 mmol) and 2-(benzyloxy)-N-(5-bromopyrimidin-2-yl) ethane-1-sulfonamide (371 mg, 1.51 mmol) according to the method of step 17 h in Example 17 under nitrogen atmosphere.

Step 22e: Preparation of N-(5-(3-((5-cyano-4-(4-fluorophenyl)thiazol-2-yl)(ethyl)amino)-2-ethylimidazo[1,2-a]pyridin-6-yl)pyrimidin-2-yl)-2-hydroxyethane-1-sulfonamide

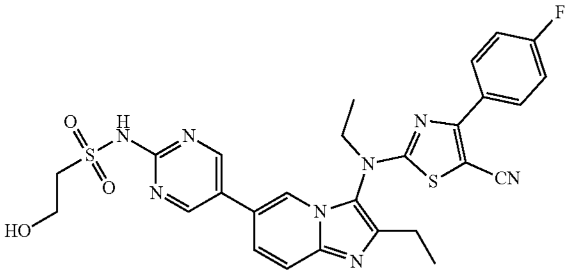 [SMILES: CCc1nc2ccc(-c3cnc(NS(=O)(=O)CCO)nc3)cn2c1N(CC)c1nc(-c2ccc(F)cc2)c(C#N)s1]

Specific method of Step 22e: trifluoroacetic acid (5 mL) was added to 2-(benzyloxy)-N-(5-(3-((5-cyano-4-(4-fluorophenyl)thiazol-2-yl)(ethyl)amino)-2-ethylimidazo[1,2-a] pyridin-6-yl)pyrimidin-2-yl)ethane-1-sulfonamide (530 mg, 0.777 mmol). The mixture was heated to 90° C. in a microwave, and then stirred for 1 hour. Then the mixture was adjusted to pH 8-9 with saturated sodium bicarbonate solution and extracted with ethyl acetate (10 mL×3). The combined organic phase was washed with saturated saline (10 mL), dried with anhydrous sodium sulfate, filtered, and concentrated under reduced pressure to afford N-(5-(3-((5-cyano-4-(4-fluorophenyl)thiazol-2-yl)(ethyl)amino)-2-ethylimidazo[1,2-a]pyridin-6-yl)pyrimidin-2-yl)-2-hydroxyethane-1-sulfonamide (25.6 mg) as a brown solid.

$^1$H NMR (400 MHz, DMSO-$d_6$): δ 8.82 (s, 2H), 8.17-8.13 (m, 2H), 7.95 (br. s, 1H), 7.81 (d, J=9.2 Hz, 1H), 7.47 (d, J=9.2 Hz, 1H), 7.19 (t, J=8.4 Hz, 2H), 4.27-4.18 (m, 1H), 4.12-4.06 (m, 3H), 3.86-3.85 (m, 2H), 2.81 (q, J=7.2 Hz, 2H), 1.44 (t, J=7.2 Hz, 3H), 1.39 (t, J=7.2 Hz, 3H).

Measured value of MS (ESI$^+$) [(M+H)$^+$]: 593.

Example 23: 2-(ethyl(2-ethyl-5-(2-(3-hydroxyazetidin-1-yl)pyrimidin-5-yl)-2H-pyrazolo[4,3-b]pyridin-3-yl)amino)-4-(4-fluorophenyl)thiazole-5-carbonitrile (compound 23)

23

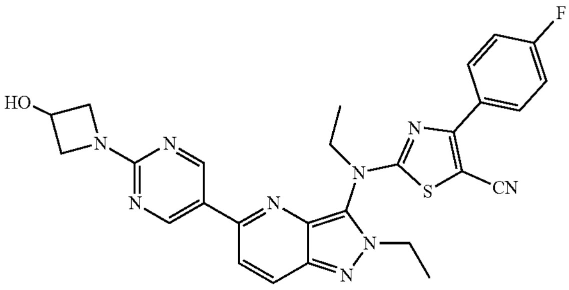

Step 23a: Preparation of 1-(5-bromopyrimidin-2-yl)azetidin-3-ol

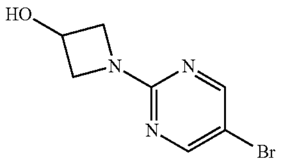 [SMILES: OC1CN(c2ncc(Br)cn2)C1]

Specific method of Step 23a: azetidin-3-ol (149 mg, 2.03 mmol) and potassium carbonate (511 mg, 3.7 mmol) were added to a solution of 2,5-dibromopyrimidine (440 mg, 1.85 mmol) in DMF (5 mL) at room temperature. The mixture was stirred at 80° C. for 1 h, then 50 mL of water was added, after filtration, the filter cake was spin-dried to afford 1-(5-bromopyrimidin-2-yl)azetidin-3-ol (360 mg) as a white-like solid.

Step 23b: Preparation of (2-(3-hydroxyazetidin-1-yl)pyrimidin-5-yl)boronic acid

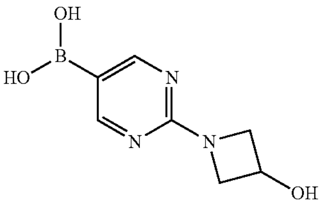 [SMILES: OB(O)c1cnc(N2CC(O)C2)nc1]

Specific method of Step 23b: (2-(3-hydroxyazetidin-1-yl)pyrimidin-5-yl)boronic acid (85 mg) was prepared from 1-(5-bromopyrimidin-2-yl)azetidin-3-ol (100 mg, 0.43 mmol) and bis(pinacolato)diboron (121 mg, 0.48 mmol) according to the method of step 17g in Example 17 under nitrogen atmosphere.

Step 23c: Preparation of 2-(ethyl(2-ethyl-5-(2-(3-hydroxyazetidin-1-yl)pyrimidin-5-yl)-2H-pyrazolo[4,3-b]pyridin-3-yl)amino)-4-(4-fluorophenyl)thiazole-5-carbonitrile

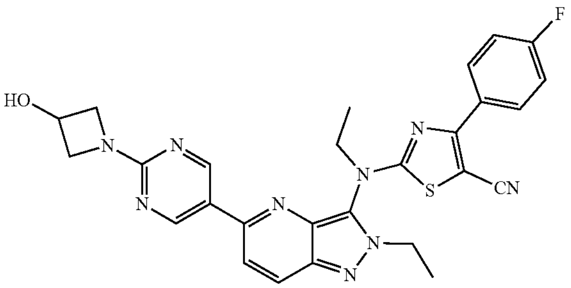 [SMILES: CCN(c1nc(-c2ccc(F)cc2)c(C#N)s1)c1c2nc(-c3cnc(N4CC(O)C4)nc3)ccc2nn1CC]

Specific method of Step 23c: 2-(ethyl(2-ethyl-5-(2-(3-hydroxyazetidin-1-yl)pyrimidin-5-yl)-2H-pyrazolo[4,3-b]pyridin-3-yl)amino)-4-(4-fluorophenyl)thiazole-5-carbonitrile (38 mg) as a white solid was prepared from (2-(3-hydroxyazetidin-1-yl)pyrimidin-5-yl)boronic acid (85 mg, 0.43 mmol) and 2-((5-bromo-2-ethyl-2H-pyrazolo[4,3-b]pyridin-3-yl)(ethyl)amino)-4-(4-fluorophenyl)thiazole-5-carbonitrile (205 mg, 0.43 mmol) according to the method of step 17 h in Example 17 under nitrogen atmosphere.

$^1$H NMR (400 MHz, CDCl3): δ 9.02 (s, 2H), 8.14-8.11 (m, 3H), 7.64 (d, J=9.2 Hz, 1H), 7.20-7.15 (m, 2H), 4.86-4.82 (m, 1H), 4.51-4.47 (m, 2H), 4.42 (q, J=7.2 Hz, 2H), 4.11-4.08 (m, 2H), 3.91-3.87 (m, 1H), 2.28-2.24 (m, 1H), 1.67 (t, J=7.2 Hz, 3H), 1.48 (t, J=7.2 Hz, 3H).

Measured value of MS (ESI$^+$) [(M+H)$^+$]: 542.

Example 24: 2-(ethyl(2-ethyl-5-(2-(3-(hydroxymethyl)azetidin-1-yl)pyrimidin-5-yl)-2H-pyrazolo[4,3-b]pyridin-3-yl)amino)-4-(4-fluorophenyl)thiazole-5-carbonitrile (compound 24)

24

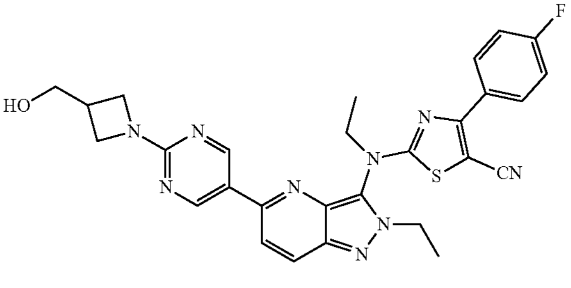

Step 24a: Preparation of (1-(5-bromopyrimidin-2-yl)azetidin-3-yl)methanol

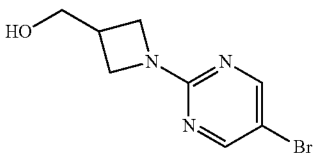 [SMILES: OCC1CN(c2ncc(Br)cn2)C1]

Specific method of Step 24a: azetidin-3-ylmethanol hydrochloride (368 mg, 2.97 mmol) and triethylamine (1.1 mL, 7.75 mmol) were added to a solution of 5-bromo-2-chloropyrimidine (500 mg, 2.58 mmol) in DMF (5 mL) at room temperature. The mixture was stirred at 60° C. for 4 hours. After cooling, the reaction solution was concentrated and diluted with water (60 mL). The aqueous phase was extracted with ethyl acetate (20 mL×3), and the combined organic phase was washed with saturated saline (30 mL), dried with anhydrous sodium sulfate, filtered, and concentrated. The crude product was separated and purified by flash chromatography to afford (1-(5-bromopyrimidin-2-yl)azetidin-3-yl)methanol (618 mg) as a yellow solid.

Step 24b: Preparation of (2-(3-(hydroxymethyl)azetidin-1-yl)pyrimidin-5-yl)boronic acid

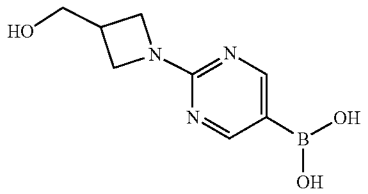 [SMILES: OCC1CN(c2ncc(B(O)O)cn2)C1]

Specific method of Step 24b: (2-(3-(hydroxymethyl)azetidin-1-yl)pyrimidin-5-yl)boronic acid (529 mg) was prepared from (1-(5-bromopyrimidin-2-yl)azetidin-3-yl)methanol (500 mg, 1.70 mmol) and bis(pinacolato)diboron (781 mg, 2.21 mmol) according to the method of step 17g in Example 17 under nitrogen atmosphere.

Step 24c: Preparation of 2-(ethyl(2-ethyl-5-(2-(3-(hydroxymethyl)azetidin-1-yl)pyrimidin-5-yl)-2H-pyrazolo[4,3-b]pyridin-3-yl)amino)-4-(4-fluorophenyl)thiazole-5-carbonitrile

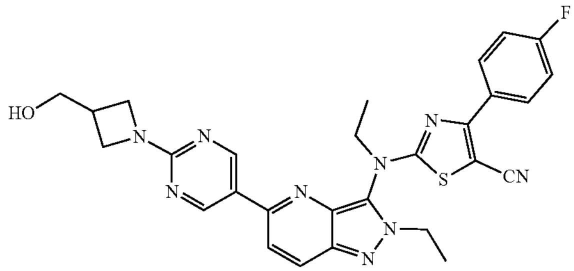 [SMILES: CCN(c1nc(-c2ccc(F)cc2)c(C#N)s1)c1c2nc(-c3cnc(N4CC(CO)C4)nc3)ccc2nn1CC]

Specific method of Step 24c: 2-(ethyl(2-ethyl-5-(2-(3-(hydroxymethyl)azetidin-1-yl)pyrimidin-5-yl)-2H-pyrazolo[4,3-b]pyridin-3-yl)amino)-4-(4-fluorophenyl)thiazole-5-carbonitrile (40 mg) as a white solid was prepared from 2-((5-bromo-2-ethyl-2H-pyrazolo[4,3-b]pyridin-3-yl)(ethyl)amino)-4-(4-fluorophenyl)thiazole-5-carbonitrile (100 mg, 0.21 mmol) and (2-(3-(hydroxymethyl)azetidin-1-yl)pyrimidin-5-yl)boronic acid (133 mg, 0.32 mmol) according to the method of Step 17 h in Example 17.

$^1$H NMR (400 MHz, $CDCl_3$): δ 9.00 (s, 2H), 8.13-8.10 (m, 3H), 7.62 (d, J=8.8 Hz, 1H), 7.16 (m, 2H), 4.65-3.76 (m, 10H), 2.95 (br. s., 1H), 1.41-1.69 (m, 6H).

Measured value of MS ($ESI^+$) [$(M+H)^+$]: 556.

Example 25: 1-(5-(3-((5-cyano-4-(4-fluorophenyl)thiazol-2-yl)(ethyl)amino)-2-ethyl-2H-pyrazolo[4,3-b]pyridin-5-yl)pyrimidin-2-yl)azetidin-3-yl acetate (compound 25)

25

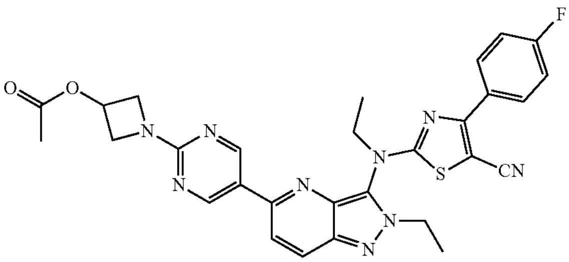

Step 25a: Preparation of 1-(5-(3-((5-cyano-4-(4-fluorophenyl)thiazol-2-yl)(ethyl)amino)-2-ethyl-2H-pyrazolo[4,3-b]pyridin-5-yl)pyrimidin-2-yl)azetidin-3-yl acetate

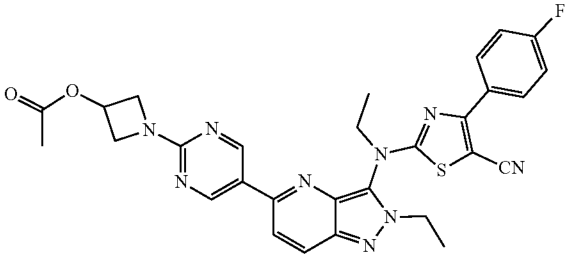 [SMILES: CCN(c1nc(-c2ccc(F)cc2)c(C#N)s1)c1c2nc(-c3cnc(N4CC(OC(C)=O)C4)nc3)ccc2nn1CC]

Specific method of Step 25a: acetyl chloride (58 mg, 0.74 mmol) was added to 2-(ethyl(2-ethyl-5-(2-(3-hydroxyazetidin-1-yl)pyrimidin-5-yl)-2H-pyrazolo[4,3-b]pyridin-3-yl)amino)-4-(4-fluorophenyl)thiazole-5-carbonitrile (200 mg, 0.37 mmol) and triethylamine (112 mg, 1.11 mmol) in dichloromethane (3 mL) at 0° C. under the protection of nitrogen. The mixture was stirred at room temperature for 1 hour, then diluted with water (20 mL) and extracted with dichloromethane (30 mL×2). The combined organic phase was washed with saturated saline, dried with anhydrous sodium sulfate, filtered, and concentrated under reduced pressure to afford a crude product. The crude product was purified by column chromatography to afford 1-(5-(3-((5-cyano-4-(4-fluorophenyl)thiazol-2-yl)(ethyl)amino)-2-ethyl-2H-pyrazolo[4,3-b]pyridin-5-yl)pyrimidin-2-yl)azetidin-3-yl acetate (100 mg) as a white-like solid.

$^1$H NMR (400 MHz, $CDCl_3$): δ 9.02 (s, 2H), 8.18-8.09 (m, 3H), 7.64 (d, J=9.3 Hz, 1H), 7.20-7.14 (m, 2H), 5.38-5.34 (m, 1H), 4.57-4.52 (m, 3H), 4.41 (q, J=7.1 Hz, 2H), 4.19-4.15 (m, 2H), 3.90-3.86 (m, 1H), 2.14 (s, 3H), 1.66 (t, J=7.4 Hz, 3H), 1.47 (t, J=7.1 Hz, 3H).

Measured value of MS ($ESI^+$) [$(M+H)^+$]: 584.

Example 26: 2-(ethyl(2-ethyl-5-(2-(4-hydroxypiperidin-1-yl)pyrimidin-5-yl)-2H-pyrazolo[4,3-b]pyridin-3-yl)amino)-4-(4-fluorophenyl)thiazole-5-carbonitrile (compound 26)

26

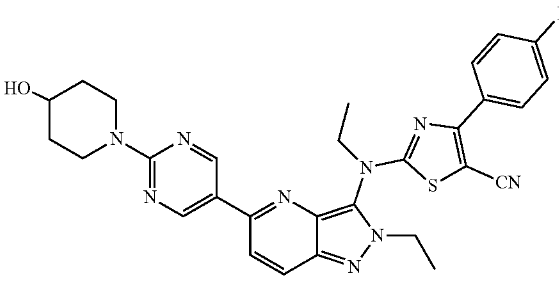

Step 26a: Preparation of 1-(5-bromopyrimidin-2-yl)piperidin-4-ol

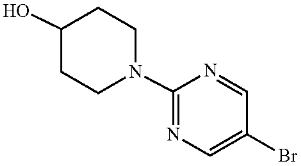 [SMILES: OC1CCN(c2ncc(Br)cn2)CC1]

Specific method of Step 26a: 1-(5-bromopyrimidin-2-yl) piperidin-4-ol (350 mg) as a white-like solid was prepared from 2,5-dibromopyrimidine (440 mg, 1.85 mmol), 4-hydroxypiperidine (206 mg, 2.03 mmol) and potassium carbonate (511 mg, 3.7 mmol) according to the method of step 23a in Example 23.

Step 26b: Preparation of (2-(4-hydroxypiperidin-1-yl)pyrimidin-5-yl)boronic acid

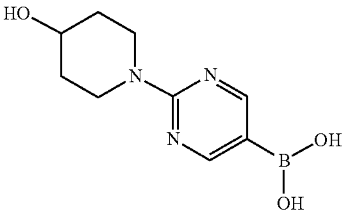 [SMILES: OB(O)c1cnc(N2CCC(O)CC2)nc1]

Specific method of Step 26b: (2-(4-hydroxypiperidin-1-yl)pyrimidin-5-yl)boronic acid (95 mg) was prepared from 1-(5-bromopyrimidin-2-yl)piperidin-4-ol (110 mg, 0.43 mmol) and bis(pinacolato)diboron (130 mg, 0.51 mmol) according to the method of step 23b in Example 23 under nitrogen atmosphere.

Step 26c: Preparation of 2-(ethyl(2-ethyl-5-(2-(4-hydroxypiperidin-1-yl)pyrimidin-5-yl)-2H-pyrazolo[4,3-b]pyridin-3-yl)amino)-4-(4-fluorophenyl)thiazole-5-carbonitrile

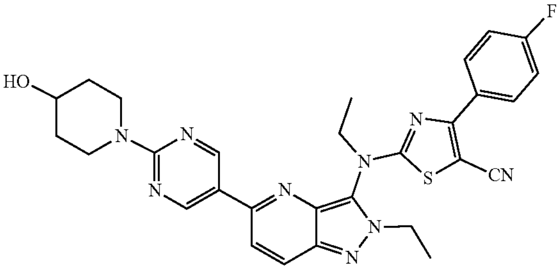 [SMILES: CCN(c1nc(-c2ccc(F)cc2)c(C#N)s1)c1c2nc(-c3cnc(N4CCC(O)CC4)nc3)ccc2nn1CC]

Specific method of Step 26c: 2-(ethyl(2-ethyl-5-(2-(4-hydroxypiperidin-1-yl)pyrimidin-5-yl)-2H-pyrazolo[4,3-b]pyridin-3-yl)amino)-4-(4-fluorophenyl)thiazole-5-carbonitrile (50 mg) as a white-like solid was prepared from (2-(4-hydroxyazetidin-1-yl)pyrimidin-5-yl)boronic acid (95 mg, 0.43 mmol) and 2-((5-bromo-2-ethyl-2H-pyrazolo[4,3-b]pyridin-3-yl)(ethyl)amino)-4-(4-fluorophenyl)thiazole-5-carbonitrile (205 mg, 0.43 mmol) according to the method of step 23c in Example 23 under nitrogen atmosphere.

$^1$H NMR (400 MHz, $CDCl_3$): δ 9.00 (s, 2H), 8.17-8.07 (m, 3H), 7.64 (d, J=9.3 Hz, 1H), 7.19-7.15 (m, 2H), 4.55-4.35 (m, 5H), 4.03-3.85 (m, 2H), 3.47-3.41 (m, 2H), 2.00-1.95 (m, 2H), 1.66 (t, J=7.2 Hz, 3H), 1.59-1.52 (m, 2H), 1.47 (t, J=7.2 Hz, 3H).

Measured value of MS ($ESI^+$) [$(M+H)^+$]: 570.

Example 27: (S)-2-(ethyl(2-ethyl-5-(2-(3-hydroxypyrrolidin-1-yl)pyrimidin-5-yl)-2H-pyrazolo[4,3-b]pyridin-3-yl)amino)-4-(4-fluorophenyl)thiazole-5-carbonitrile (compound 27)

27

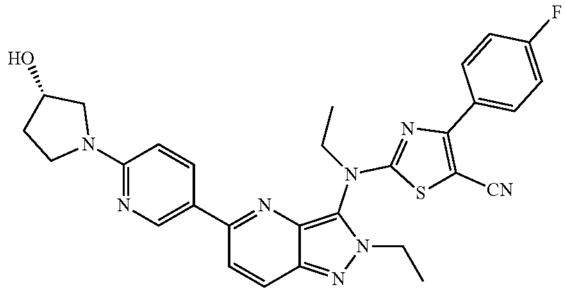

Step 27a: Preparation of (S)-1-(5-bromopyrimidin-2-yl)pyrrolidin-3-ol

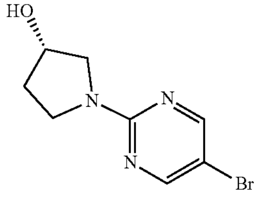 [SMILES: O[C@H]1CCN(c2ncc(Br)cn2)C1]

Specific method of Step 27a: (S)-1-(5-bromopyrimidin-2-yl)pyrrolidin-3-ol (800 mg) as a white solid was prepared by adding (S)-pyrrolidin-3-ol (0.4 g, 4.7 mmol) to a solution of 2,5-dibromopyrimidine (1 g, 4.2 mmol) in DMF (8 mL) according to the method of step 23a in Example 23 at room temperature.

Step 27b: Preparation of (S)-(2-(3-hydroxypyrrolidin-1-yl)pyrimidin-5-yl)boronic acid

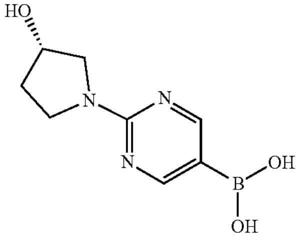 [SMILES: OB(O)c1cnc(N2CC[C@H](O)C2)nc1]

Specific method of Step 27b: (S)-(2-(3-hydroxypyrrolidin-1-yl)pyrimidin-5-yl)boronic acid (400 mg) was prepared from (S)-1-(5-bromopyrimidin-2-yl)pyrrolidin-3-ol (200 mg, 0.82 mmol) and bis(pinacolato)diboron (230 mg, 0.9 mmol) according to the method of step 23b in Example 23 under nitrogen atmosphere.

Step 27c: Preparation of (S)-2-(ethyl(2-ethyl-5-(2-(3-hydroxypyrrolidin-1-yl)pyrimidin-5-yl)-2H-pyrazolo[4,3-b]pyridin-3-yl)amino)-4-(4-fluorophenyl)thiazole-5-carbonitrile

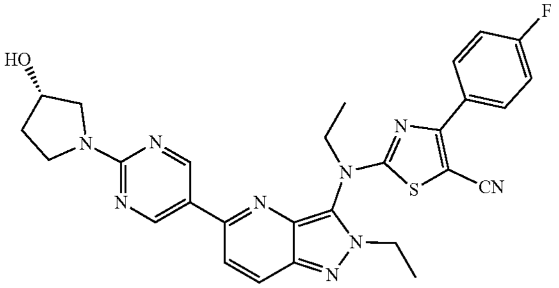 [SMILES: CCN(c1nc(-c2ccc(F)cc2)c(C#N)s1)c1c2nc(-c3cnc(N4CC[C@H](O)C4)nc3)ccc2nn1CC]

Specific method of Step 27c: (S)-2-(ethyl(2-ethyl-5-(2-(3-hydroxypyrrolidin-1-yl)pyrimidin-5-yl)-2H-pyrazolo[4,3-b]pyridin-3-yl)amino)-4-(4-fluorophenyl)thiazole-5-carbonitrile (100 mg) as a white solid was prepared from (S)-(2-(3-hydroxypyrrolidin-1-yl)pyrimidin-5-yl)boronic acid (200 mg, 0.43 mmol) and 2-((5-bromo-2-ethyl-2H-pyrazolo[4,3-b]pyridin-3-yl)(ethyl)amino)-4-(4-fluorophenyl)thiazole-5-carbonitrile (200 mg, 0.43 mmol) according to the method of step 23c in Example 23 under nitrogen atmosphere.

$^1$H NMR (400 MHz, DMSO-$d_6$): δ 9.04 (br. s, 2H), 8.16-8.11 (m, 3H), 7.65 (d, J=8.8 Hz, 1H), 7.19 (t, J=8.8 Hz, 2H), 4.66 (s, 1H), 4.61-4.45 (m, 1H), 4.44-4.39 (m, 2H), 4.01-3.92 (m, 1H), 3.85-3.81 (m, 2H), 3.78-3.73 (m, 2H), 2.24-2.10 (m, 2H), 1.78 (d, J=2.8 Hz, 1H), 1.68 (t, J=7.2 Hz, 3H), 1.49 (t, J=7.2 Hz, 3H).

Measured value of MS (ESI$^+$) [(M+H)$^+$]: 556.

Example 28: (R)-2-(ethyl(2-ethyl-5-(2-(3-hydroxypyrrolidin-1-yl)pyrimidin-5-yl)-2H-pyrazolo[4,3-b]pyridin-3-yl)amino)-4-(4-fluorophenyl)thiazole-5-carbonitrile (compound 28)

28

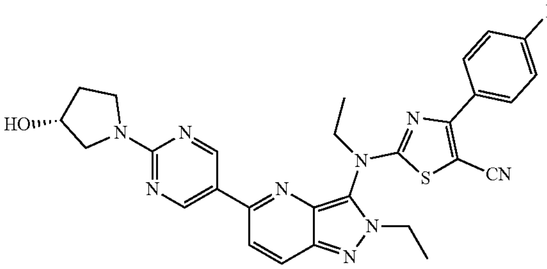

Step 28a: Preparation of (R)-1-(5-bromopyrimidin-2-yl)pyrrolidin-3-ol

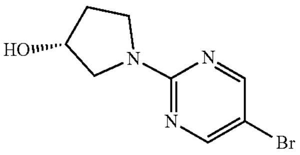 [SMILES: O[C@@H]1CCN(c2ncc(Br)cn2)C1]

Specific method of Step 28a: (R)-1-(5-bromopyrimidin-2-yl)pyrrolidin-3-ol (472 mg) as a white solid was prepared from 5-bromo-2-chloropyrimidine (500 mg, 2.10 mmol) and (R)-pyrrolidin-3-ol (210 mg, 2.42 mmol) according to the method of step 23a in Example 23 at room temperature.

Step 28b: Preparation of (R)-(2-(3-hydroxypyrrolidin-1-yl)pyrimidin-5-yl)boronic acid

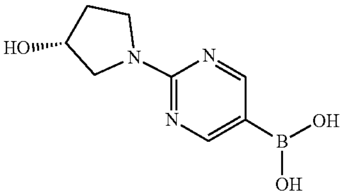 [SMILES: OB(O)c1cnc(N2CC[C@@H](O)C2)nc1]

Specific method of Step 28b: (R)-(2-(3-hydroxypyrrolidin-1-yl)pyrimidin-5-yl)boronic acid (171 mg) was prepared from (R)-1-(5-bromopyrimidin-2-yl)pyrrolidin-3-ol (200 mg, 0.82 mmol) and bis(pinacolato)diboron (312 mg, 1.23 mmol) according to the method of step 23b in Example 23.

Step 28c: Preparation of (R)-2-(ethyl(2-ethyl-5-(2-(3-hydroxypyrrolidin-1-yl)pyrimidin-5-yl)-2H-pyrazolo[4,3-b]pyridin-3-yl)amino)-4-(4-fluorophenyl) thiazole-5-carbonitrile

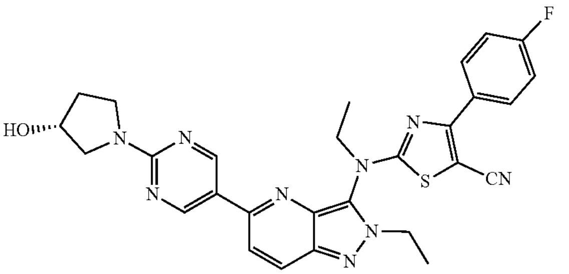 [SMILES: CCN(c1nc(-c2ccc(F)cc2)c(C#N)s1)c1c2nc(-c3cnc(N4CC[C@@H](O)C4)nc3)ccc2nn1CC]

Specific method of Step 28c: (R)-2-(ethyl(2-ethyl-5-(2-(3-hydroxypyrrolidin-1-yl)pyrimidin-5-yl)-2H-pyrazolo[4,3-b]pyridin-3-yl)amino)-4-(4-fluorophenyl)thiazole-5-carbonitrile (56 mg) as a white solid was prepared from 2-((5-bromo-2-ethyl-2H-pyrazolo[4,3-b]pyridin-3-yl)(ethyl)amino)-4-(4-fluorophenyl)thiazole-5-carbonitrile (100 mg, 0.21 mmol) and (R)-(2-(3-hydroxypyrrolidin-1-yl)pyrimidin-5-yl)boronic acid (67 mg, 0.32 mmol) according to the method of step 23c in Example 23.

$^1$H NMR (400 MHz, $CDCl_3$): δ 9.03 (s, 2H), 8.25-7.98 (m, 3H), 7.64 (d, J=9.0 Hz, 1H), 7.17 (t, J=8.4 Hz, 2H), 4.65 (br. s., 1H), 4.53 (br. s., 1H), 4.40 (d, J=7.0 Hz, 2H), 3.90-3.64 (m, 5H), 2.19-2.05 (m, 2H), 1.67 (t, J=7.1 Hz, 3H), 1.47 (t, J=7.1 Hz, 3H).

Measured value of MS ($ESI^+$) [$(M+H)^+$]: 556.

Example 29: 2-(ethyl(2-ethyl-5-(2-morpholinopyrimidin-5-yl)-2H-pyrazolo[4,3-b]pyridin-3-yl)amino)-4-(4-fluorophenyl)thiazole-5-carbonitrile (compound 29)

29

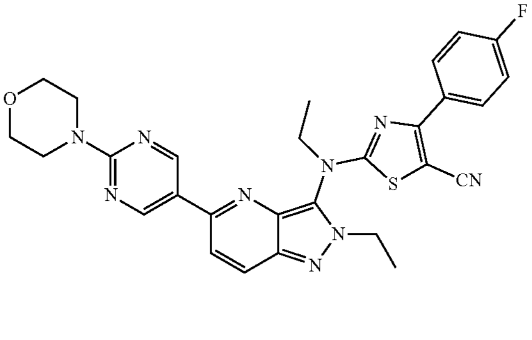

Step 29a: Preparation of 4-(5-bromopyrimidin-2-yl)morpholine

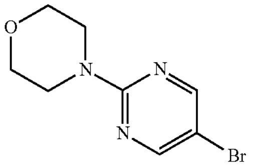 [SMILES: Brc1cnc(N2CCOCC2)nc1]

Specific method of Step 29a: 4-(5-bromopyrimidin-2-yl) morpholine (400 mg) as a white solid was prepared from 5-bromo-2-chloropyrimidine (500 mg, 2.10 mmol) and morpholine (200 mg, 2.3 mmol) according to the method of step 23a in Example 23 at room temperature.

Step 29b: Preparation of (2-morpholinopyrimidin-5-yl)boronic acid

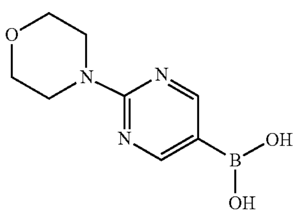 [SMILES: OB(O)c1cnc(N2CCOCC2)nc1]

Specific method of Step 29b: (2-morpholinopyrimidin-5-yl)boronic acid (180 mg) was prepared from 4-(5-bromopyrimidin-2-yl)morpholine (200 mg, 0.82 mmol) and bis(pinacolato)diboron (312 mg, 1.23 mmol) according to the method of step 23b in Example 23.

Step 29c: Preparation 2-(ethyl(2-ethyl-5-(2-morpholinopyrimidin-5-yl)-2H-pyrazolo[4,3-b]pyridin-3-yl)amino)-4-(4-fluorophenyl)thiazole-5-carbonitrile

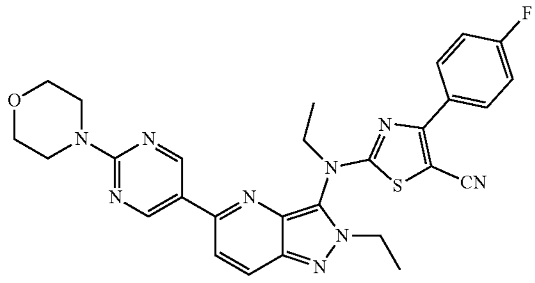 [SMILES: CCN(c1nc(-c2ccc(F)cc2)c(C#N)s1)c1c2nc(-c3cnc(N4CCOCC4)nc3)ccc2nn1CC]

Specific method of Step 29c: 2-(ethyl(2-ethyl-5-(2-morpholinopyrimidin-5-yl)-2H-pyrazolo[4,3-b]pyridin-3-yl) amino)-4-(4-fluorophenyl)thiazole-5-carbonitrile (60 mg) as a white solid was prepared from 2-((5-bromo-2-ethyl-2H-pyrazolo[4,3-b]pyridin-3-yl)(ethyl)amino)-4-(4-fluorophenyl)thiazole-5-carbonitrile (100 mg, 0.21 mmol) and (2-morpholinopyrimidin-5-yl)boronic acid (84 mg, 0.40 mmol) according to the method of step 23c in Example 23.

$^1$H NMR (400 MHz, $CDCl_3$): δ 9.03 (s, 2H), 8.15-8.11 (m, 3H), 7.64 (d, J=9.2 Hz, 1H), 7.17 (t, J=8.4 Hz, 2H), 4.40

(q, J=7.2 Hz, 2H), 3.91-3.88 (m, 5H), 3.79-3.77 (m, 5H), 1.66 (t, J=7.2 Hz, 3H), 1.47 (t, J=7.2 Hz, 3H).

Measured value of MS ($ESI^+$) [$(M+H)^+$]: 556.

Biological experiment data were described in detail below to further illustrate the technical solution of the present disclosure.

Experimental Example 1: ATX Enzyme Activity Inhibition Assay

Experimental Steps:

The tested compounds were dissolved with dimethyl sulfoxide (DMSO) to prepare 20 mM of stock solutions, the stock solutions were subjected to 4-fold gradient dilutions with DMSO, with the initial concentration of 20 μM and a total of 8 concentration gradients. 20 nL of diluted compound was transferred to a 384-well plate using Echo 550 and 5 L of ATX enzyme solution formulated with 4×Tris-HCl reaction buffer to the well, then the 384-well plate was centrifuged at 1000 rpm for 1 min and pre-incubated for 1 min and pre-incubated at room temperature for 15 min. Subsequently, 5 L of 16:0-LPC formulated with the above 4×reaction buffer and 10 L of assay solution containing 2×Amplex UltraRed reagent, choline oxidase and horseradish peroxidase (HRP) formulated with the same reaction buffer were added to each well, then the 384-well plate was centrifugated at 1000 rpm for 1 min. The fluorescence signals were read at an excitation wavelength of 530 nm and an emission wavelength of 590 nm by Synergy 2 microplate reader. The inhibition rate of the compound against enzyme reaction was calculated according to the fluorescence intensity ratio, and $IC_{50}$ of the compound was analysed and calculated by GraphPad Prism 5 software.

Assay Results:

The inhibitory activities of the compounds involved in Example 1 to Example 29 of the present disclosure and GLPG-1690 against ATX were measured according to the above method. The results are summarized in Table 3.

TABLE 3

Activity data of compounds in Examples

| Examples | $IC_{50}$ (μM) | Examples | $IC_{50}$ (μM) |
|---|---|---|---|
| 1 | 0.030 | 2 | 0.029 |
| 3 | 0.0052 | 4 | 0.021 |
| 5 | 0.048 | 6 | 0.029 |
| 7 | 0.025 | 8 | 0.0044 |
| 9 | 0.028 | 10 | 0.018 |
| 11 | 0.025 | 12 | 0.019 |
| 13 | 0.013 | 14 | 0.042 |
| 15 | 0.040 | 16 | 0.039 |
| 17 | 0.0074 | 18 | 0.015 |
| 19 | 0.017 | 20 | 0.045 |
| 21 | 0.011 | 23 | 0.011 |
| 24 | 0.011 | 25 | 0.012 |
| 26 | 0.0055 | 27 | 0.0046 |
| 28 | 0.0038 | 29 | 0.023 |
| GLPG1690 | 0.112 | | |

Conclusions:

As can be seen from Table 3, the inhibitory activity of each compound in Example of the present disclosure against ATX enzyme is better than that of GLPG1690.

Experimental Example 2: Rat Pharmacokinetic Study

SD rat pharmacokinetic study was performed on several compounds in Examples of the present disclosure through a single intravenous injection (IV, at a dose of 2 mg/kg) and a single oral administration (PO, at a dose of 10 mg/kg), and blood samples were taken before administration and 5 min, 15 min, 30 min, 1 h, 2 h, 4 h, 8 h, 12 h and 24 h after administration, respectively, to determine the plasma concentration of the compound for assay. The pharmacokinetic data of control compound and the compounds in Examples 17, 26, 28 and 29 of the present disclosure in rat plasma are shown in Tables 4-8.

The results show that in vivo exposures of rats to the compounds in Examples 17, 26, 28 and 29 after a single intravenous injection and a single oral administration are all higher than those to GLPG1690, and the clearance rates of the former are lower than those of the latter.

TABLE 4

In vivo PK parameters of control compound GLPG1690 in rat

| | IV (2 mg/kg) | PO (10 mg/kg) |
|---|---|---|
| $T_{max}$ (h) | / | 1.0 |
| $C_{max}$ (ng/mL) | 8337 | 512 |
| $AUC_{last}$ (ng/mL * h) | 4460 | 2675 |
| $AUC_{INF}$ (ng/mL * h) | 4465 | 2699 |
| $t_{1/2}$ (h) | 1.5 | 4.0 |
| Cl_F_pred (L/h/kg) | 0.45 | 3.93 |
| F | 12% | |

TABLE 5

In vivo PK parameters of compound in Example 17 in rat

| | IV (2 mg/kg) | PO (10 mg/kg) |
|---|---|---|
| $T_{max}$ (h) | / | 4.0 |
| $C_{max}$ (ng/mL) | 2541 | 1028 |
| $AUC_{last}$ (ng/mL * h) | 4683 | 9027 |
| $AUC_{INF}$ (ng/mL * h) | 4725 | 9178 |
| $t_{1/2}$ (h) | 4.0 | 3.7 |
| Cl_F_pred (L/h/kg) | 0.43 | 1.09 |
| F | 38.5% | |

TABLE 6

In vivo PK parameters of compound in Example 26 in rat

| | IV (2 mg/kg) | PO (10 mg/kg) |
|---|---|---|
| $T_{max}$ (h) | / | 4.0 |
| $C_{max}$ (ng/mL) | 3070 | 663 |
| $AUC_{last}$ (ng/mL * h) | 7504 | 6227 |
| $AUC_{INF}$ (ng/mL * h) | 8169 | 6724 |
| $t_{1/2}$ (h) | 9.3 | 5.8 |
| Cl_F_pred (L/h/kg) | 0.25 | 1.5 |
| F | 16.6% | |

TABLE 7

In vivo PK parameters of compound in Example 28 in rat

| | IV (2 mg/kg) | PO (10 mg/kg) |
|---|---|---|
| $T_{max}$ (h) | / | 4.0 |
| $C_{max}$ (ng/mL) | 4377 | 1718 |
| $AUC_{last}$ (ng/mL * h) | 13935 | 18035 |
| $AUC_{INF}$ (ng/mL * h) | 14136 | 18583 |
| $t_{1/2}$ (h) | 4.1 | 4.2 |
| Cl_F_pred (L/h/kg) | 0.14 | 0.6 |
| F | 25.9% | |

TABLE 8

| In vivo PK parameters of compound in Example 29 in rat | | |
|---|---|---|
| | IV (2 mg/kg) | PO (10 mg/kg) |
| $T_{max}$ (h) | / | 3.3 |
| $C_{max}$ (ng/mL) | 3476 | 847 |
| $AUC_{last}$ (ng/mL * h) | 6835 | 7784 |
| $AUC_{INF}$ (ng/mL * h) | 7220 | 9148 |
| $t_{1/2}$ (h) | 8.2 | 9.2 |
| Cl_F_pred (L/h/kg) | 0.29 | 1.1 |
| F | 11.2% | |

Experimental Example 3: In Vitro Micronucleus Assay with Chinese Hamster Ovary Cells The ability of the compound in Example 26 and GLPG1690 to induce micronucleus formation in Chinese hamster ovary cells (CHO-WBL) with or without addition of an exogenous metabolic activation system (β-naphthoflavone- and phenobarbital-induced rat liver S9) was investigated to evaluate their potential for chromosome breakage/aneuploidy induction.

In the major micronucleus assay, CHO-WBL cells were exposed to at least 3 concentrations of the test object, while vehicle control group and positive control group were setup, with 2 replicated wells for each dose group. In inactivated test system, the administration lasted for 3 and 24 hours, and in S9 activated test system, the exposure to the test object lasted for 3 hours.

The upper limit of concentration of the test object for assay depended on its solubility in the medium, but generally did not exceed the maximum concentration of 1 mM or 0.5 mg/mL, whichever is lower. When choosing the highest dose for micronucleus frequency assay, the cytotoxicity of dose group of the test object should not substantially exceed 50% of that of the corresponding vehicle control group. If the maximum concentration is not limited to cytotoxicity, in order to reach the upper limit of solubility in the medium, several doses exhibiting visible precipitates can be tested, and a small amount of recognizable precipitates can be observed in the medium of the highest dose group selected for micronucleus assay.

On the premise that the test is valid, the test results are evaluated according to the following criteria:

1. Positive

If the test object simultaneously meets the following criteria, it can be considered as positive:

A significant increase in micronucleus frequency is observed in one or more concentration groups.

The micronucleus frequency observed in one or more concentration groups is beyond the range of historic data of negative control in laboratory.

The increase of micronucleus frequency exhibits a dose-effect relationship.

2. Negative

If none of the above three points is met, the test object can be considered as negative.

| series of 3-hour administration with metabolic activation | | | | | series of 3-hour administration without metabolic activation | | | | |
|---|---|---|---|---|---|---|---|---|---|
| | % binuclear cells containing micronucleus | | | | | % binuclear cells containing micronucleus | | | |
| Dose (μg/ml) | 0 | | | | Dose (μg/ml) | 0 | | | |
| DMSO (negative control) | 1.85 | | | | DMSO (negative control) | 1.75 | | | |
| dose (μg/ml) | 5 | | | | dose (μg/ml) | 0.3 | | | |
| Cyclophosphamide monohydrate (positive control, % binuclear cells containing micronucleus | 20.8 | | | | Mitomycin C (positive control, % binuclear cells containing micronucleus) | 11.85 | | | |
| Dose of Example 26 (μg/ml) | 3 | 6 | 12 | 20 | Dose of Example 26 (μg/ml) | 3 | 6 | 12 | 25 |
| Result of Example 26 (% binuclear cells containing micronucleus) | 1.65 | 1.65 | 1.75 | 1.60 | Result of Example 26 (% binuclear cells containing micronucleus) | 1.85 | 1.80 | 1.70 | 1.50 |
| Dose of GLPG1690 (μg/ml) | 2 | 5 | 10 | 30 | Dose of GLPG1690 (μg/ml) | 2 | 5 | 10 | 30 |
| Result of GLPG1690 (% binuclear cells containing micronucleus) | 1.55 | 1.65 | 1.70 | 1.85 | Result of GLPG1690 (% binuclear cells containing micronucleus) | 1.90 | 1.85 | 1.65 | 1.85 |

| series of 24-hour administration without metabolic activation | | | | | series of 24-hour administration without metabolic activation | | | | | |
|---|---|---|---|---|---|---|---|---|---|---|
| | % binuclear cells containing micronucleus | | | | | % binuclear cells containing micronucleus | | | | |
| dose (μg/ml) | 0 | | | | dose (μg/ml) | 0 | | | | |
| DMSO (negative control) | 1.85 | | | | DMSO (negative control) | 1.85 | | | | |
| Dose (μg/ml) | 0.1 | | | | Dose (μg/ml) | 0.1 | | | | |
| Mitomycin C (positive control, % binuclear cells containing micronucleus) | 19.5 | | | | Mitomycin C (positive control, % binuclear cells containing micronucleus) | 22.8 | | | | |
| Dose of Example 26 (μg/ml) | 1 | 3 | 6 | 9 | Dose of GLPG1690 (μg/ml) | 2 | 4 | 6 | 7 | 8 |
| Result of Example 26 (% binuclear cells containing micronucleus) | 1.90 | 1.65 | 1.85 | 1.80 | Result of GLPG1690 (% binuclear cells containing micronucleus) | 1.95 | 1.65 | 1.60 | 4.85 | 14.4 |

Compared with the vehicle control groups in parallel, there was no significant increase in the frequency of binuclear cells containing micronucleus at the test concentrations in every administration series of the compound in Example 26. Besides, there is no dose-effect relationship for the increase of micronucleus frequency. In the positive control (cyclophosphamide monohydrate and mitomycin C) groups, the frequency of micronucleus-containing binuclear cell increased significantly, which proved the effectiveness of the experimental system. The potential of the compound in Example 26 to induce micronucleus formation in CHO-WBL cells is negative.

Compared with the vehicle control groups in parallel, the frequency of micronucleus-containing binuclear cells is significantly increased at the test concentrations of 7 and 8 μg/mL of GLPG1690, also known as AKEX0070, in the series of 24-hour administration without metabolic activation, and there is a dose-effect relationship for the increase of micronucleus frequency. In the positive control (cyclophosphamide monohydrate and mitomycin C) groups, the frequency of micronucleus-containing binuclear cell increased significantly, which proved the effectiveness of the experimental system. The potential of GLPG1690 to induce micronucleus formation in CHO-WBL cells is positive.

Based on the above results, GLPG1690 is genotoxic, and the compound in Example 26 has higher efficacy than GLPG1690.

Experimental Example 4: CYP Enzyme Inhibition Assay

CYP450 enzyme inhibition assay at a single concentration: a system was used to directly incubate 320 μL of human liver microsomes (at a final concentration of 0.05 mg/mL, for 3A4 subtype), and the system contained NADPH (at a final concentration of 1.3 mM), 10 M of compound, a positive inhibitor (0.1 μM of ketoconazole), a negative control (BPS containing 0.1% DMSO) and a mixed probe substrate (5 μM of midazolam), and the reaction was terminated after incubation for 5 min. The relative activity of enzyme was calculated by measuring the relative yield of metabolite.

According to the above method, the CYP450 enzyme inhibition data at the single concentration of 10 μM for control compound GLPG1690 and the compounds in Examples 17, 23, 26 and 27 of the present disclosure are shown in Table below. The results show that the inhibitory activities of Examples 17, 23, 26 and 27 against 3A4 subtype are lower than that of GLPG1690, thus indicating a lower risk of drug-drug interaction clinical practice.

| Compound | 3A4 subtype |
|---|---|
| GLPG1690 | 73.5 |
| Example 17 | 18.6 |
| Example 23 | 39.0 |
| Example 26 | 31.1 |
| Example 27 | 47.7 |

Experimental Example 5: hERG Inhibition Assay

Rapid activation of human delayed rectifier potassium current ($I_{Kr}$) is mainly mediated by hERG ion channel and participates in repolarization of human cardiomyocytes. Blocking this current with drugs will lead to QT interval prolongation syndrome in clinical practice, which will easily induce acute arrhythmia and even sudden death. In this study, the effects of compounds in several Examples on hERG potassium current were tested on stable cell lines transfected with the hERG potassium channel by using a manual patch clamp, in order to determine whether the test object has inhibitory effect on the hERG ion channel.

Experimental method: a whole-cell patch clamp technique was used to record hERG current. The cell suspension was added to a small petri dish and placed on an inverted microscope stage. After adherence, the cells were perfused with extracellular fluid at a recommended flow rate of 1-2 mL/min. The glass microelectrode was drawn by a microelectrode drawing instrument in two steps, and the resistance thereof after filling the electrode interior liquid was 2-5 MΩ. After the whole-cell recording mode was set up, the clamping potential was maintained at −80 mV. The depolarization voltage was applied to +60 mV for 850 ms, and then repolarized to −50 mV for 1275 ms to induce hERG tail current. Such a set of pulse programming was repeated every 15 seconds throughout the experiment. After the current was stable, the drug was administered by extracellular continuous perfusion from low concentration to high concentration. Starting from low concentration, perfusion continued until the drug effect was stable, then perfusion at the next concentration was performed. In this experiment, the blocking effect on hERG tail current was tested for the test objects at different concentrations and the positive control (N≥2). Then, stimulus generation and signal acquisition were carried out by PatchMaster software; and a signal was amplified with a patch clamp amplifier. FitMaster, EXCEL, Graphpad Prism, SPSS 21.0, etc. were used for further data analysis and curve fitting. In data processing, when determining the blocking effect on hERG, the peak and baseline of tail current were calibrated. The inhibition rate (IR) of tail current was used to express the effect of the compounds at different concentrations.

IR=100%×(peak of tail current before administration−peak of tail current after administration)/peak of tail current before administration.

$IC_{50}$ was obtained by fitting the Hill equation (if applicable), if the maximum inhibition rate of the test object at all concentrations was less than 50%, then $IC_{50}$ was not calculated.

$$y = \left[\frac{\max - \min}{1 + \left(\frac{[\text{drug}]}{IC_{50}}\right)^{n_H}}\right] + \min,$$

wherein y: $I/I_{control}$; max: 100%; min: 0%; [drug]: concentration of test object; $n_H$: Hill slope; $IC_{50}$: half maximal inhibitory concentration (MIC) of test object According to the above method, the $IC_{50}$ data of the inhibitory effect on hERG current of control compound and Examples 17, 26, 27 and 29 of the present disclosure are shown in the table below. The results showed that the inhibitory effects on hERG current of control compound GLPG1690 and Examples 17, 26, 27 and 29 are all more than 30 μM, thus indicating no inhibitory effect.

| Compound | hERG $IC_{50}$ [μM] |
|---|---|
| GLPG1690 | >30 |
| Example 17 | >30 |
| Example 26 | >30 |
| Example 27 | >30 |
| Example 29 | >30 |

Experimental Example 6: 3A4 Subtype of CYP450 Enzyme Time-Dependent Inhibition Assay Time-dependent inhibition assay of 3A4 subtype of CYP450 enzyme using testosterone as a substrate ($IC_{50}$ shift): a system for 100 L of human liver microsomes (at a final concentration of 0.2 mg/mL) was used to pre-incubate for 30 min, with or without addition of NADPH, then incubate, with addition of 20 μL of NADPH, and the final concentration of NADPH in the system was 1.3 mM. The series of compound concentrations started from 100 μM and had a total of 8 concentration points (including 0 concentration point) by 3-fold dilutions. The positive inhibitor was mifepristone, the series of concentrations thereof started from 10 μM and had a total of 8 concentration points (including 0 concentration point) by 3-fold dilutions. The probe substrate was testosterone at a concentration of 50 μM. The reaction was terminated after incubation for 10 min. The $IC_{50}$ of the compound against enzyme was calculated by measuring the relative yield of metabolite, and the $IC_{50}$ shift was calculated from the $IC_{50}$ results of the groups pre-incubated with and without addition of NADPH.

According to the above method, the time-dependent inhibition data on 3A4 subtype of CYP450 enzyme of control compound and the compounds in Examples 4, 17, 23, 26, 27, 28 and 29 of the present disclosure are shown in Table below. The results show that the time-dependent inhibition effects on CYP3A4 of the compounds in Examples 4, 17, 23, 26, 27, 28 and 29 are all lower than that of GLPG1690, thus indicating a lower risk of drug-drug interaction in clinical practice.

| Compound | $IC_{50}$ shift |
|---|---|
| Example 4 | 1.04 |
| Example 17 | $IC_{50}$ > 100 μM/$IC_{50}$ > 100 μM |
| Example 23 | $IC_{50}$ > 100 μM/$IC_{50}$ > 100 μM |
| Example 26 | 1.09 |
| Example 27 | 0.63 |
| Example 28 | 1.28 |
| Example 29 | $IC_{50}$ > 100 μM/$IC_{50}$ > 100 μM |
| GLPG1690 | 1.64 |

Further, it will be understood by those skilled in the art that the afore-mentioned compound shown in Formula I', Formula I, Formula I-1, Formula II, Formula II-1, Formula III or Formula III-1, different implementation modes of the compound shown in Formula I', Formula I, Formula I-1, Formula II, Formula II-1, Formula III or Formula III-1, and all the compounds involved in specific embodiments of the compound shown in Formula I', Formula I, Formula I-1, Formula II, Formula II-1, Formula III or Formula III-1 can all be made into corresponding isomers, solvates, hydrates, prodrugs, stable isotope derivatives, and pharmaceutically acceptable salts. Preferably, the compound is made into a pharmaceutically acceptable derivative which is any one of a prodrug, a salt, an ester, an amide, a salt of an ester, a salt of an amide, and a metabolite.

Further, a pharmaceutically acceptable salt includes a conventional non-toxic salt which is obtained by salification of any compound of the present disclosure with an inorganic acid (such as hydrochloric acid, hydrobromic acid, sulfuric acid, or phosphoric acid) or an organic acid (such as acetic acid, propionic acid, succinic acid, benzoic acid, p-aminobenzenesulfonic acid, 2-acetoxy-benzoic acid, cinnamic acid, amygdalic acid, salicylic acid, glycolic acid, lactic acid, oxalic acid, malic acid, maleic acid, malonic acid, fumaric acid, tartaric acid, citric acid, p-toluenesulfonic acid, methanesulfonic acid, ethanesulfonic acid, or benzenesulfonic acid). For a review of suitable pharmaceutically useful salts, reference can be made to Berge S. M. et al., J. Pharm. Sci. 1977, 66, 1-19; Gould P. L. Int. J. Pharm. 1986, 33, 201-277, and Bighley et al., Encyclopedia of Pharmaceutical Technology, Marcel Dekker Inc., New York, 1996, vol. 13, pp. 453-497.

Further, a stable isotope derivative can be obtained by introducing an isotope into any compound of the present disclosure, the introduced isotope can be $^{2}H$, $^{3}H$, $^{13}C$, $^{14}C$, $^{15}N$, $^{17}O$, $^{18}O$, $^{31}P$, $^{32}P$, $^{35}S$, $^{18}F$, or $^{36}Cl$, and a specific isotope derivative can be prepared by a conventional technique.

Further, as an actual product, the compound can be formulated into any one of a tablet, a capsule, an injection, a granule, a powder, a suppository, a pill, a cream, a paste, a gel, a pulvis, an oral solution, an inhalant, a suspension, a dry suspension, a patch, and a lotion.

Further, on the basis of the above description, the compound can also form a mixture together with any of the following substances: a pharmaceutically acceptable carrier, an adjuvant or an excipient.

All the compounds of the present disclosure as well as mixtures, compositions, etc. comprising the compounds of the present disclosure can be administered to an organism by any administration route. The administration route can be oral administration, intravenous injection, intramuscular injection, subcutaneous injection, rectal administration, vaginal administration, sublingual administration, nasal inhalation, oral inhalation, ophthalmic administration, and topical or systemic transdermal administration.

All the compounds of the present disclosure as well as mixtures, compositions, etc. comprising the compounds of the present disclosure can be formulated into a single dose containing the active compound of the present disclosure, as well as a carrier, an excipient, etc., and can be administered in the form of tablet, capsule, injection, granule, powder, suppository, pill, cream, paste, gel, pulvis, oral solution, inhalant, suspension, dry suspension, patch, lotion, etc. These dosage forms can comprise the components commonly used in pharmaceutical formulations, such as diluents, absorbents, wetting agents, adhesives, disintegrants, colorants, pH adjusters, antioxidants, bacteriostatic agents, isotonic agents, anti-adhesives, etc.

Suitable formulas for the various dosage forms described above are available from publicly available sources, such as Remington: The Science and Practice of Pharmacy, 21st Edition, Lippincott Williams & Wilkins, published in 2006, and Rowe, Raymond C. Handbook of Pharmaceutical Excipients, Chicago, Pharmaceutical Press, published in 2005, therefore, they can be easily prepared by those skilled in the art.

Different administration doses can be selected according to factors such as the nature and severity of diseases from which different individuals suffer; the ages, genders, and body weights of subjects; and administration routes, the administration dose of the compound of the present disclosure can be 0.01-500 mg/kg per day, preferably 1-100 mg/kg per day, and can be administered once or multiple times.

It will be understood by those skilled in the art that, a typical application for all the compounds of the present disclosure as well as mixtures, compositions, etc. comprising the compounds of the present disclosure is a medical application, in particular for preventing or treating diseases in mammals with the pathologic feature of increased ATX expression, specifically, the specific indications are as follows:

cancer, fibrotic diseases, metabolic diseases, myelodysplastic syndrome, respiratory diseases, cardiovascular diseases, autoimmune diseases, inflammation, dermatological diseases, nervous system diseases, or pain.

Specific embodiments of the present disclosure are described above in detail. It is to be understood that the present disclosure is not limited to the particular embodiments described above and that various variations or modifications can be made within the scope of the claims by those skilled in the art without substantially affecting the present disclosure.

What is claimed is:

1. A compound of Formula I' or a pharmaceutically acceptable salt thereof,

I'

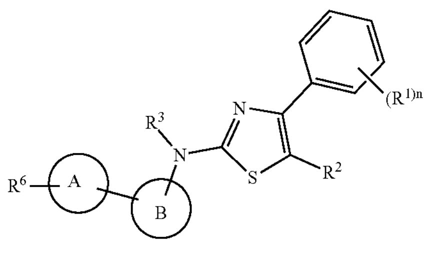

wherein n is any integer from 0 to 5;

if present, each $R^1$ is independently selected from the group consisting of hydrogen, deuterium, cyano, halogen, amino, hydroxyl, —COOH, —CHO, —$NO_2$, $C_{1-6}$ alkylamino, $C_{1-6}$ alkoxy, and $C_{1-6}$ alkyl, $C_{3-7}$ cycloalkyl and 3- to 7-membered heterocycloalkyl that are unsubstituted or substituted with substituents selected from the group consisting of cyano, amino, hydroxyl, halogen, $C_{1-6}$ alkyl, and $C_{1-6}$ alkoxy;

$R^2$ is selected from the group consisting of hydrogen, deuterium, halogen, cyano, amino, hydroxyl, —COOH, —CHO, —$NO_2$, $C_{1-6}$ alkyl, $C_{1-6}$ alkoxy, $C_{1-6}$ alkylamino, —C(=O)$NH_2$, —NH(C=O)$CH_3$, and 3- to 7-membered heterocycloalkyl;

$R^3$ is selected from the group consisting of hydrogen, deuterium, $C_{1-6}$ alkyl, $C_{3-7}$ cycloalkyl, and $C_{1-6}$ alkyl, $C_{3-7}$ cycloalkyl and 3- to 7-membered heterocycloalkyl that are substituted with substituents selected from the group consisting of cyano, amino, hydroxyl, halogen, $C_{1-6}$ alkyl, and $C_{1-6}$ alkoxy;

ring B is selected from the group consisting of:

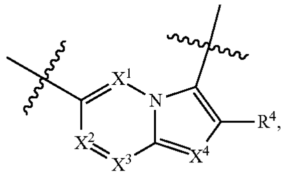

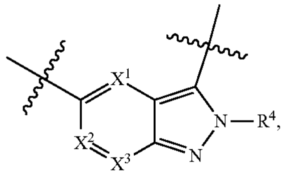

and

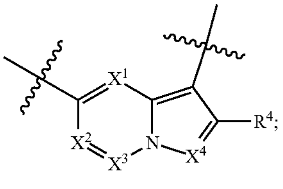

$R^4$ is selected from the group consisting of hydrogen, deuterium, halogen, cyano, hydroxyl, amino, $C_{1-6}$ alkyl, $C_{1-6}$ alkoxy, $C_{1-6}$ alkylamino, $C_{3-7}$ cycloalkyl, and 3- to 7-membered heterocycloalkyl;

$X^1$, $X^2$, $X^3$ and $X^4$ are each independently N or $CR^5$;

$R^5$ is selected from the group consisting of hydrogen, deuterium, halogen, $C_{1-6}$ alkyl, and $C_{1-6}$ alkyl, $C_{3-7}$ cycloalkyl and 3- to 7-membered heterocycloalkyl that are substituted with substituents selected from the group consisting of cyano, amino, hydroxyl, halogen, $C_{1-6}$ alkyl, and $C_{1-6}$ alkoxy;

ring A is selected from the group consisting of

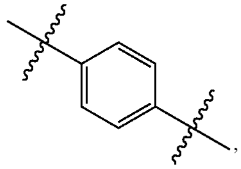, 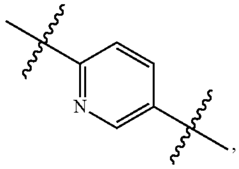,
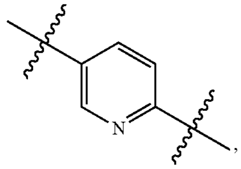, 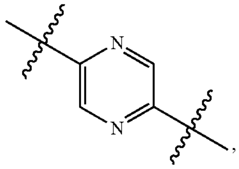,
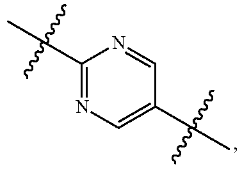, 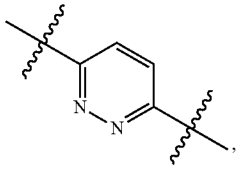,
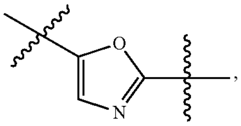, 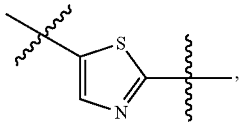,
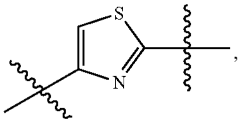, 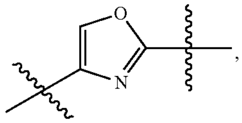,
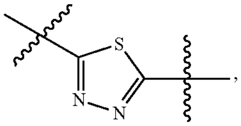, 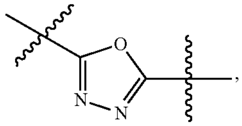,
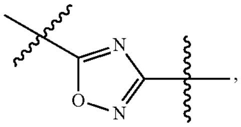, 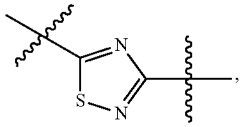,
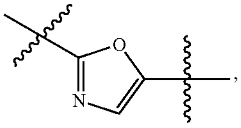, 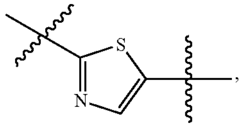,
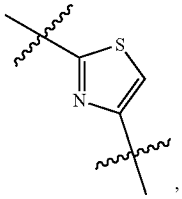, and 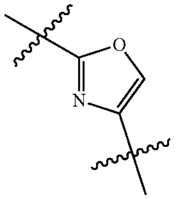

and that are substituted or unsubstituted, and the substitution is a substitution with 1 to 3 substituents selected from the group consisting of hydroxyl, amino, halogen, cyano, $C_{1-6}$ alkyl, $C_{1-6}$ haloalkyl, $C_{3-7}$ cycloalkyl, 3- to 7-membered heterocycloalkyl, $C_{1-6}$ alkylamino, and $C_{1-6}$ alkoxy;

$R^6$ is $-L^1-L^2-W^1$;

$L^1$ is selected from the group consisting of a chemical bond, $C_{1-3}$ alkylene, —O—, —C(═O)—, —C(═O)C$(R^8)_2$—, —C(═O)O—, —C(═O)NH—, —OC(═O)—, —NH—, —$SO_2$—, —$NHSO_2$—, and —$SO_2NH$—; wherein $R^8$ is hydrogen or $C_{1-6}$ alkyl;

$L^2$ is selected from the group consisting of a chemical bond, —O—, —C(═O)—, —C(═O)$CH_2$—, —C(═O)O—, —OC(═O)—, —C(═O)NH—, —$NR^7$—, —$NHCH_2$—, —$SO_2$—, —$NR^7SO_2$—, —$SO_2NR^7$—, —C(═O)$NR^7$—, and —$NR^7$C(═O)—; wherein $R^7$ is hydrogen or $C_{1-6}$ alkyl;

$W^1$ is a substituted or unsubstituted group as follows: amino, cyano, $C_{1-6}$ alkyl, halogen, hydroxyl, $C_{1-6}$ alkoxy, $C_{1-6}$ alkylamino, carboxyl, $C_{6-10}$ aryl, 5- to 10-membered heteroaryl, $C_{3-7}$ cycloalkyl or 3- to 7-membered heterocycloalkyl; the substitution is a substitution with 1 or 2 substituents selected from the group consisting of oxo, hydroxy, amino, hydroxymethyl, aminomethyl, cyano, $C_{1-6}$ alkyl, $C_{1-6}$ alkyl-C(═O)O—, and halogen.

2. The compound or the pharmaceutically acceptable salt thereof according to claim 1, wherein n is any integer from 0 to 2; and each $R^1$ is independently selected from the group consisting of hydrogen, cyano and halogen.

3. The compound or the pharmaceutically acceptable salt thereof according to claim 1, wherein $R^2$ is cyano.

4. The compound or the pharmaceutically acceptable thereof according to claim 1, wherein $R^3$ is $C_{1-6}$ alkyl.

5. The compound or the pharmaceutically acceptable salt thereof according to claim 1, wherein ring B is selected from the group consisting of:

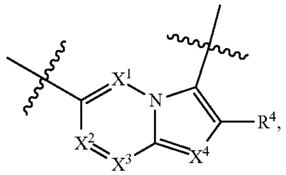

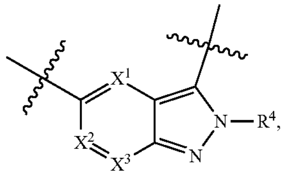 and

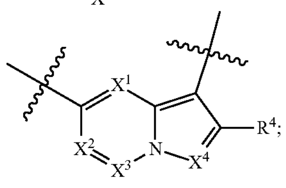

$X^1$, $X^2$, $X^3$ and $X^4$ are each independently N or $CR^5$;

$R^5$ is selected from the group consisting of hydrogen, deuterium, halogen, methyl, and halomethyl;

$R^4$ is selected from the group consisting of hydrogen, deuterium, methyl, ethyl, isopropyl, and cyclopropyl.

6. The compound or the pharmaceutically acceptable salt thereof according to claim 1, wherein ring A is any one selected from the group consisting of:

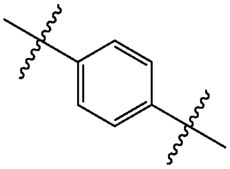,
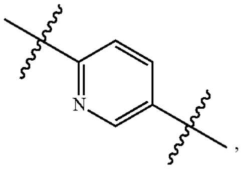,
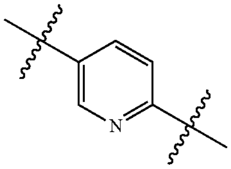,
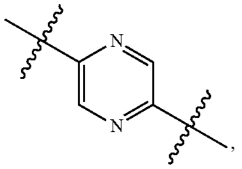,
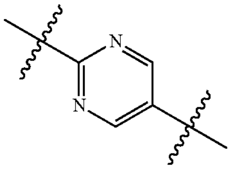, and
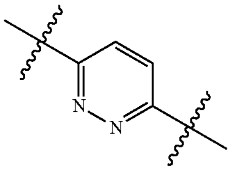, 7. The compound or the pharmaceutically acceptable salt thereof according to claim 6, wherein ring A is substituted with 1 to 3 substituents, the substituents being each independently selected from the group consisting of hydroxyl, amino, halogen, cyano, and $C_{1-6}$ alkyl.

8. The compound or the pharmaceutically acceptable salt thereof according to claim 1, wherein $L^1$ is selected from the group consisting of a chemical bond, —$CH_2$—, —$CH(CH_3)$—, —$C(CH_3)_2$—, —C(═O)—, —$SO_2$—, —C(═O)$CH_2$—, and —C(═O)NH—.

9. The compound or the pharmaceutically acceptable salt thereof according to claim 1, wherein $L^2$ is selected from the group consisting of a chemical bond, —NH—, —C(═O)—, —$SO_2$—, —$NHCH_2$—, —C(═O)$CH_2$—, —C(═O)NH—, —$NHSO_2$—, and —N($CH_3$)$SO_2$—.

10. The compound or the pharmaceutically acceptable salt thereof according to claim 1, wherein $W^1$ is a substituted or unsubstituted group as follows: $C_{1-6}$ alkyl, $C_{6-10}$ aryl, 5- to 10-membered heteroaryl, $C_{3-7}$ cycloalkyl or 3- to 7-membered heterocycloalkyl, and the substitution is a substitution with 1 or 2 substituents selected from the group consisting of oxo, hydroxy, amino, hydroxymethyl, aminomethyl, halogen, cyano, $C_{1-6}$ alkyl-C(═O)O—, and $C_{1-6}$ alkyl.

11. The compound or the pharmaceutically acceptable salt thereof according to claim 10, wherein $W^1$ is $C_{1-6}$ alkyl, $C_{3-7}$ cycloalkyl or 3- to 7-membered heterocycloalkyl which is unsubstituted or substituted with 1 or 2 substituents selected from the group consisting of hydroxy, amino, hydroxymethyl, aminomethyl, and $C_{1-6}$ alkyl-C(═O)O—.

12. The compound or the pharmaceutically acceptable salt thereof according to claim 11, wherein $W^1$ is a group as follows: methyl, ethyl, n-propyl, isopropyl, cyclopropyl, cyclobutyl, cyclopentyl, cyclohexyl, aziridinyl, azetidinyl, pyrrolidinyl, oxopyrrolidinyl, piperidinyl, piperazinyl, morpholinyl, thiomorpholinyl, oxetanyl, tetrahydrofuranyl, tetrahydrothienyl, tetrahydropyranyl, 1,1-dioxidothiomorpholinyl, 2-azaspiro [3.3]heptyl, 1,1-dioxidoisothiazolidinyl, or 1,1-dioxido-1,2-thiazinanyl which is unsubstituted or substituted with 1 or 2 substituents selected from the group consisting of hydroxy, amino, hydroxymethyl, aminomethyl, and acetoxy.

13. The compound or the pharmaceutically acceptable salt thereof according to claim 1, wherein n is 1;

$R^1$ is fluorine;

$R^2$ is cyano;

$R^3$ is methyl or ethyl;

Ring B is any one of the following structures:

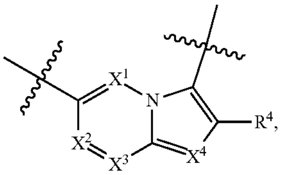,
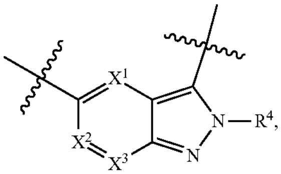, and
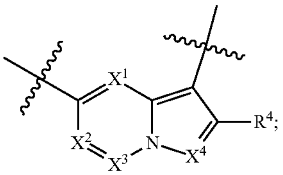;

$R^4$ is ethyl;

$X^1$, $X^2$, $X^3$ and $X^4$ are each independently N or CH;

ring A is selected from the group consisting of:

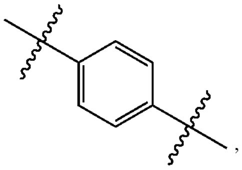,
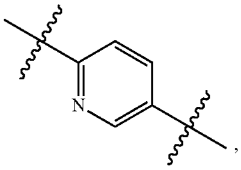,
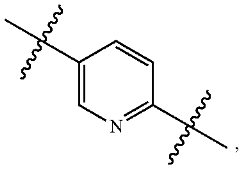,
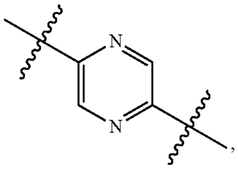,
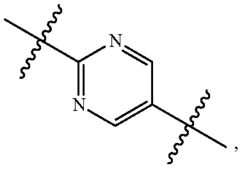, and

-continued

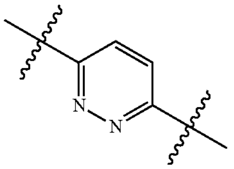;

ring A is unsubstituted or substituted with one fluorine or methyl;

$R^6$ is $-L^1-L^2-W^1$;

$L^1$ is selected from the group consisting of a chemical bond, $—CH_2—$, $—C(CH_3)_2—$, and $—C(=O)CH_2—$;

$L^2$ is selected from the group consisting of a chemical bond, $—C(=O)—$, $—NHCH_2—$, $—C(=O)NH—$, $—NHSO_2—$, and $—N(CH_3)SO_2—$;

$W^1$ is selected from the group consisting of:

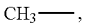, 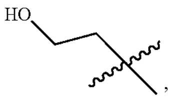, 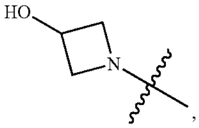, 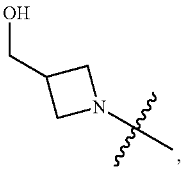, 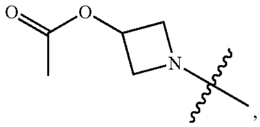, 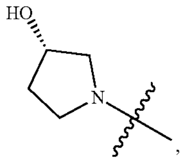, 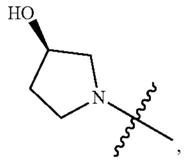, 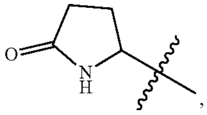, 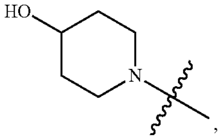, 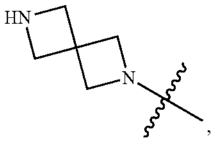, 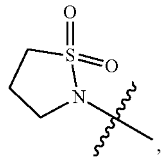, and

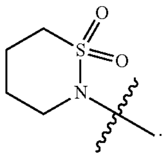.

14. The compound or the pharmaceutically acceptable salt thereof according to claim 1, wherein the compound is a compound having a structure of Formula I,

I

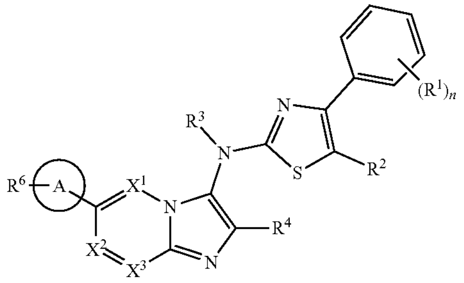

wherein n, $R^1$, $R^2$, $R^3$, $R^4$, $R^6$, $X^1$, $X^2$, $X^3$, and ring A are as defined in claim 1.

15. The compound or the pharmaceutically acceptable salt thereof according to claim 1, wherein the compound is a compound having a structure of Formula I-1,

I-1

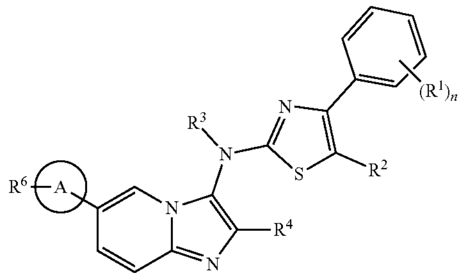

wherein n, $R^1$, $R^2$, $R^3$, $R^4$, $R^6$, and ring A are as defined in claim 1.

16. The compound or the pharmaceutically acceptable salt thereof according to claim 1, wherein the compound is a compound having a structure of Formula II,

II

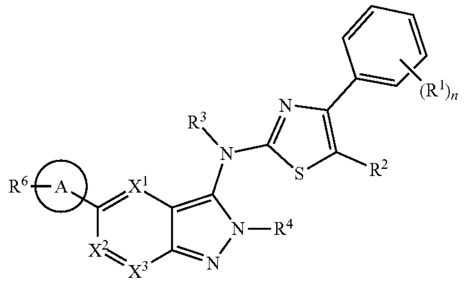

wherein n, $R^1$, $R^2$, $R^3$, $R^4$, $R^6$, $X^1$, $X^2$, $X^3$, and ring A are as defined in claim 1.

17. The compound or the pharmaceutically acceptable salt thereof according to claim 1, wherein the compound is a compound having a structure of Formula II-1,

II-1

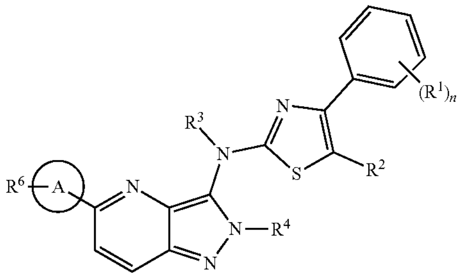

wherein n, $R^1$, $R^2$, $R^3$, $R^4$, $R^6$, and ring A are as defined in claim 1.

18. The compound or the pharmaceutically acceptable salt thereof according to claim 1, wherein the compound is a compound having a structure of Formula III,

III

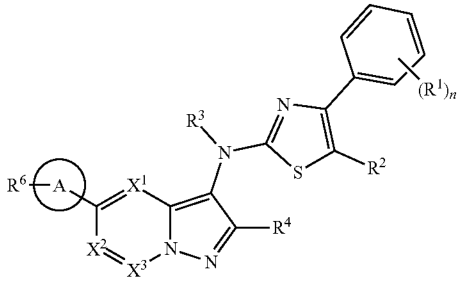

wherein n, $R^1$, $R^2$, $R^3$, $R^4$, $R^6$, $X^1$, $X^2$, $X^3$, and ring A are as defined in claim 1.

19. The compound or the pharmaceutically acceptable salt thereof according to claim 1, wherein the compound is a compound having a structure of Formula III-1,

III-1

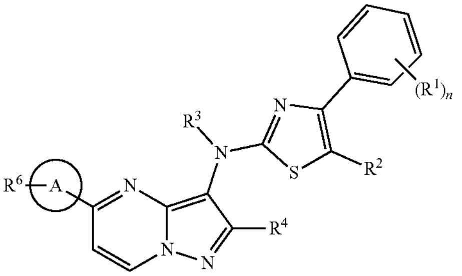

wherein n, $R^1$, $R^2$, $R^3$, $R^4$, $R^6$, and ring A are as defined in claim 1.

20. A compound as follows or a pharmaceutically acceptable salt thereof:

1

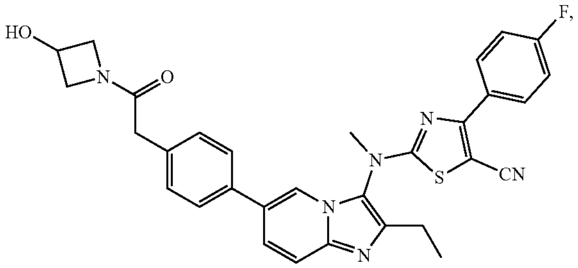

2

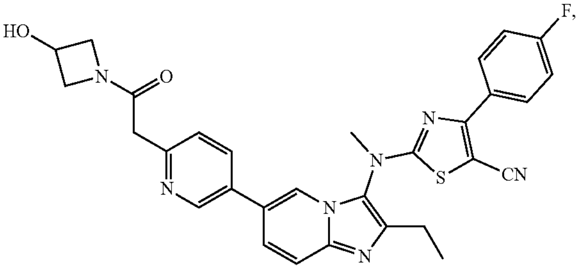

3

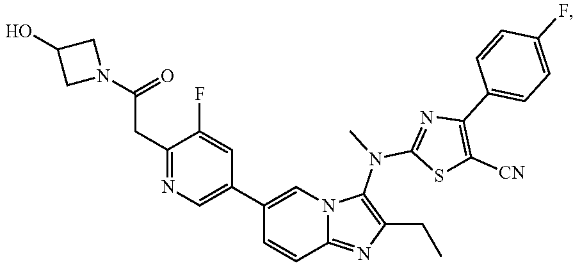

4

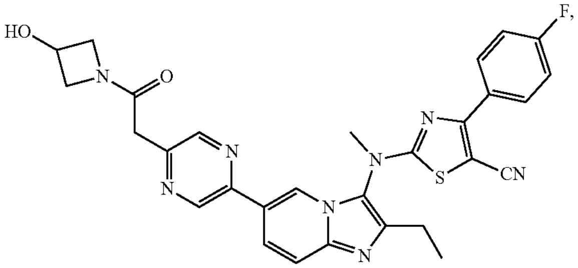

5

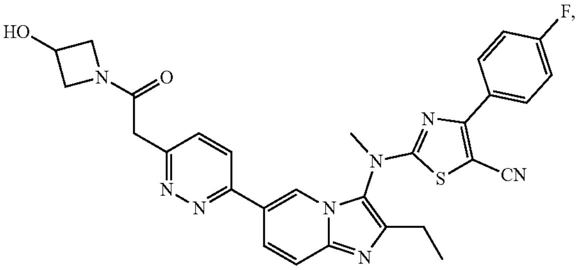

-continued
6
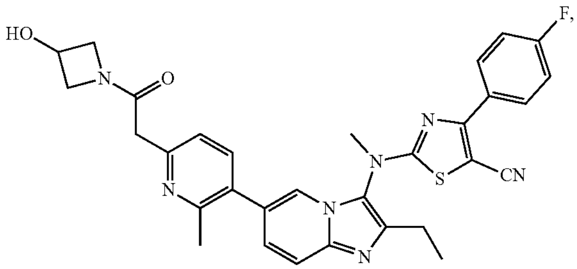
7
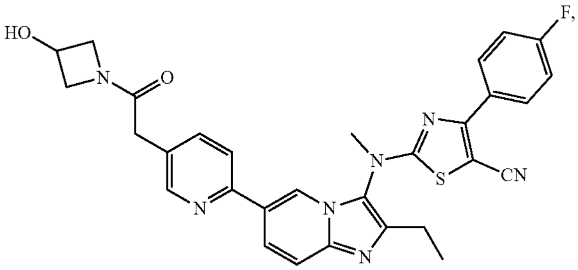
8
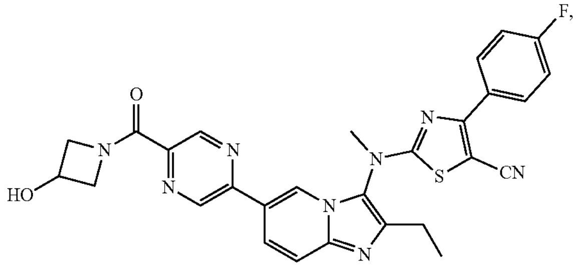
9
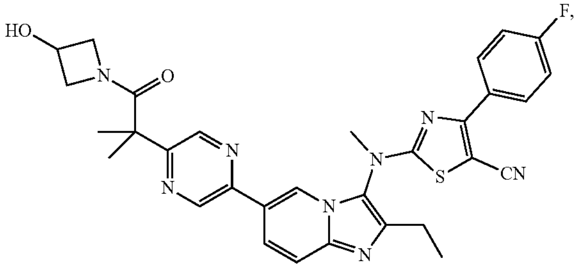
10
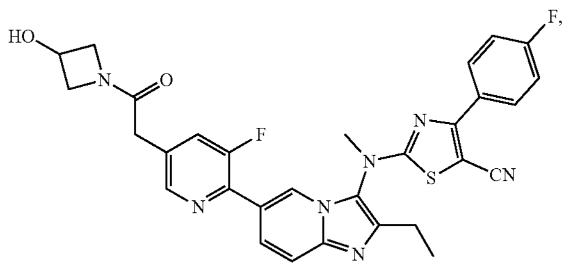
-continued
11
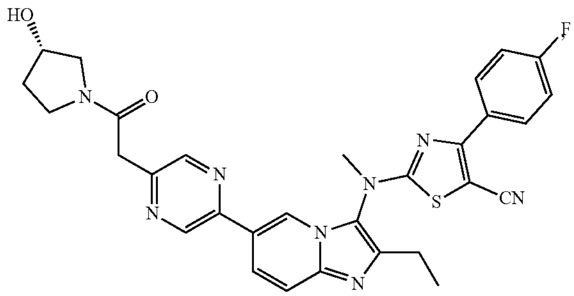
12
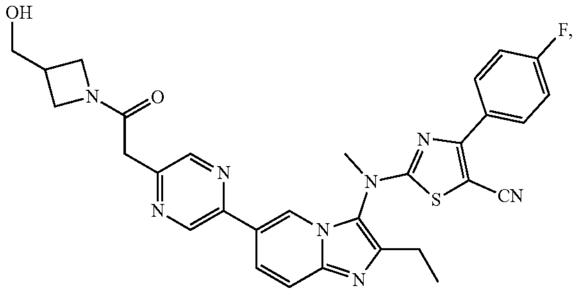
13
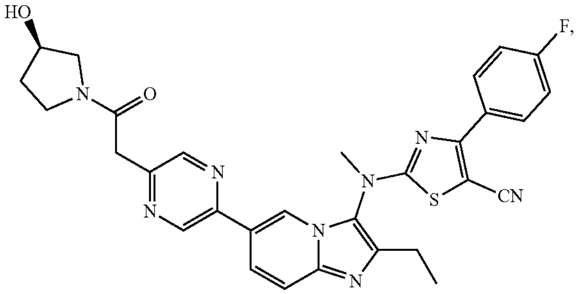
14
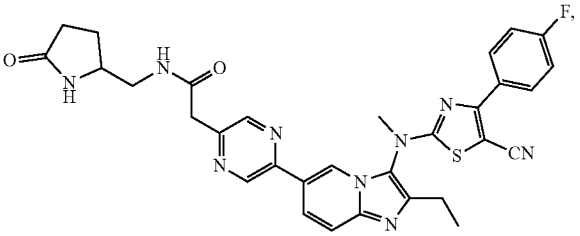
15
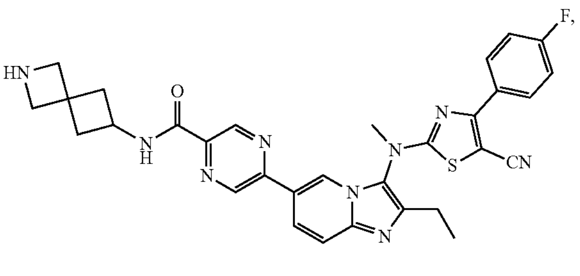

16
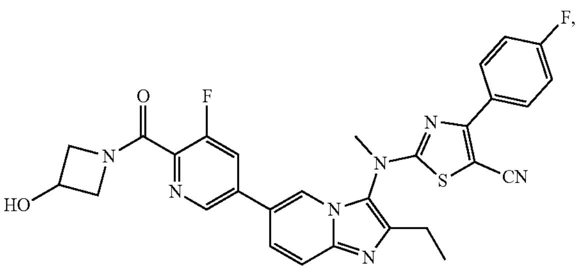
17
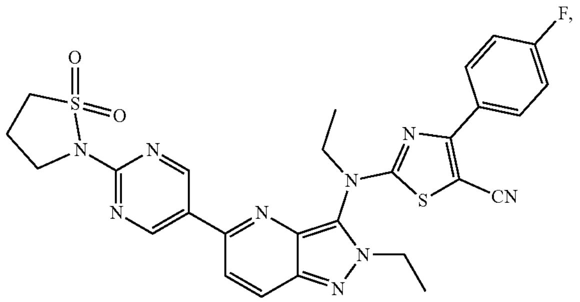
18
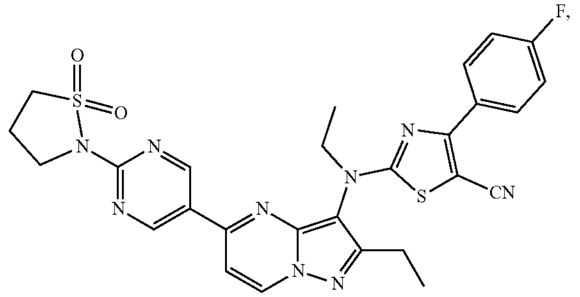
19
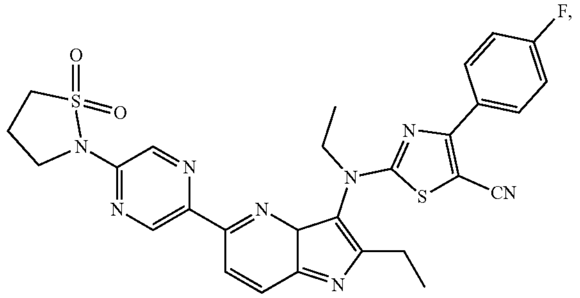
20
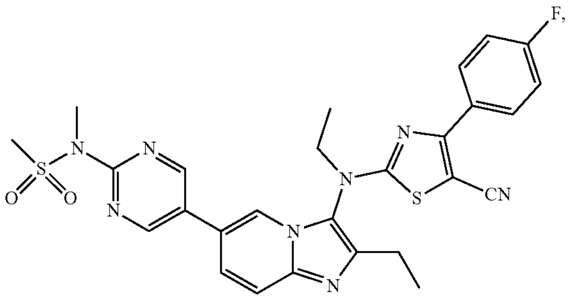
21
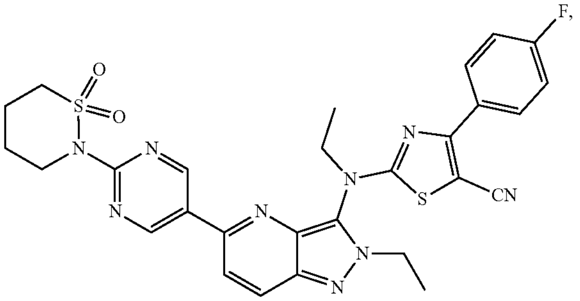
22
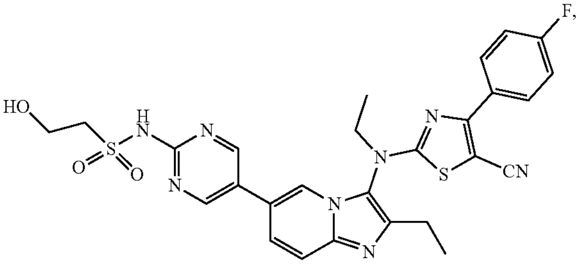
23
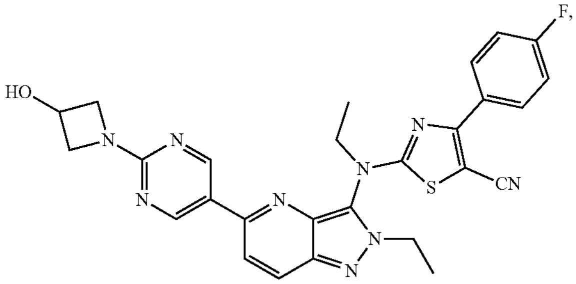
24
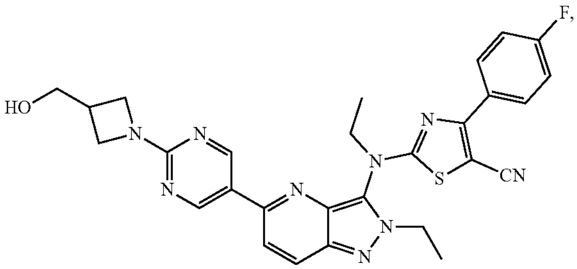
25
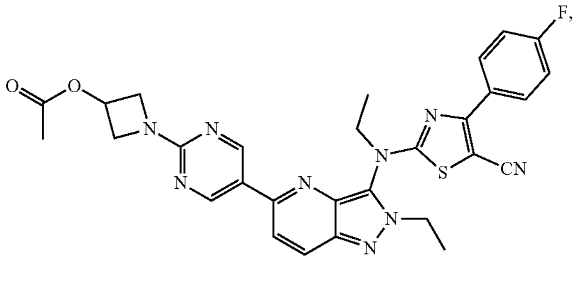

-continued

26

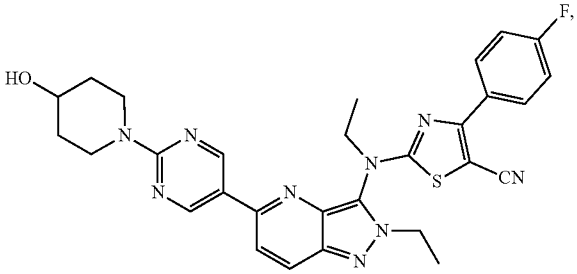

F,

27

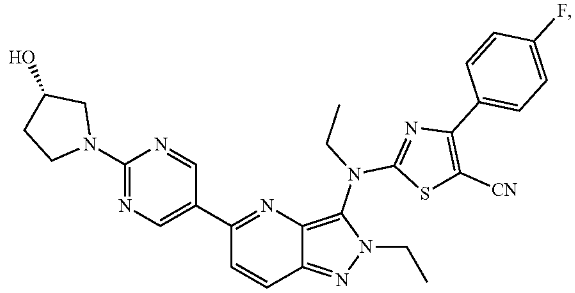

F,

28

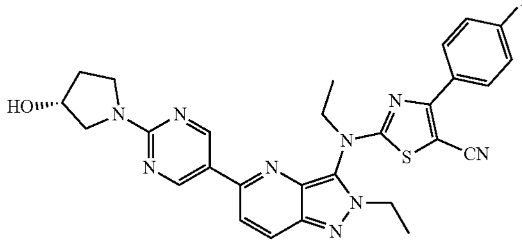

F, and

-continued

29

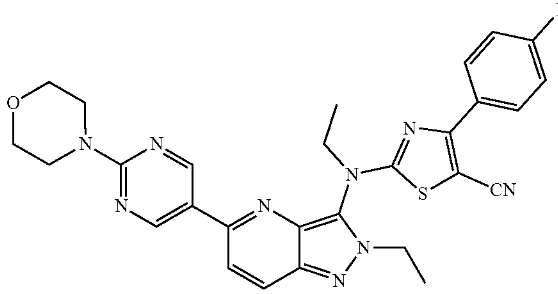

F.

21. A pharmaceutical composition, comprising the compound or the pharmaceutically acceptable salt thereof according to claim 1.

22. A pharmaceutical formulation, comprising the compound or the pharmaceutically acceptable salt thereof according to claim 1;

the pharmaceutical formulation is selected from the group consisting of a tablet, a capsule, an injection, a granule, a powder, a suppository, a pill, a cream, a paste, a gel, a pulvis, an oral solution, an inhalant, a suspension, a dry suspension, a patch, and a lotion.

23. A method for treating a related cancer, fibrotic diseases, metabolic diseases, myelodysplastic syndrome, respiratory diseases, cardiovascular diseases, autoimmune diseases, inflammation, dermatological diseases, nervous system diseases, or pain associated with a pathologic feature of increased ATX expression, comprising the step of administrating an effective amount of the compound or the pharmaceutically acceptable salt thereof according to claim 1, to a subject in need thereof.

* * * * *